United States Patent
Braun

(10) Patent No.: US 12,329,429 B2
(45) Date of Patent: Jun. 17, 2025

(54) SYSTEMS, METHODS, AND APPARATUS FOR SPINAL DEFORMITY CORRECTION

(71) Applicant: BraunVest LLC., Charlotte, VT (US)

(72) Inventor: John T. Braun, Charlotte, VT (US)

(73) Assignee: Braunvest LLC, Charlotte, VT (US)

( * ) Notice: Subject to any disclaimer, the term of this patent is extended or adjusted under 35 U.S.C. 154(b) by 903 days.

(21) Appl. No.: 17/452,774

(22) Filed: Oct. 28, 2021

(65) Prior Publication Data

US 2022/0160411 A1    May 26, 2022

Related U.S. Application Data

(63) Continuation-in-part of application No. 16/601,471, filed on Oct. 14, 2019, now Pat. No. 11,246,636.

(60) Provisional application No. 62/839,397, filed on Apr. 26, 2019.

(51) Int. Cl.
*A61B 17/86* (2006.01)
*A61B 17/70* (2006.01)
*A61B 17/56* (2006.01)

(52) U.S. Cl.
CPC ...... *A61B 17/8635* (2013.01); *A61B 17/7022* (2013.01); *A61B 17/8605* (2013.01); *A61B 17/863* (2013.01); *A61B 2017/564* (2013.01); *A61B 2017/8655* (2013.01)

(58) Field of Classification Search
CPC .......................... A61B 17/8635; A61B 17/864
See application file for complete search history.

(56) References Cited

U.S. PATENT DOCUMENTS

| | | | |
|---|---|---|---|
| 5,387,213 | A | 2/1995 | Breard et al. |
| 5,951,560 | A | 9/1999 | Simon et al. |
| 6,299,613 | B1 | 10/2001 | Ogilvie et al. |
| 7,285,121 | B2 | 10/2007 | Braun et al. |
| 7,297,146 | B2 | 11/2007 | Braun et al. |
| 7,637,978 | B2 | 12/2009 | Jung |
| 7,691,131 | B2 | 4/2010 | Graf |
| 7,727,258 | B2 | 6/2010 | Graf |
| 7,845,945 | B2 * | 12/2010 | Canter ................. A61C 8/0022 433/173 |

(Continued)

FOREIGN PATENT DOCUMENTS

| | | |
|---|---|---|
| WO | WO2009128074 | 10/2009 |
| WO | WO2017127532 | 7/2017 |

OTHER PUBLICATIONS

U.S. Appl. No. 16/601,471, Office Action dated May 27, 2021 (8 pgs.).

*Primary Examiner* — Christian A Sevilla
(74) *Attorney, Agent, or Firm* — Matthew D. Thayne; Thayne and Davis LLC

(57) ABSTRACT

Bone anchors and related systems and methods for spinal deformity correction. In some implementations, two adjacent bone anchors may be advanced into respective, adjacent vertebral bodies of a spinal column. Cancellous bone may be compacted within respective inner chambers of the bone anchors. The inner chambers may comprise at least one of a plurality of bone engaging protrusions and a profile that increases in cross-sectional area, at least in part, from a proximal end of the inner chambers to a distal end of the inner chambers. A tether may then be coupled between the first and second bone anchors to apply a corrective force to at least a portion of the spinal column.

20 Claims, 28 Drawing Sheets

(56) References Cited

U.S. PATENT DOCUMENTS

| | | | |
|---|---|---|---|
| 7,862,573 B2 * | 1/2011 | Darois | B25B 23/065 |
| | | | 606/139 |
| 8,128,402 B2 * | 3/2012 | Lundgren | A61C 8/0092 |
| | | | 433/174 |
| 8,172,880 B2 | 5/2012 | Graf | |
| 8,177,810 B2 | 5/2012 | Ferree | |
| 8,221,457 B2 | 7/2012 | Delecrin et al. | |
| 8,641,736 B2 | 2/2014 | Marik et al. | |
| 8,870,573 B2 * | 10/2014 | Hung | A61C 8/0039 |
| | | | 433/174 |
| 8,979,874 B2 | 3/2015 | Darois et al. | |
| 9,271,725 B2 * | 3/2016 | Colesanti | A61B 17/068 |
| 9,433,442 B2 | 9/2016 | Lindemann et al. | |
| 9,833,230 B2 | 12/2017 | Stone | |
| 10,179,015 B2 | 1/2019 | Lavigne et al. | |
| 11,246,636 B2 | 2/2022 | Braun | |
| 2002/0082598 A1 | 6/2002 | Teitelbaum | |
| 2007/0292820 A1 * | 12/2007 | Canter | A61C 8/0022 |
| | | | 606/304 |
| 2010/0131010 A1 | 5/2010 | Graf | |
| 2012/0189984 A1 | 7/2012 | Holmes | |
| 2013/0253587 A1 | 9/2013 | Carls et al. | |
| 2013/0304032 A1 | 11/2013 | Sardesai | |
| 2020/0337753 A1 | 10/2020 | Braun | |

\* cited by examiner

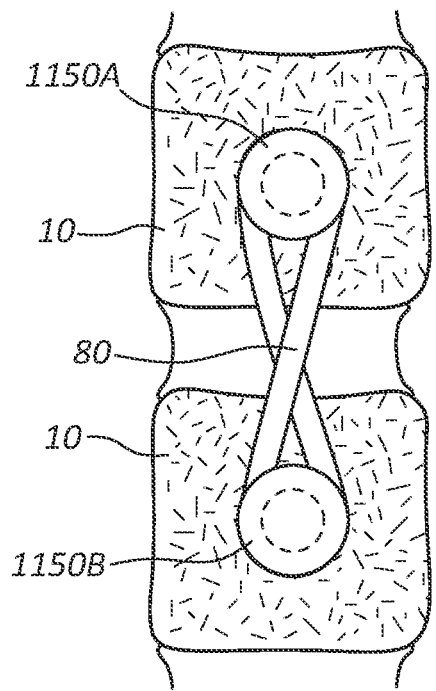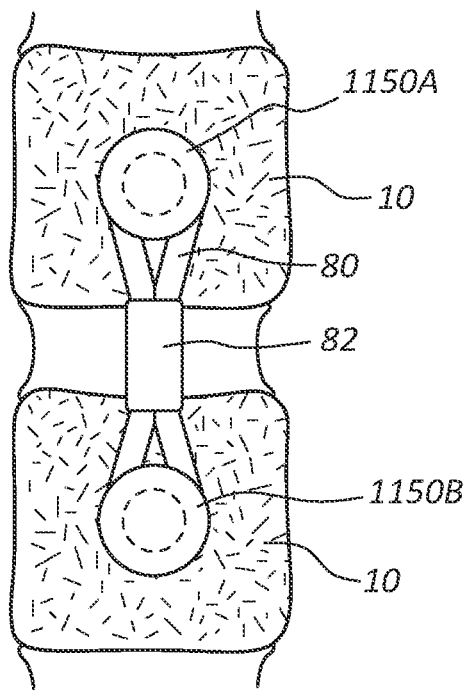
*FIG. 11A*  *FIG. 11B*
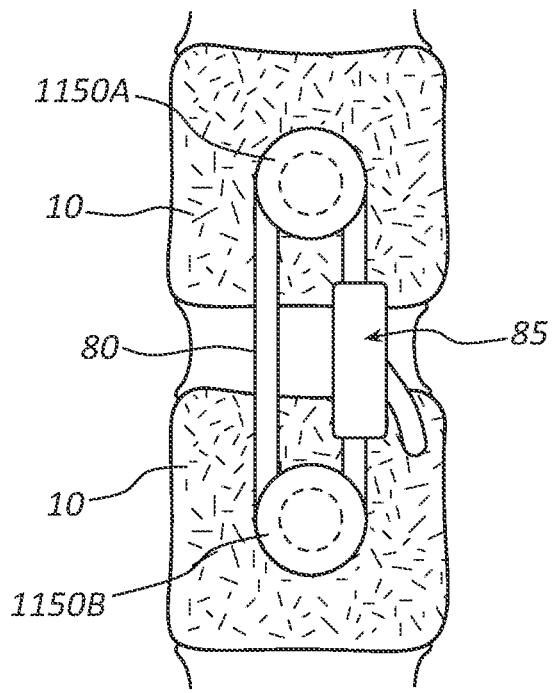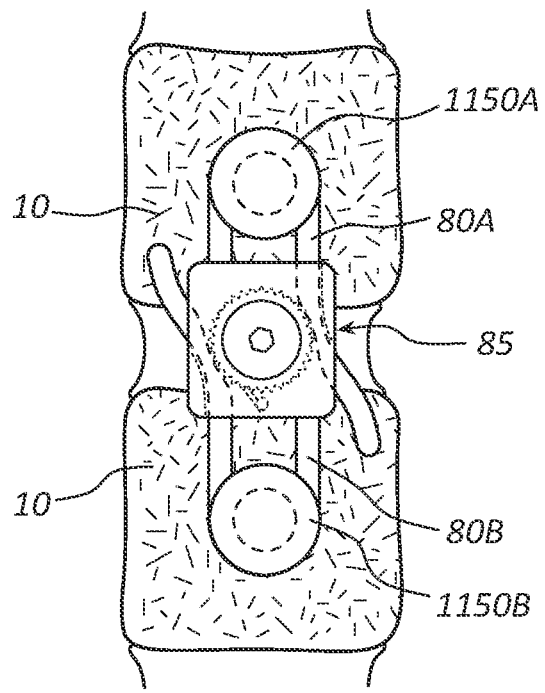
*FIG. 11C*  *FIG. 11D*

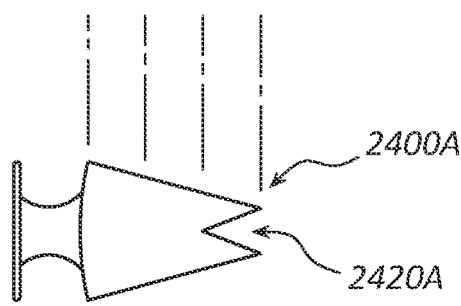
FIG. 24A
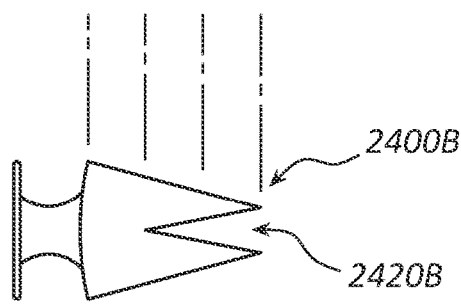
FIG. 24B
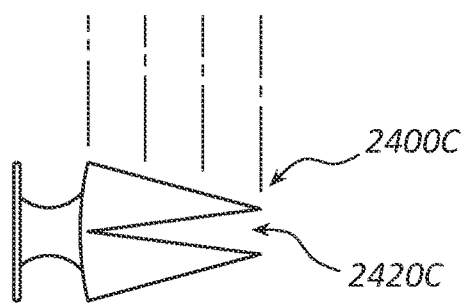
FIG. 24C
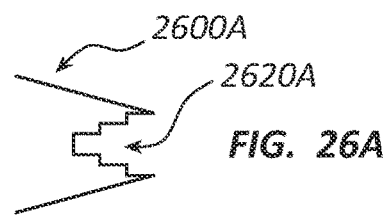
FIG. 26A
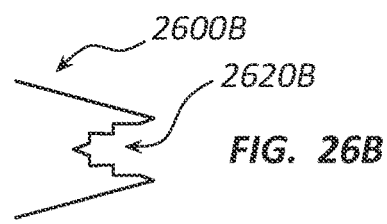
FIG. 26B
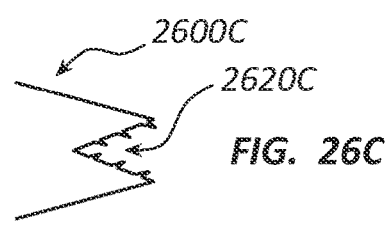
FIG. 26C
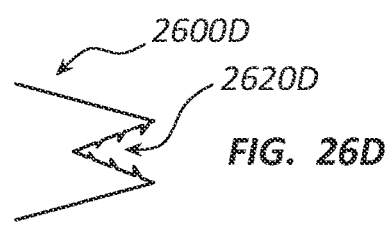
FIG. 26D
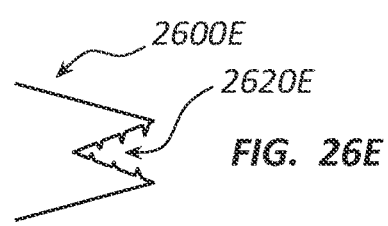
FIG. 26E
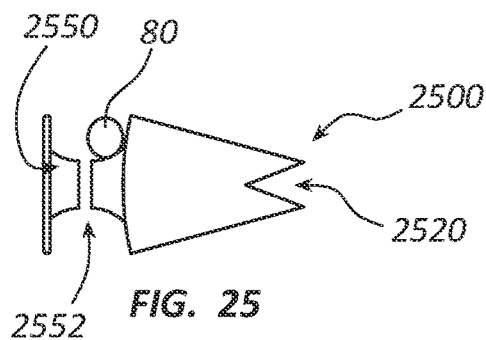
FIG. 25
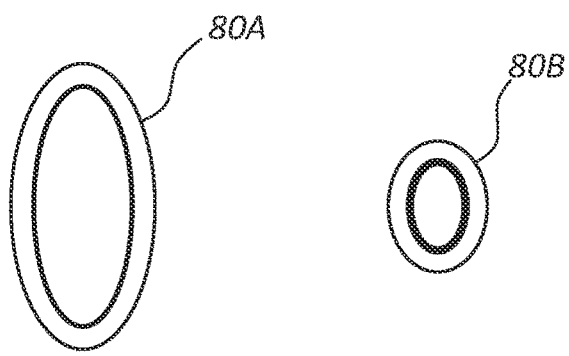
FIG. 27A
FIG. 27B

SYSTEMS, METHODS, AND APPARATUS FOR SPINAL DEFORMITY CORRECTION

CROSS-REFERENCE TO RELATED APPLICATIONS

This application is a continuation-in-part of co-pending U.S. patent application Ser. No. 16/601,471 filed on Oct. 14, 2019 and titled "SYSTEMS, METHODS, AND APPARATUS FOR SPINAL DEFORMITY CORRECTION," which application claims the benefit under 35 U.S.C. § 119(e) of U.S. Provisional Patent Application No. 62/839,397, which was filed Apr. 26, 2019 and titled "SYSTEMS, METHODS, AND APPARATUS FOR SPINAL DEFORMITY CORRECTION." Each of the aforementioned applications is hereby incorporated herein by reference in its entirety.

SUMMARY

Embodiments of apparatus and methods are disclosed herein that relate to correction and/or stabilization of spinal deformities, such as scoliosis. In some specific embodiments disclosed herein, such devices and/or systems may comprise bone anchors that may be particularly configured for coupling with vertebral bodies and that may be used in certain spinal surgeries, such as fusionless spinal surgeries that are often used to treat scoliosis and other similar deformities.

Existing bone anchors used for such procedures are typically configured to extend entirely through the vertebral bodies to provide for bicortical purchase. This is because the cortex portion of the vertebral body is viewed as the only portion of the bone with sufficient strength to hold the screw or other bone anchor in place while the corrective forces are being applied to the spinal column via a series of such screws/anchors. Inadequate screw purchase, such as purchase that terminates within the cancellous portion of the vertebra may therefore result in undesirable movement of the screw within the vertebral body, which may result in recurrence of the spinal deformity or at least decreased efficacy of the spinal correction system.

Other anchors have been developed, such as those disclosed in U.S. Pat. No. 7,285,121 titled "Devices and Methods for the Correction and Treatment of Spinal Deformities," which patent is incorporated herein by reference in its entirety. The anchors disclosed in this previous patent are shorter in length but wider to provide additional surface area for obtaining stable purchase in the cancellous bone without necessarily requiring bicortical purchase. However, the present inventor has improved upon this design by providing, in some embodiments, an inner chamber that is threaded, which may provide a number of benefits, such as drawing additional bone into the chamber, placing such bone under compression to accelerate healing and incorporation with the implant, and/or providing a differential in force and/or surface tension between various portions of the anchor, such as between the inner and outer surfaces of the implant, to further improve stability, healing, and/or provide other benefits.

Although the preferred embodiments disclosed herein are designed and configured for use in connection with spinal bones, such as vertebral bodies, the inventive principles disclosed herein may find application in other types of bones or even other types of tissues, particularly bones and/or tissues with similar characteristics to vertebral bones (i.e., largely cancellous bone/tissue and/or comprising an insufficient cortex). Examples of such alternative applications include suture anchors for rotator cuff repair and other similar surgical procedures. It should be understood therefore that the bone anchors and other features/aspects disclosed herein may be used in connection with any bones or other anatomical feature, including but not limited to those involving use of sutures and/or tethers for applying a force to such anatomical feature, but particularly those features having both cortical and cancellous bone regions.

Thus, in a more specific example of a bone anchor, such as a bone anchor configured for vertebral attachment, the bone anchor may comprise an outer thread form that may be positioned on a tapered portion of the bone anchor. The bone anchor may further comprise an inner chamber, which may be located along the same portion along the primary axis of the bone anchor. The inner chamber may also comprise a thread form and/or may taper in an opposite direction. The inner and outer thread forms may differ from one another, such as by providing a larger thread depth on the thread form in the inner chamber, for example. Similarly, the inner and outer threads may differ in other aspects to increase the aforementioned force differential, such as by differing in thread direction/handedness, number of starts, angle, pitch diameter, major diameter, minor diameter, etc.

This may allow for increased fixation while increasing stimulation of bone ingrowth by increasing the forces that stimulate such bone growth. In other words, by providing an inner chamber that has threads and/or tapers, as described herein, bone may be inserted into and compacted within the chamber as the anchor is advanced. Although providing a tapered chamber or a chamber that otherwise decreases in volume from the distal end towards the proximal end is preferred, some such benefits may be provided by providing a cylindrical chamber comprising internal threads.

In some embodiments, the bone anchor may further comprise an engagement member or other means for engaging a ligament to impart a force to a vertebral body or other tissue or anatomical feature. Such engagement member or other feature may be incorporated directly into the bone anchor or may be part of a cap or other such element that may be coupled with the bone anchor. In some embodiments, the engagement member or engagement means and/or a cap or the like to which the engagement member/means is coupled may be rotatable with respect to the thread form(s) of the anchor to allow for selective repositioning of the engagement member/means following insertion of the bone anchor into a vertebral body or other bone or body tissue.

In a more specific example of a bone anchor, such as a bone screw or other bone anchor, configured for engagement with a vertebral body or other bone, the anchor may comprise a first section comprising an at least substantially conical shape in cross section and a second section comprising an at least substantially cylindrical shape in cross section. The second section may be positioned distal of the first section and may form a tip of the bone anchor. The bone anchor may further comprise an inner chamber. An outer thread form may be formed on an outer surface of the bone anchor and an inner thread form may be formed on an inner surface of the bone anchor within the inner chamber.

Some embodiments may further comprise a third section, which may comprise a cross-sectional width in a direction at least substantially perpendicular to an elongated axis of the bone anchor. The cross-sectional width may be maximal between opposing ends of the third section. In some such embodiments, the third section may comprise an outer surface having a convex, curved shape. The third section may be positioned in between the first section and the second section.

In some embodiments, the third section may comprise an outer thread form, which may, in some embodiments, begin at or at least substantially at a point of maximal width of the third section.

In some embodiments, the inner thread form may differ from the outer thread form so as to provide a differential in force between forces generated by the outer thread form on vertebral bone adjacent to the outer thread form and forces generated by the inner thread form on vertebral bone within the inner chamber.

In some embodiments, the second section may lack outer threads. In some embodiments, the second section may also, or alternatively, lack inner threads. The second section and/or distal most end of the bone anchor may comprise a sharp edge configured to facilitate penetration into a vertebral body.

In another example of a threaded bone anchor configured for engagement with a vertebral body, the anchor may comprise a tapered section comprising an outer thread form and an inner chamber comprising an inner thread form. The inner chamber may comprise a proximal end and a distal end and may taper or otherwise decrease in size, at least in part, between the distal end and the proximal end. The inner thread form may differ from the outer thread form so as to provide a differential in force between forces generated by the outer thread form on vertebral bone adjacent to the outer thread form and forces generated by the inner thread form on vertebral bone within the inner chamber, such as by differing in one or more of thread depth, thread direction, number of starts, angle, pitch diameter, major diameter, taper angle, and minor diameter. As a more specific example, in some embodiments, the inner thread form may comprise a larger thread depth than the outer thread form. Any of the aforementioned threads may be partial and/or transition along the thread form as well, if desired.

In some embodiments, the inner chamber may taper, in part or in whole, from a proximal portion of the bone anchor to a distal portion of the bone anchor to define a wider bone anchor width at a proximal portion of a tapering section of the bone anchor than at a distal portion of the tapering section.

Some embodiments may further comprise a non-tapered section positioned at a distal end of the bone anchor, such as a portion having a cylindrical shape in cross section. In some embodiments, the non-tapered section may lack threads and/or comprise a sharp distal edge to facilitate bone penetration.

In an example of a bone anchor configured for engagement with a vertebral body according to other embodiments, the bone anchor may comprise an outer surface configured to engage vertebral bone and extending along a longitudinal axis of the bone anchor. The outer surface may taper, at least in part, from a proximal portion of the bone anchor to a distal portion of the bone anchor to define a wider bone anchor width at a proximal portion of a tapering section of the bone anchor than at a distal portion of the tapering section. The bone anchor may further comprise an inner chamber configured to engage and compact vertebral bone therein. The inner chamber may taper in a direction opposite a direction in which the outer surface tapers such that at least a portion of the inner chamber is wider at a distal portion of the inner chamber than an adjacent proximal portion of the inner chamber.

In some embodiments, the inner chamber may comprise an inner thread form and/or the outer chamber may comprise an outer thread form. In some embodiments, the inner thread form of the inner chamber may differ from the outer thread form of the outer chamber so as to provide a differential in force between forces generated by the outer thread form on vertebral bone adjacent to the outer thread form and forces generated by the inner thread form on vertebral bone within the inner chamber.

Some embodiments may further comprise a cylindrical section, which may, in some embodiments, form a distal tip of the bone anchor configured to facilitate penetration into a vertebral body.

In an example of a system for spinal deformity correction according to some embodiments, the system may comprise a first bone anchor configured to be engaged with a first vertebral body. The first bone anchor may comprise an outer thread form formed on an outer surface of the first bone anchor and an inner chamber. The inner chamber may comprise at least one of a plurality of bone engaging protrusions formed on an inner surface of the first bone anchor within the inner chamber and a profile that increases in cross-sectional area, at least in part, from a proximal end of the inner chamber to a distal end of the inner chamber. The system may further comprise a second bone anchor configured to be engaged with a second vertebral body. The second bone anchor may comprise an outer thread form formed on an outer surface of the second bone anchor and an inner chamber. The second bone anchor may further comprise at least one of a plurality of bone engaging protrusions formed on an inner surface of the second bone anchor within the inner chamber and a profile that increases in cross-sectional area, at least in part, from a proximal end of the inner chamber to a distal end of the inner chamber. The system may further comprise a tether extending between the first bone anchor and the second bone anchor. The tether may be configured to apply a corrective force to the first and second vertebral bodies.

In some embodiments, the inner chamber of the first and/or second bone anchors may each comprise a plurality of bone engaging protrusions, each plurality of bone engaging protrusions of which may comprise an inner thread form formed on an inner surface of its respective inner chamber.

In some embodiments, the inner chamber of the first and/or second bone anchors may each comprise a plurality of bone engaging protrusions, each plurality of bone engaging protrusions of which may comprise a plurality of bone engaging spikes formed on an inner surface of its respective inner chamber.

In some embodiments, the first and/or second bone anchors may each further comprise a removable engagement member configured to be coupled with its respective bone anchor so as to protrude away from the vertebral body within which the bone anchor is engaged. In some such embodiments, one or more of the removable engagement members may comprise a seat for receiving the tether.

In some embodiments, the inner chamber of one or both of the first and second bone anchors may comprise at least one stepped region in which a cross-sectional area of the respective inner chamber decreases in a distal to proximal direction by way of one of more steps, either with or without tapering portions.

In some embodiments, the outer thread form of one or both of the first and second bone anchors may comprise at least two distinct sections. In some such embodiments, a bone anchor sleeve may be configured to receive a respective inner bone anchor piece, and the at least two distinct sections of each bone anchor may comprise a first section configured to threadably engage its respective bone anchor sleeve and a second section configured to threadably engage the vertebral body to which the respective bone anchor is coupled.

In some embodiments, the bone anchor sleeve may be configured to engage the first bone anchor so as to provide a region outside of the inner chamber of the first bone anchor within which vertebral bone may be compressed during installation, such as a region formed in between an outer surface of the inner piece and an inner surface of the outer piece.

In an example of a method for applying a corrective force to a spinal column according to some implementations, the method may comprise advancing a first bone anchor into a first vertebral body of a spinal column and compacting cancellous bone within an inner chamber of the first bone anchor. The inner chamber preferably comprises at least one of a plurality of bone engaging protrusions and a profile that increases in cross-sectional area, at least in part, from a proximal end of the inner chamber to a distal end of the inner chamber. The method may further comprise advancing a second bone anchor into a second vertebral body of the spinal column and compacting cancellous bone within an inner chamber of the second bone anchor. Again, the inner chamber of the second bone anchor preferably comprises at least one of a plurality of bone engaging protrusions and a profile that increases in cross-sectional area, at least in part, from a proximal end of the inner chamber to a distal end of the inner chamber. A tether/ligament may be coupled between the first and second bone anchors to apply a force between the first and second bone anchors and thereby apply a corrective force to at least a portion of the spinal column.

In some implementations, the inner chamber of one or both of the bone anchors may comprise a plurality of bone engaging protrusions. In some such implementations, the step of compacting cancellous bone within the inner chamber(s) may comprise drawing cancellous bone into the inner chamber(s) with the plurality of bone engaging protrusions while the respective bone anchor is advanced into its corresponding vertebral body.

In some implementations, the first bone anchor may be offset from the second bone anchor relative to the spinal column such that the corrective force includes a derotational corrective component.

Some implementations may further comprise advancing a third bone anchor into the first vertebral body adjacent to the first bone anchor and/or advancing a fourth bone anchor into the second vertebral body adjacent to the second bone anchor such that two (or more) bone anchors are coupled with one or more of the vertebral bodies subject to corrective forces using the inventive assembly.

In some implementations, the first bone anchor may comprise a first protrusion extending transverse to a primary axis of the first bone anchor and the second bone anchor comprises a second protrusion extending transverse to a primary axis of the second bone anchor. The step of coupling a tether between the first and second bone anchors may then comprise, for example coupling a tether to the first protrusion and the second protrusion. Alternatively, fixed arms may be coupled with the first and second protrusions, which arms may be configured to be forced together by way of, for example, a ratchet mechanism, to apply forces to the bone anchors.

In some implementations and/or embodiments comprising the aforementioned protrusions, the first protrusion may extend in a direction at least substantially opposite from the second protrusion relative to the spinal column such that that the corrective force includes a derotational corrective component.

In another example of a method for applying a corrective force to a spinal column, the method may comprise advancing a first bone anchor into a first vertebral body of a spinal column while simultaneously redistributing and compacting vertebral bone into an inner chamber of the first bone anchor and advancing a second bone anchor into a second vertebral body of the spinal column while simultaneously redistributing and compacting vertebral bone into an inner chamber of the second bone anchor. A tether/ligament may then be coupled between the first and second bone anchors to apply a force between the first and second bone anchors and thereby apply a corrective force to at least a portion of the spinal column.

Some implementations may further comprise increasing tension on the tether/ligament to increase the force between the first and second bone anchors, which may be done, for example, by increasing a size of at least a portion of an engagement member coupled to at least one of the first and second bone anchors and within which at least a portion of the tether is positioned, decreasing a length of the tether, or decreasing a length of the tether, such as heat shrinking the tether.

Some implementations may further comprise tensioning the first and second bone anchors with a temporary tether having a non-fixed length followed by coupling the tether between the first and second bone anchors and then removing the temporary tether from being coupled with the first and second bone anchors.

The features, structures, steps, or characteristics disclosed herein in connection with one embodiment may be combined in any suitable manner in one or more alternative embodiments.

BRIEF DESCRIPTION OF THE DRAWINGS

The written disclosure herein describes illustrative embodiments that are non-limiting and non-exhaustive. Reference is made to certain of such illustrative embodiments that are depicted in the figures, in which:

FIGS. 11A-11D depict a variety of alternative means for tightening ligaments to engagement members coupled with bone anchors;

FIGS. 24A-24C depict various bone anchors having inner chamber sizes configured to accommodate distinct bone types;

FIG. 25 depicts another bone anchor having a removable cap/tether engagement member according to additional embodiments;

FIGS. 26A-26E depict various alternative configurations for bone anchor inner chambers;

FIG. 27A depicts a resizable ligament in a first configuration;

FIG. 27B depicts the resizable ligament in a second configuration for applying a corrective force to a bone anchor;

DETAILED DESCRIPTION

Figure 1A:
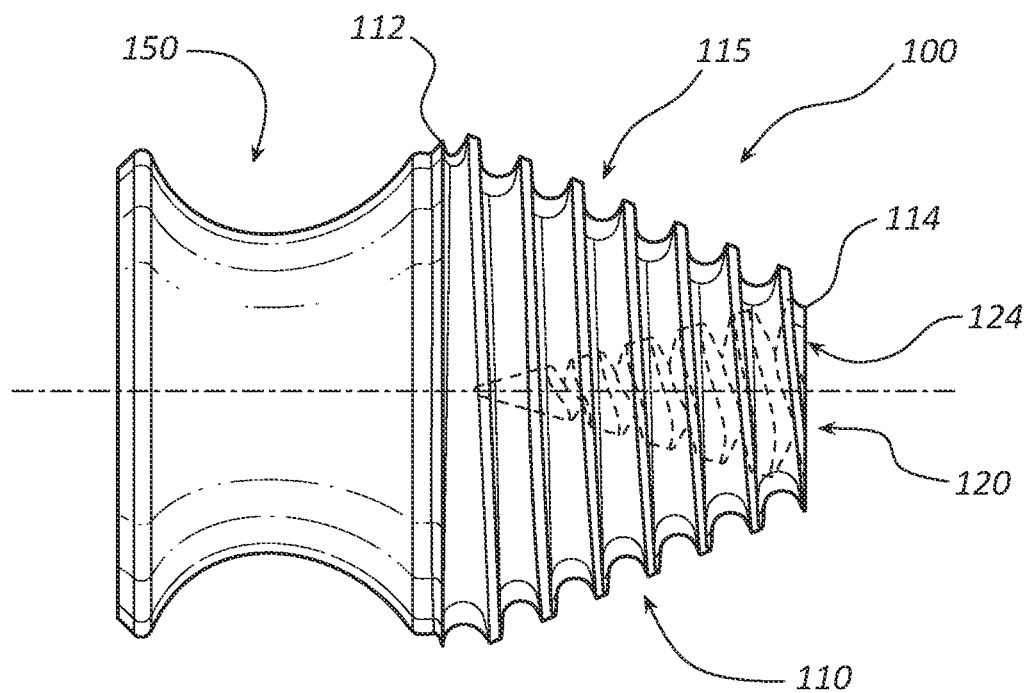
FIG. 1A is a perspective view of a vertebral bone anchor according to some embodiments.

It will be readily understood that the components of the present disclosure, as generally described and illustrated in the drawings herein, could be arranged and designed in a wide variety of different configurations. Thus, the following more detailed description of the embodiments of the apparatus is not intended to limit the scope of the disclosure but is merely representative of possible embodiments of the disclosure. In some cases, well-known structures, materials, or operations are not shown or described in detail.

As used herein, the term "substantially" refers to the complete or nearly complete extent or degree of an action, characteristic, property, state, structure, item, or result to function as indicated. For example, an object that is "substantially" cylindrical or "substantially" perpendicular would mean that the object/feature is either cylindrical/perpendicular or nearly cylindrical/perpendicular so as to result in the same or nearly the same function. The exact allowable degree of deviation provided by this term may depend on the specific context. The use of "substantially" is equally applicable when used in a negative connotation to refer to the complete or near complete lack of an action, characteristic, property, state, structure, item, or result. For example, structure which is "substantially free of" a bottom would either completely lack a bottom or so nearly completely lack a bottom that the effect would be effectively the same as if it completely lacked a bottom.

Similarly, as used herein, the term "about" is used to provide flexibility to a numerical range endpoint by providing that a given value may be "a little above" or "a little below" the endpoint while still accomplishing the function associated with the range.

The embodiments of the disclosure may be best understood by reference to the drawings, wherein like parts may be designated by like numerals. It will be readily understood that the components of the disclosed embodiments, as generally described and illustrated in the figures herein, could be arranged and designed in a wide variety of different configurations. Thus, the following detailed description of the embodiments of the apparatus and methods of the disclosure is not intended to limit the scope of the disclosure, as claimed, but is merely representative of possible embodiments of the disclosure. In addition, the steps of a method do not necessarily need to be executed in any specific order, or even sequentially, nor need the steps be executed only once, unless otherwise specified. Additional details regarding certain preferred embodiments and implementations will now be described in greater detail with reference to the accompanying drawings.

Figure 1B:
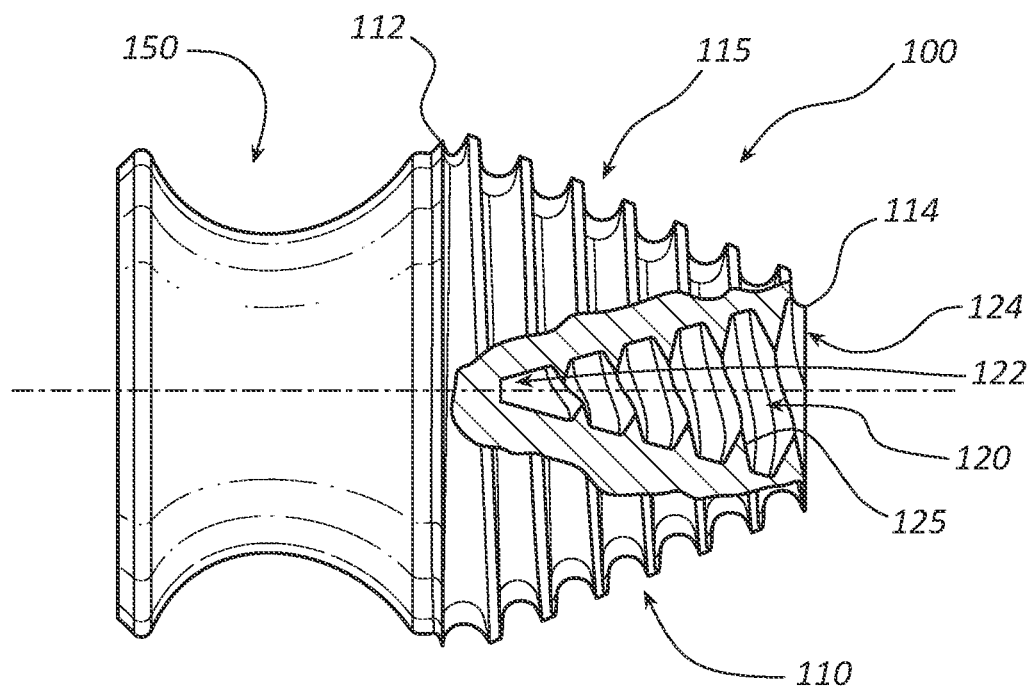
FIG. 1B is a cutaway, perspective view of the vertebral bone anchor of FIG. 1A.

FIGS. 1A and 1B depict an example of a bone anchor or implant 100 according to some embodiments. Bone anchor 100 comprises a bone engagement portion 110 that comprises an exterior surface that is tapered from the proximal end 112 to the distal end 114 such that the distal end 114 is narrower than the proximal end 112. In preferred embodiments, the angle of this taper may range from about 1 degree to about 20 degrees. In some such embodiments, the angle of this taper may range from about 5 degrees to about 10 degrees. In some embodiments, the exterior surface of the bone engagement portion of bone anchor 100 may define a conical or frusto-conical shape.

The exterior surface of bone engagement portion 110 further comprises a thread form 115, such as preferably a thread form having a relatively wide and/or deep thread configured for engagement with cancellous bone, such as the cancellous bone inside the cortical wall of a vertebrae. As discussed and, in some cases, depicted in connection with embodiments referenced below, such thread form 115 may comprise any suitable thread form, such as a single thread, a dual-lead thread, a triple-lead thread, and the like. As also discussed in greater detail below, in some embodiments, thread form 115 may vary throughout the form, such as by increasing and/or decreasing in pitch or depth from the proximal end 112 to the distal end 114.

Bone anchor 100 further comprises an inner chamber 120. Inner chamber 120 may be defined by an inner surface that, like the outer surface of bone engagement portion 110, also tapers. However, in preferred embodiments, inner chamber 120 tapers in the opposite direction relative to the outer surface of bone engagement portion 110. Thus, as shown in the cutaway view of FIG. 1B, chamber 120 tapers from its proximal end 122 to its distal end 124, which distal end 124 coincides with the distal end 114 of the entire bone engagement portion 110 in the depicted embodiment, such that the proximal end 122 of the inner chamber 120 is smaller in diameter and/or another suitable dimension than the distal end 124 of chamber 120. In preferred embodiments, the angle of this inner taper to chamber 120 may range from about 1 degree to about 20 degrees. In more preferred embodiments, the angle of this inner taper to chamber 120 may range from about 5 degrees to about 10 degrees.

Preferably, the length of the inner chamber 120 is greater than about 50% of the length of bone engagement portion 110 and/or thread form 115. In some embodiments, the length of the inner chamber 120 may be between about 10% and about 100% of the length of bone engagement portion 110 and/or thread form 115. In some such embodiments, the length of the inner chamber 120 may be between about 30% and about 100% of the length of bone engagement portion 110 and/or thread form 115. In some such embodiments, the length of the inner chamber 120 may be between about 50% and about 80% of the length of bone engagement portion 110 and/or thread form 115.

Inner chamber 120 is preferably configured to do one or more of actively engage and draw bone or other tissue into chamber 120, provide a differential in force and/or surface tension between the inner and outer surfaces of the implant, and compress the bone/tissue as it is being drawn into the chamber 120. The reverse taper of the inner chamber 120 previously discussed may provide for compression of the bone/tissue as it is introduced into the chamber by threading the exterior thread form 115 into the bony tissue.

As another possible feature that may serve to actively engage and draw bone or other tissue into chamber 120 and/or provide a differential in force and/or surface tension between the inner and outer surfaces of the implant 100, chamber 120 preferably also comprises a thread form 125. As with external thread form 115, internal thread form 125 may comprise any suitable thread form, such as a single thread, a dual-lead thread, a triple-lead thread, etc., and may vary along the form, such as by increasing and/or decreasing in pitch or depth from the proximal end 122 to the distal end 124. Internal thread form 125, along with any of the other similar thread forms disclosed herein, may terminate prior to the proximal end of the chamber 120 so as to provide an unthreaded chamber at the end. Similarly, the internal thread form 125 may vary from one location to another, such as by providing a tapering thread form, reversing direction, increasing or decreasing in depth, pitch, etc. For example, the internal thread form may, similar to the internal vs. external thread forms, comprise opposing forces and/or adjacent features that are opposed to one another to enhance bone compaction and/or provide other benefits.

In particularly preferred embodiments, thread form 115 may differ from thread form 125, which may further contribute to one or more of these features to improve functionality. For example, thread form 125 may comprise a different pitch, a different depth, a different number of leads, and/or a different thread type relative to thread form 115.

Other examples are providing a thread form 125 that varies in pitch and/or depth in a different direction, or to a different degree, relative to thread form 115. Again, this differential may contribute to a differential in force and/or tension that may improve bone healing, anchor stability, and/or provide other improvements. Although providing internal thread form 125 is preferred for these purposes, it is contemplated that, in alternative embodiments, inner chamber 120 may instead comprise other surface features, such as spikes, barbs, or other protrusions, grooves, and/or the like, that are configured to engage and/or draw in bone or other tissue. In some embodiments general surface roughening may even be useful for one or more of these purposes.

In certain preferred embodiments, thread form 125 has a greater thread depth along at least a portion of the thread form 125 (in some such embodiments, along the entire thread form 125) than the thread depth along at least a portion of thread form 115 (again, in some embodiments, along the entire thread form 115). In some such embodiments, for example, the depth of thread form 125 may be, along at least a portion thereof, between about 5 and about 50% greater than the depth of thread form 115 along at least a portion thereof. The depth of thread form 125 may vary, for example, between about 1 and about 5 mm in some embodiments.

Anchor 100 further comprises an engagement member 150 positioned at its proximal end. Engagement member 150 in the depicted embodiment comprises an annular groove that may be configured to engage a ligament or other flexible member that may also engage another anchor (not shown) to span multiple vertebrae and allow for introduction of a correctional force for correction of scoliosis or another spinal deformity. Of course, the annular groove shown in FIGS. 1A and 1B may be replaced with any of a variety of other engagement members available to those of ordinary skill in the art that would allow for application of a force between two or more anchors to apply such a correctional force using a ligament, rod, or other coupling member. Examples of such alternative engagement members include a tulip, clamp, post, hole, slot, and the like, some of which are discussed below in connection with other figures. Any of these engagement members, including engagement member 150, should be considered examples of means for engaging a ligament to impart a force to a vertebral body or other tissue or anatomical feature.

Figure 2A:
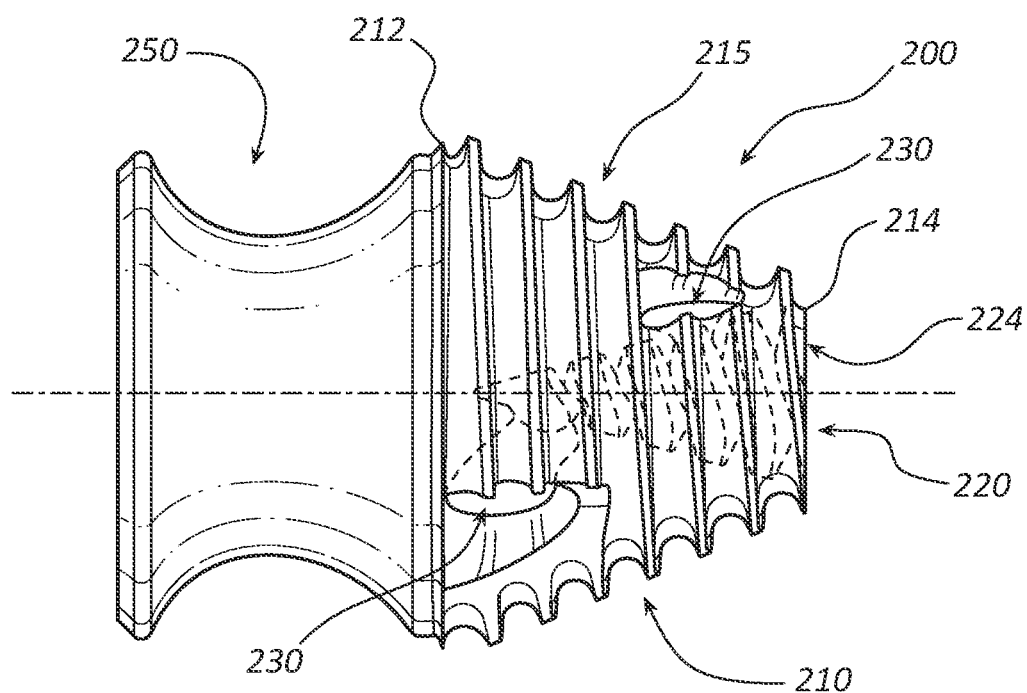
FIG. 2A is a perspective view of a vertebral bone anchor according to other embodiments.
Figure 2B:
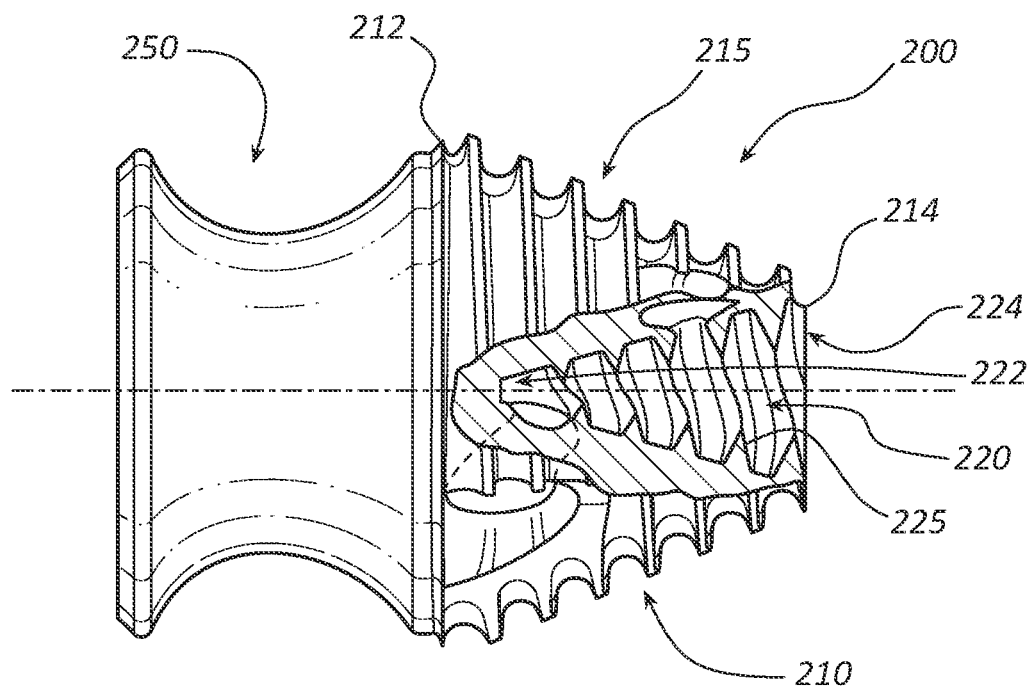
FIG. 2B is a cutaway, perspective view of the vertebral bone anchor of FIG. 2A.

FIGS. 2A and 2B depict another embodiment of an anchor 200. Like anchor 100, anchor 200 comprises a bone engagement portion having an exterior surface that is tapered from the proximal end 212 to the distal end 214 such that the distal end 214 is narrower than the proximal end 212. Similarly, the exterior surface of bone engagement portion further comprises a thread form 215. Again, in some embodiments, thread form 215 may vary throughout the form, such as by increasing and/or decreasing in pitch or depth from the proximal end 212 to the distal end 214.

Bone anchor 200 also further comprises an inner chamber 220 defined by an inner surface that tapers, preferably in an opposite direction relative to the outer surface of the bone engagement portion of anchor 200. The other dimensions, configurations, and options referenced above in connection with bone anchor 100 may also apply to bone anchor 200.

Thus, once again, inner chamber 220 is preferably configured to do one or more of actively engage and draw bone or other tissue into chamber 220, provide a differential in force and/or surface tension between the inner and outer surfaces of the anchor 200, and compress the bone/tissue as it is being drawn into the chamber 220, which may be accomplished by the reverse taper of the inner chamber and/or the internal thread form 225. As with thread forms 115/125, thread form 215 may differ from thread form 225, which may further contribute to one or more of these features to improve functionality.

In some embodiments, it may be desirable to create a force differential along one or more of the thread forms, such as, for example, by providing an external thread form that differs in pitch or otherwise along the length of the thread form. Similarly, it may be desirable to provide a force differential along the internal thread form by, for example, altering the internal thread form, by way of pitch, depth, etc., from one end of the thread form to the other, or by providing distinct, spaced apart thread forms on the inner and/or outer surfaces of the implant.

Anchor 200 further comprises an engagement member 250 defining an annular groove that may be configured to engage a ligament or other flexible member that may also engage another anchor (not shown) to span multiple vertebrae and allow for introduction of a correctional force for correction of scoliosis or another spinal deformity.

Unlike anchor 100, however, anchor 200 comprises a plurality of tunnels 230 and/or openings that extend from the exterior surface of anchor 200 to the inner chamber 220. These tunnels 230 may comprise sharpened and/or beveled edges to further facilitate drawing of bone material into chamber 220 as anchor 200 is advanced through a vertebral body.

Figure 3A:
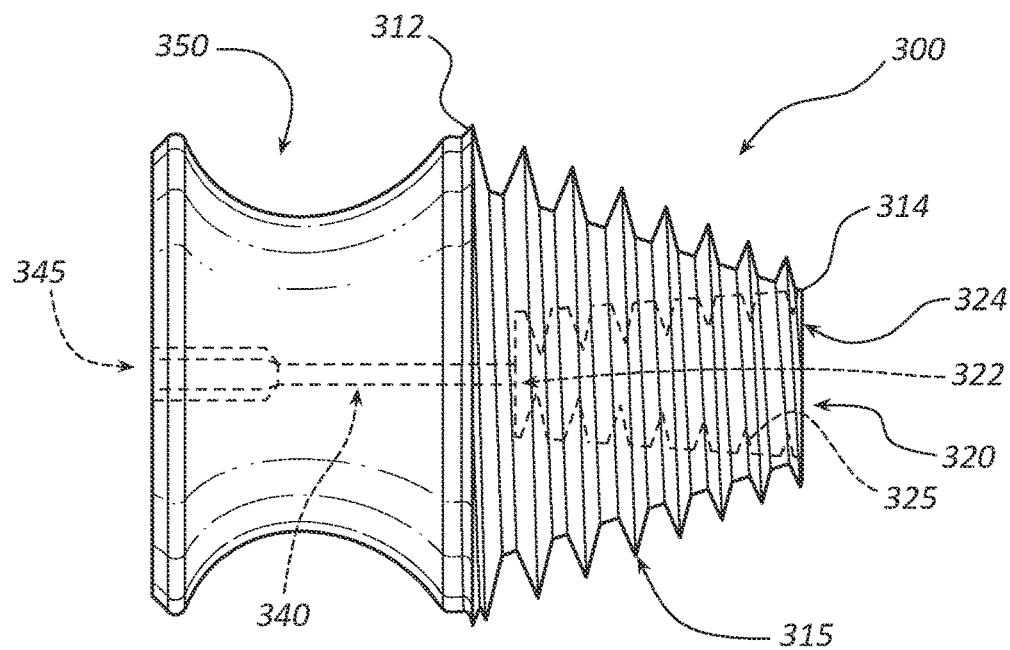
FIG. 3A is a perspective view of a vertebral bone anchor according to still other embodiments.

FIG. 3A depicts another embodiment of an anchor 300. Like anchors 100 and 200, anchor 300 again comprises a bone engagement portion comprising a thread form 315 and having an exterior surface that is tapered from the proximal end 312 to the distal end 314 such that the distal end 314 is narrower than the proximal end 312. Again, in some embodiments, thread form 315 may vary throughout the form, such as by increasing and/or decreasing in pitch or depth from the proximal end 312 to the distal end 314.

Bone anchor 300 also comprises an inner chamber 320 defined by an inner surface that tapers, preferably in an opposite direction relative to the outer surface of bone engagement portion. Chamber 320 is shown having a wider proximal end 322 than bone anchors 100 and 200. The other dimensions, configurations, and options referenced above in connection with bone anchors 100 and 200 may also apply to bone anchor 300.

Thus, once again, inner chamber 320 is preferably configured to do one or more of actively engage and draw bone or other tissue into chamber 320, provide a differential in force and/or surface tension between the inner and outer surfaces of the anchor 300, and compress the bone/tissue as it is being drawn into the chamber 320, which may be accomplished by the reverse taper of the inner chamber and/or the internal thread form 325. Once again, thread form 315 also preferably differs from thread form 325, which may further contribute to one or more of these features to improve functionality.

Anchor 300 further comprises an engagement member 350 defining an annular groove that may be configured to engage a ligament or other flexible member that may also engage another anchor (not shown) to span multiple vertebrae and allow for introduction of a correctional force for correction of scoliosis or another spinal deformity.

Unlike anchors 100 and 200, anchor 300 further comprises a channel 340 or cannulation that terminates in the proximal end of anchor 300. Channel 340 may be configured to receive a tool or portion of a tool and may facilitate introduction/implantation of anchor 300, such as a probe or guidewire. Thus, channel 340 may extend into chamber 320 so that a tunnel, which may be defined in part by channel 340 and in part by chamber 320, extends through the entire length of anchor 300 along its axis. In the depicted embodiment, a keyed tool recess 345 may be formed along the proximal portion of channel 340, which may be configured to receive a driver or other keyed male instrument for rotation/driving of anchor 300. Of course, in other embodiments, channel 340 need not extend the full length of anchor 300.

Figure 3B:
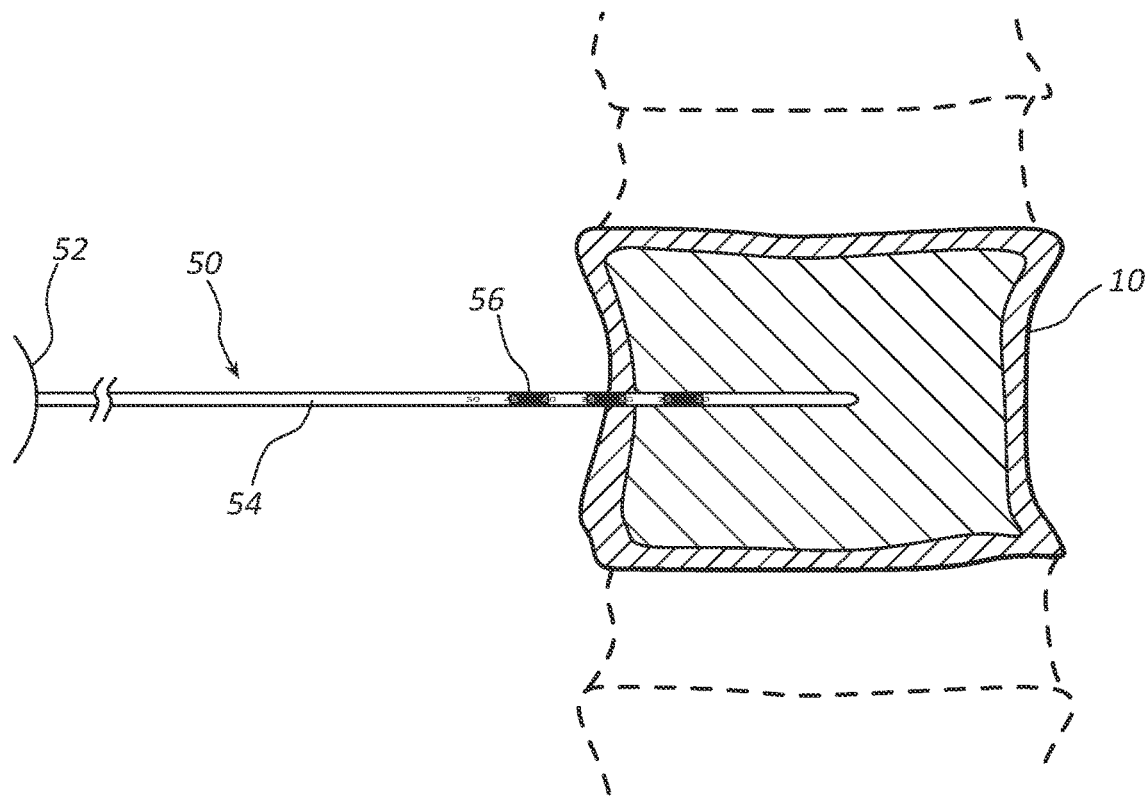
FIG. 3B is a cross-sectional view of a vertebral probe preparing a vertebral body for receipt of a bone anchor therein.

A preferred methodology for installing anchor 300 is depicted in FIGS. 3B-3E. Thus, as shown in FIG. 3B, a probe 50 may initially be inserted through the cortical wall of vertebral body 10 to establish a preferred path for insertion of anchor 300 therein. Probe 50 may comprise a handle or head 52 that, in some embodiments, may be removable from the shaft 54 of probe 50. In some such embodiments, head 52 may be slidably received over the proximal end of shaft 54 to allow for application of a distal force to insert probe 50 through the proximal cortical wall of vertebrae 10 but then allow for removal of head 52 by withdrawing head 52 proximally. In some embodiments, probe 50 may comprise a tip and/or other feature described in U.S. Provisional Patent Application No. 62/712,158, which was filed on Jul. 30, 2018 and titled "Vertebral Probes and Related Surgical Methods," which is hereby incorporated by reference herein in its entirety.

Shaft 54 may comprise a series of markings 56 configured to further facilitate ease of use, safety, and/or subsequent screw/anchor placement. More particularly, shaft 54 may comprise a series of alternating markings 56, which may include alphanumerical markings, dash lines, colors, patterns, etc. In some embodiments, a series of adjacent sections comprising distinct markings of one or more types may be provided. By varying the sections in this manner, a surgeon may be provided with a more general view, once the surgeon becomes familiar with the marking system, of the probe 50 placement without having to rely on specific alphanumerical markings. Of course, those of ordinary skill in the art will appreciate a variety of alternative configurations to allow a surgeon to visualize an approximate location of a vertebral probe within a vertebral body without requiring precise numerical measurements and/or tick marks/dash lines.

Figure 3C:
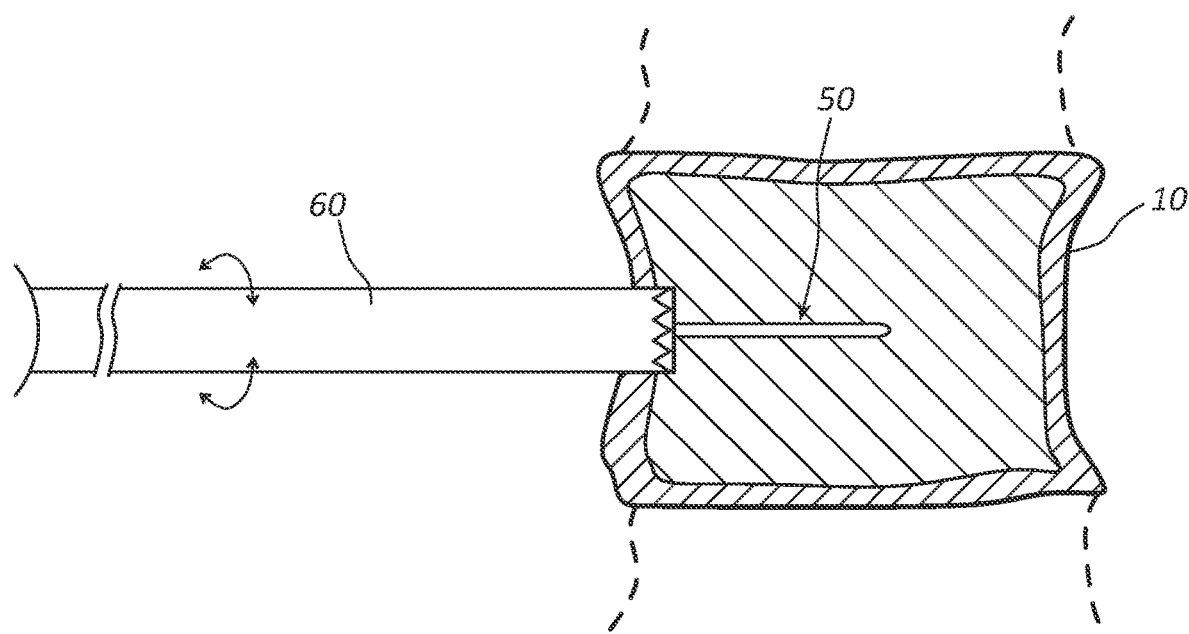
FIG. 3C is a cross-sectional view of a tap that may be slidably received over the vertebral probe or a guidewire to create a starter hole and/or otherwise further prepare the vertebral body for receipt of the bone anchor.

After establishing a desired path within vertebrae 10, head 52 may be removed and, in some embodiments and implementations, a secondary tool, such as a bone screw tap 60 comprising a central opening configured to receive shaft 54 of probe 50, may be inserted over probe 50. Tap 60 or another suitable instrument may comprise a distal end having a series of teeth, spikes, threads, or the like to create a divot or starter hole to facilitate insertion of the anchor 300, as shown in FIG. 3C. In some embodiments, the instrument may comprise a rounded tip, a beveled tip, or a tip having a sharp and/or pointed distal end.

Figure 3D:
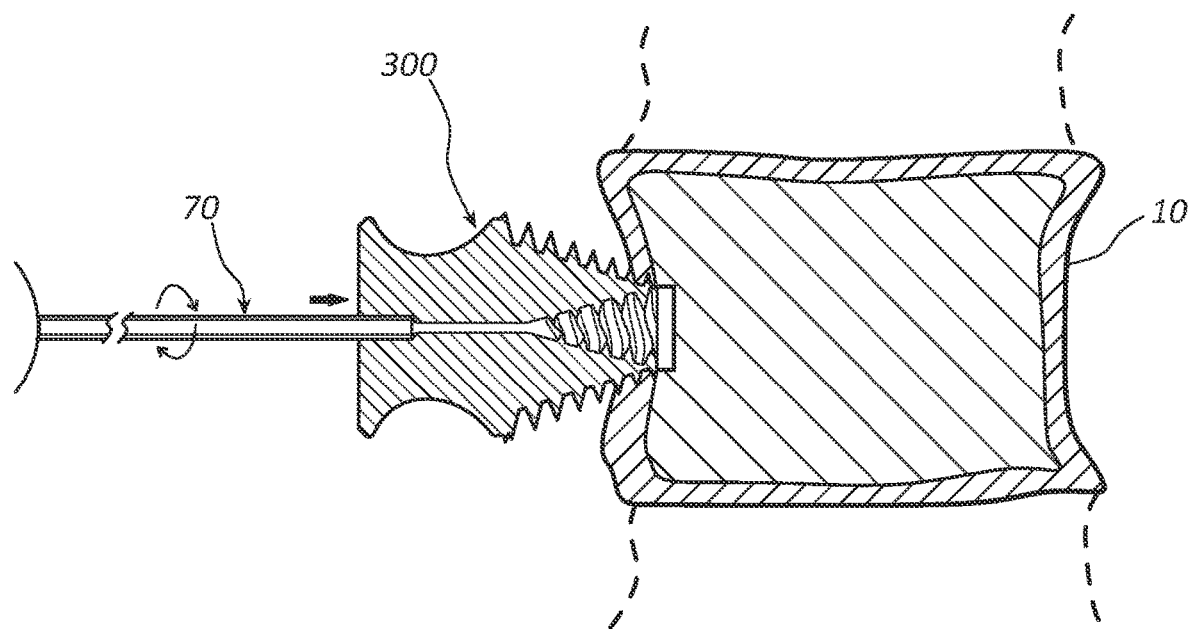
FIG. 3D is a cross-sectional view of the bone anchor of FIG. 3A being inserted into the vertebral body.
Figure 3E:
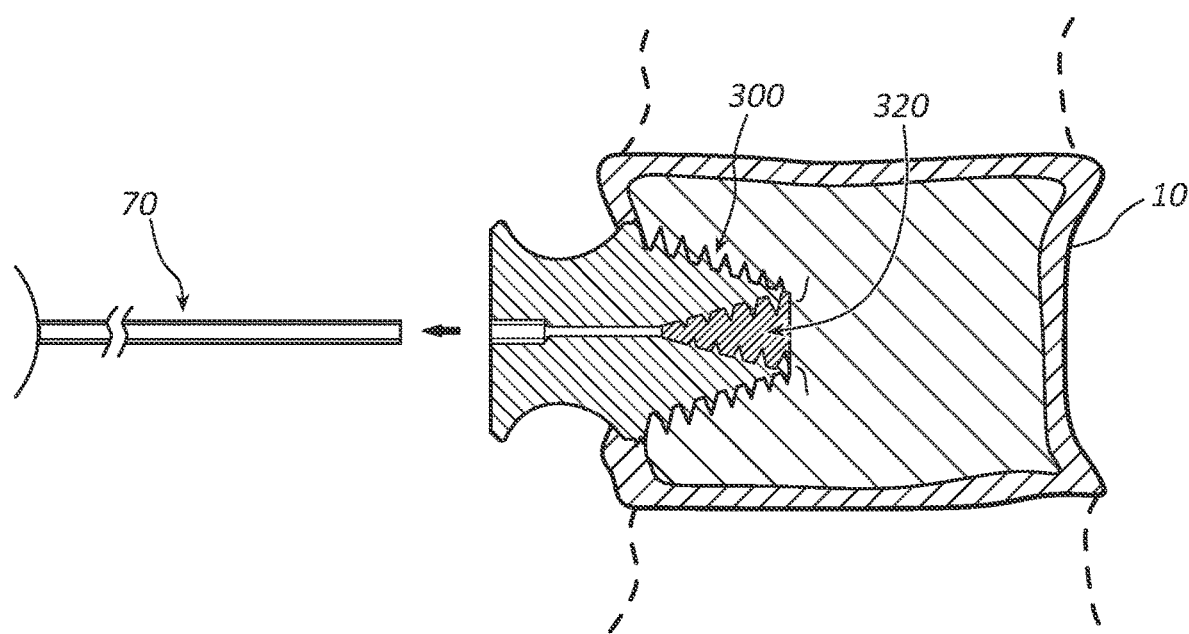
FIG. 3E is a cross-sectional view following insertion of the bone anchor of FIG. 3A into the vertebral body.

Following sufficient preparation of receipt for anchor 300, bone screw tap 60 may be removed from probe 50 (or a guidewire) and anchor 300 may be advanced into place adjacent to the prepared bone entry site over probe 50 or a guidewire (not shown). As shown in FIG. 3D, anchor 300 may then be rotated and/or driven into the vertebrae 10. In some embodiments and implementations, probe 50 may comprise a keyed portion configured to engage keyed recess 345 of anchor 300 such that this device may also be used to drive the anchor. Alternatively, another driver or suitable device may be used for this purpose, such as driver 70 shown in FIG. 3D. Thus, in some embodiments and implementations, probe 50 may be removed prior to advancing anchor 300. As shown in FIG. 3E, as implant 300 is driven into vertebrae 10, bone is received and automatically compacted within chamber 320 due to the features previously discussed, including the reverse taper of chamber 320.

Figure 4A:
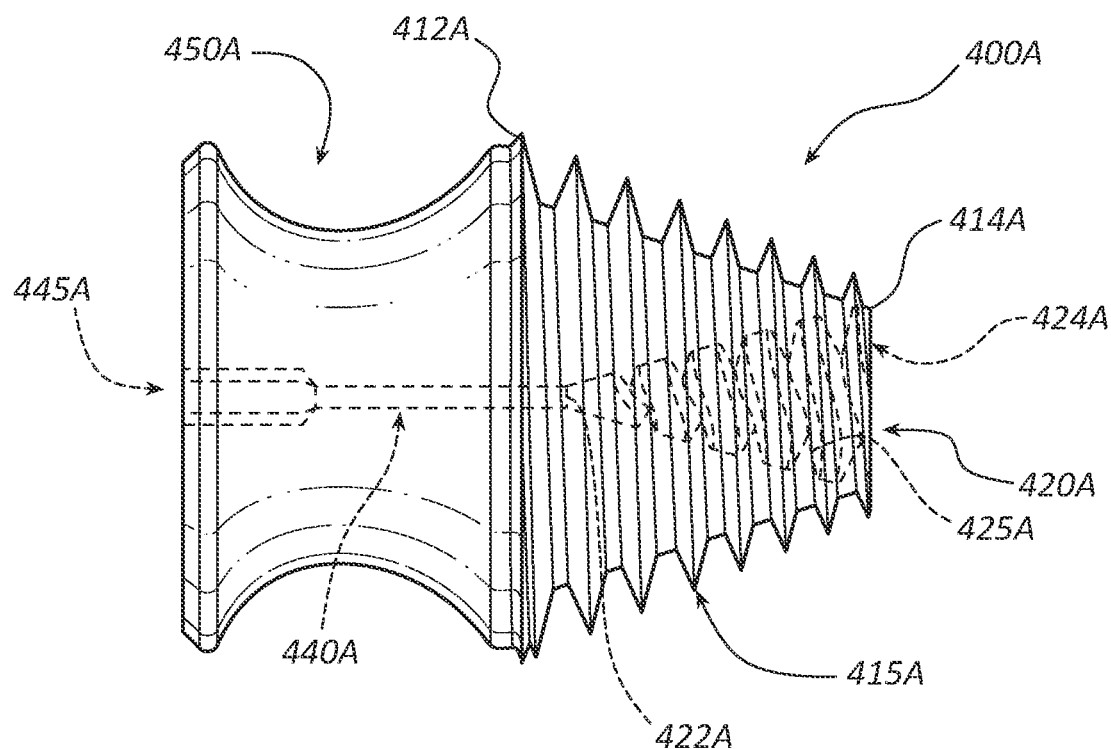
FIG. 4A is a perspective view of a vertebral bone anchor according to still other embodiments.
Figure 4B:
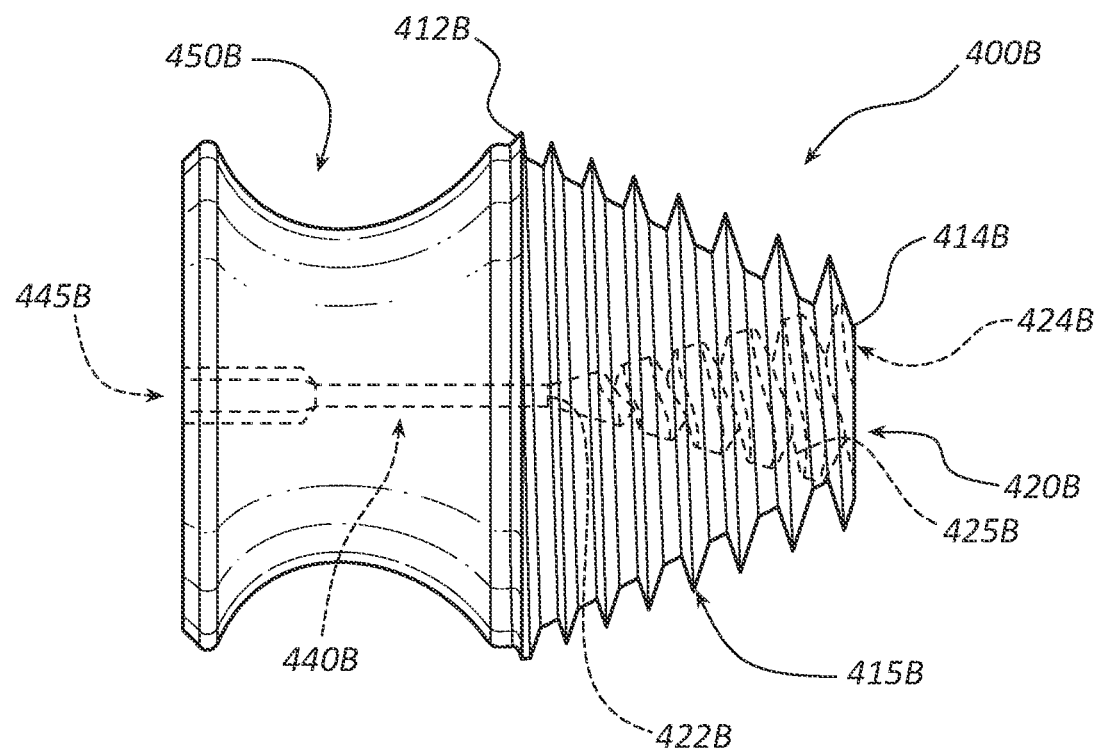
FIG. 4B is a perspective view of a vertebral bone anchor according to further embodiments.

Still other embodiments of bone anchors are shown in FIGS. 4A and 4B at 400A and 400B, respectively. Bone anchors 400A and 400B are similar to the previous bone anchors discussed in connection with previous figures except thread forms 415A/415B gradually differ in thread depth between the proximal ends 412A/412B and the distal ends 414A/414B of their respective anchor. More particularly, thread form 415A defines a thread depth that decreases from the proximal end 412A to the distal end 414A and thread form 415B defines a thread depth than increases from the proximal end 412B to the distal end 414B.

These bone anchors 400A/400B are otherwise similar to the anchors previously discussed and may include, or be modified to omit, any of the features discussed in connection with such anchors. Thus, bone anchors 400A/400B both comprise an inner chamber 420A/420B that preferably tapers in the opposite direction as the exterior surface of the bone engagement portion of the anchor 400A/400B upon which the thread forms 415A/415B are formed such that the proximal portions 422A/422B are smaller in diameter or another dimension than the distal portions 424A/424B, as previously mentioned. In addition, bone anchors 400A/400B further comprise respective second thread forms 425A/425B within chambers 420A/420B, engagement members 450A/450B for engaging ligaments or other engagement bands, a central cannulation 440A/440B, and a keyed feature 445A/445B to facilitate engagement with a driver or other suitable instrument for driving the anchor into a vertebral body or other tissue.

Figure 5A:
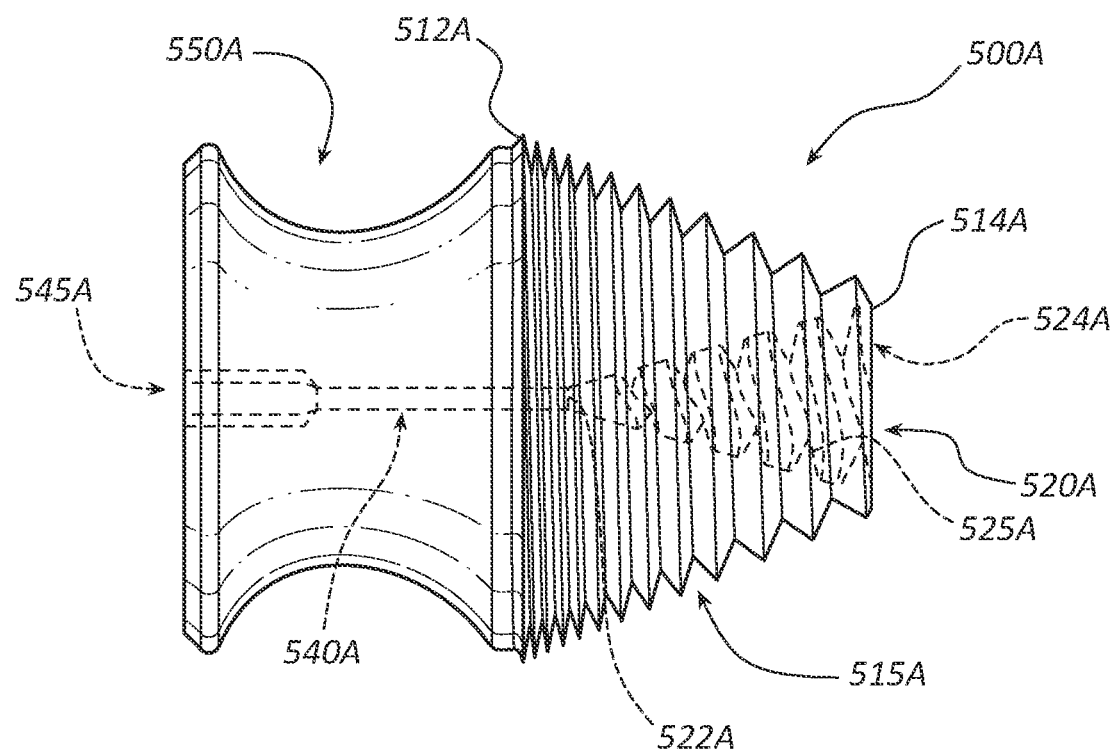
FIG. 5A is a perspective view of a vertebral bone anchor according to still further embodiments.
Figure 5B:
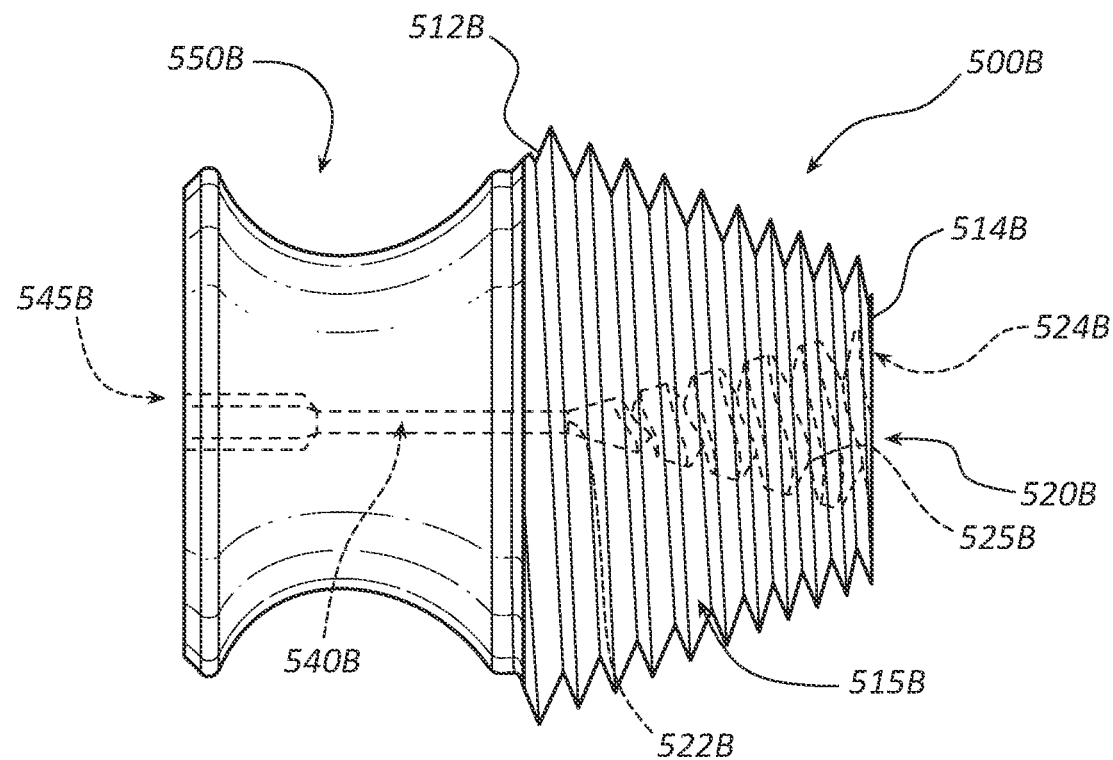
FIG. 5B is a perspective view of a vertebral bone anchor according to additional embodiments.

Additional embodiments of bone anchors are shown in FIGS. 5A and 5B at 500A and 500B, respectively. Once again, bone anchors 500A and 500B are similar to the previous bone anchors depicted except thread forms 515A/515B gradually differ in thread pitch between the proximal ends 512A/512B and the distal ends 514A/514B of a bone engagement region of their respective anchor. More particularly, thread form 515A defines a thread pitch that increases from the proximal end 512A to the distal end 514A and thread form 515B defines a thread pitch than decreases from the proximal end 512B to the distal end 514B.

These bone anchors 500A/500B are otherwise similar to the anchors previously discussed and may include, or be modified to omit, any of the features discussed in connection with such anchors. Thus, bone anchors 500A/500B both comprise an inner chamber 520A/520B that preferably tapers in the opposite direction as the exterior surface of the bone engagement portion of the anchor 500A/500B upon which the thread forms 515A/515B are formed. In addition, bone anchors 500A/500B further comprise respective second, internal thread forms 525A/525B within chambers 520A/520B. These internal thread forms 525A/525B preferably differ in one or more ways relative to external thread forms 515A/515B, such as by providing an increased thread depth, differing pitch, etc. The internal thread forms 525A/525B may also vary between their respective proximal and distal ends, similar to the external thread forms 515A/515B.

Bone anchors 500A/500B further comprise engagement members 550A/550B for engaging ligaments or other engagement bands, a central cannulation 540A/540B, and a keyed feature 545A/545B to facilitate engagement with a driver or other suitable instrument for driving the anchor into a vertebral body or other tissue.

Figure 6:
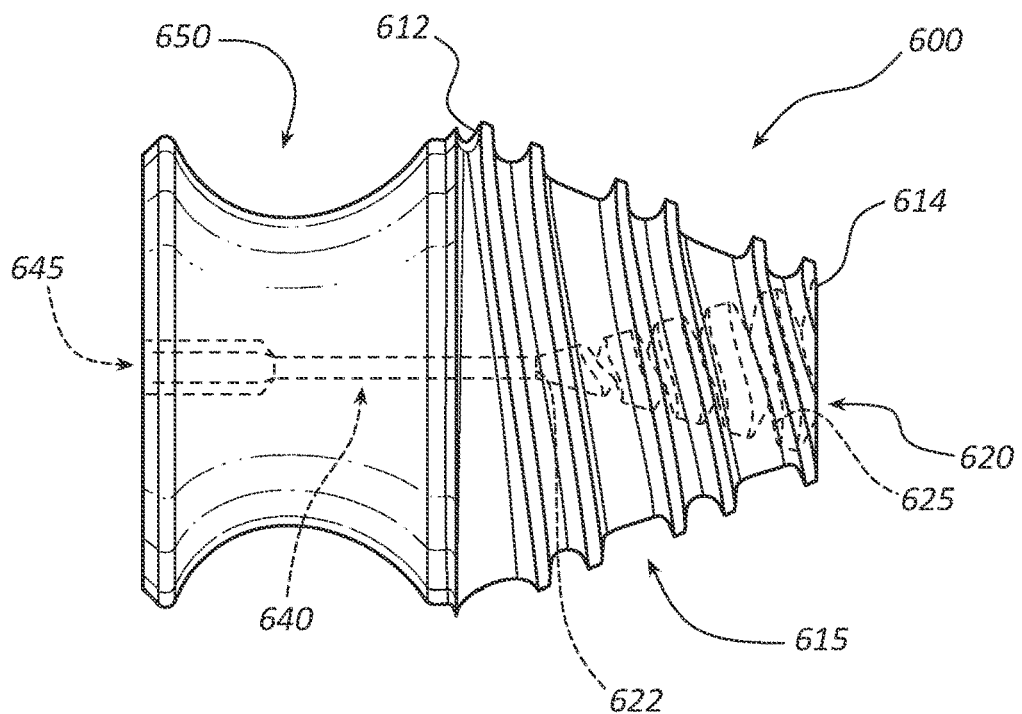
FIG. 6 is a perspective view of a vertebral bone anchor according to still other embodiments.

Yet another alternative embodiment of a bone anchor 600 is depicted in FIG. 6. Bone anchor 600 comprises an external thread form 615 that comprises a dual-lead thread form. Other embodiments may comprise a triple lead thread form. Again, one or more of the previously described features may be included as desired, including an internal chamber 620 comprising an internal thread form 625. Internal thread form 625 may comprise a single, double, or triple lead thread form, or any other suitable thread form. Again, in certain preferred embodiments, internal thread form 625 may differ from external thread form 625 in one or more ways in order to provide a differential in force and/or surface tension between various portions of the anchor 600, such as between the inner and outer surfaces of the implant 600. In the depicted embodiment, anchor 600 further comprises an engagement member 650, a central cannulation for a guide wire, probe, or other instrument, and a keyed feature 645.

Figure 7A:
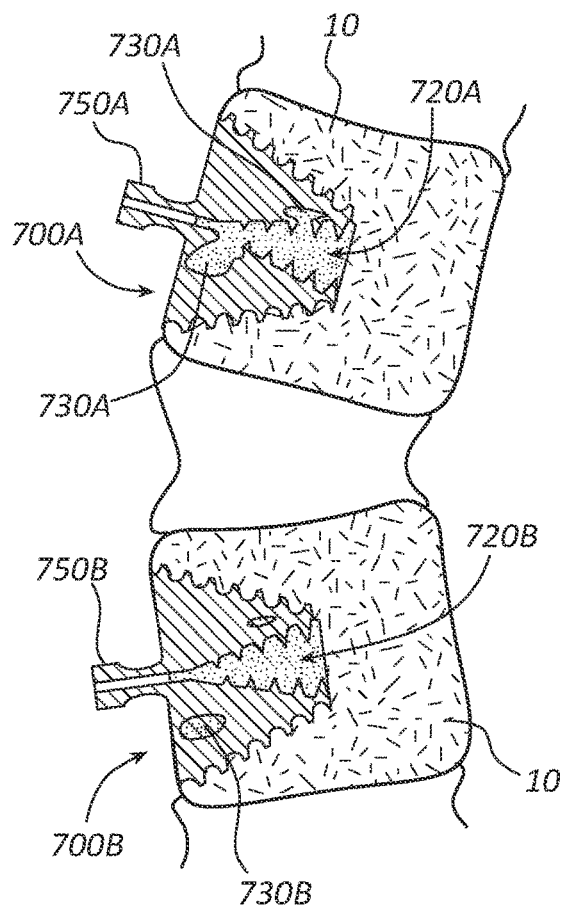
FIG. 7A is a cross-sectional view of a system for spinal deformity correction according to some embodiments shown prior to application of a restorative force via ligaments.
Figure 7B:
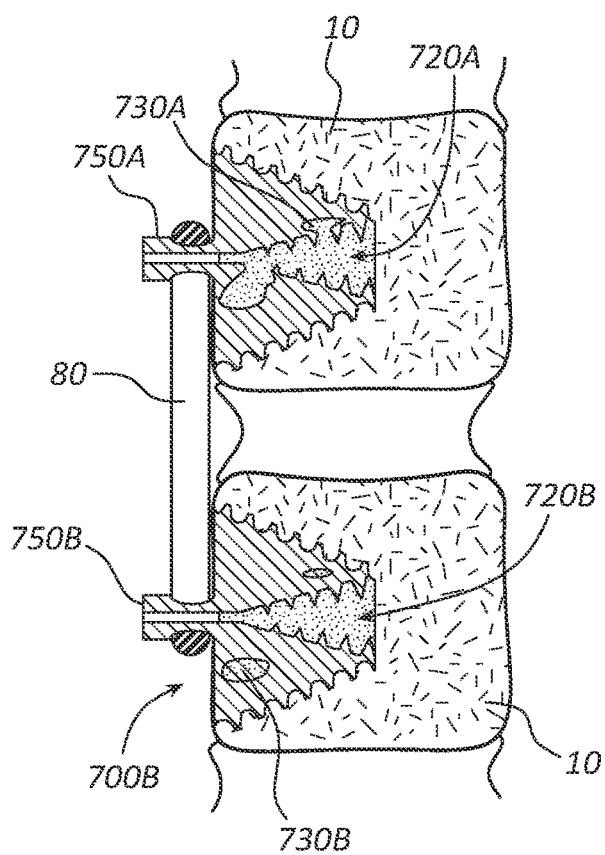
FIG. 7B is a cross-sectional view of a system for spinal deformity correction according to some embodiments shown following application of a restorative force via ligaments.

FIGS. 7A and 7B depict a system for spinal deformity correction comprising two bone anchors 700A/700B each coupled with an adjacent vertebral body 10. As those of ordinary skill in the art will appreciate, any number of bone anchors may be used as desired in accordance with the particular surgical procedure being performed. As shown in FIG. 7B, a loop ligament 80 may be wrapped around respective engagement members 750A/750B of the adjacent anchors 700A/700B to apply a restorative force to a patient's spinal column. Various additional elements, features, and/or methods may be used to increase and/or decrease this force as needed, some of which are discussed below.

As also shown in these figures, bone anchors 700A/700B may each comprise one or more tunnels 730A/730B that may allow for driving additional bone material into inner chambers 720A/720B, as previously described. These tunnels 730A/730B may also allow for an outlet to the pressure that may build up within chambers 720A/720B as bone anchors 700A/700B are driven through the vertebral bone.

Figure 8:
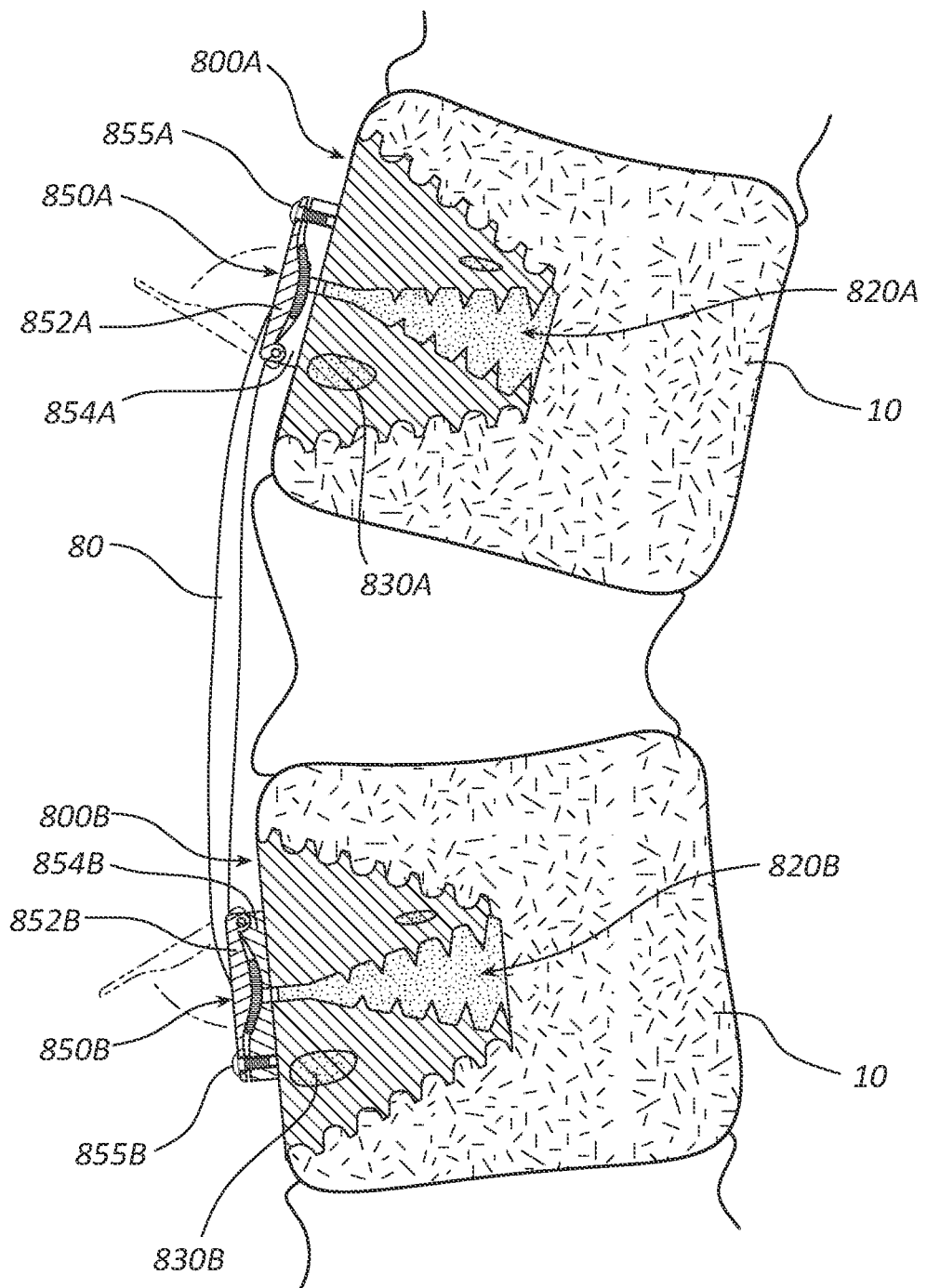
FIG. 8 is a cross-sectional view of a system for spinal deformity correction according to other embodiments.

FIG. 8 depicts still another embodiment of a system for spinal deformity correction. This system again comprises two adjacent bone anchors 800A/800B. These bone anchors 800A/800B again preferably comprise inner chambers 820A/820B that comprise thread forms that may differ from the respective exterior thread forms. Also, one or more tunnels 830A/830B and/or other openings may be formed between the exterior of the bone anchors 800A/800B and the interior of the bone anchors 800A/800B, such as between the inner thread forms and the outer thread forms.

Bone anchors 800A/800B each comprises a distinct type of engagement member 850A/850B. More particularly, engagement members 850A/850B each comprises a clamp defined by a base 854A/854B and a lid 852A/852B that is pivotably coupled to base 854A/854B. A fastener 855A/855B may be used to fix the ligament 80, which may comprise a straight (non-loop) ligament). Thus, the ligament 80 may be clamped at one end or position (associated with one of the two bone anchors 800A/800B) and then inserted through the other clamp/engagement member 850, after which a desired force may be applied to the associated vertebral bodies through ligament 80 and then the opposite end or position may be clamped using the other clamp/engagement member 850.

Preferably, the inner surface of the lid 852 and seat/base 854 are smooth and define a large surface area so as to distribute the force applied to the ligament 80 along a large surface area of the ligament to avoid damage to the ligament 80, as shown in FIG. 8. In some embodiments, clamping force may be applied gradually to ligament 80 so that ligament 80 may be partially clamped using a first force sufficient to keep the ligament in place but allow the ligament 80 to be pulled through engagement members 850A/850B upon application of a threshold larger force. Thus, ligament 80 may be pulled through the clamp defined by the lid 852 and base 854 and then fastener 855 may be further tightened to apply a second, larger locking force that locks the two anchors 800 in place with the desired restoration force. In some embodiments, non-circular ligaments, such as ovoid ligaments, may be used to further enhance this effect if desired. Engagement members 850A and 850B are additional examples of means for engaging a ligament to impart a force to a vertebral body or other tissue or anatomical feature.

Figure 9:
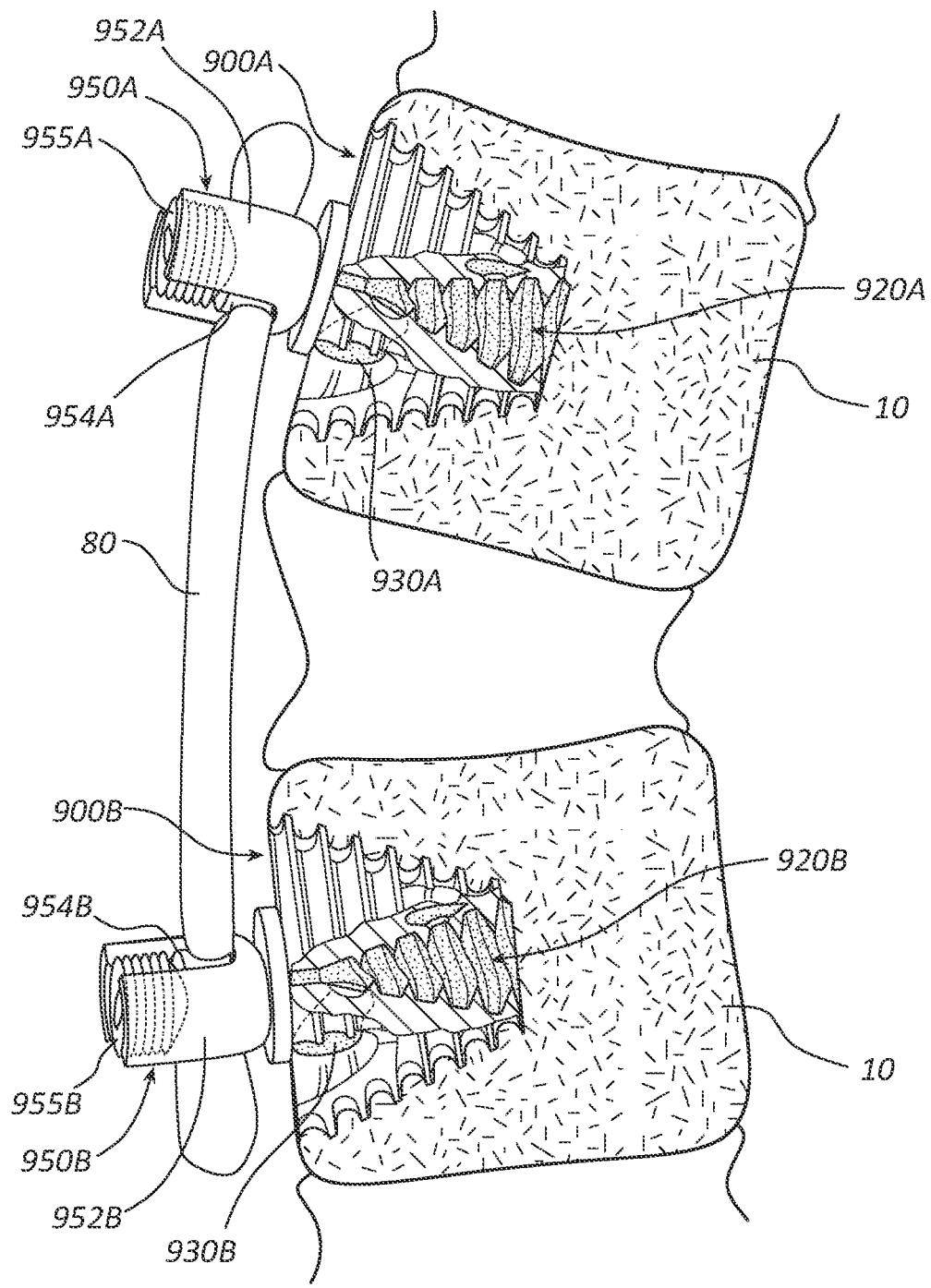
FIG. 9 is a perspective, cutaway view of a system for spinal deformity correction according to still other embodiments.

FIG. 9 depicts yet another embodiment of a system for spinal deformity correction. This system again comprises two adjacent bone anchors 900A/900B that may comprise, or lack if desired, any of the aforementioned features and/or other features available to those of ordinary skill in the art. Thus, bone anchors 900A/900B preferably comprise inner chambers 920A/920B that comprise thread forms that may differ from the respective exterior thread forms, as previously discussed. Also, one or more tunnels 930A/930B and/or other openings may be formed between the exterior of the bone anchors 900A/900B and the interior of the bone anchors 900A/900B, such as between the inner thread forms and the outer thread forms.

Bone anchors 900A/900B each comprises another distinct type of ligament engagement member 950A/950B. More particularly, engagement members 950A/950B each comprises a tulip connector 952A/952B comprising a U-shaped channel configured to receive a ligament 80 or another suitable, preferably flexible, coupling member. Engagement members 950A/950B each further comprises a set screw or cap 955A/955B that is configured to lock the ligament 80 in place within the tulip connector 952A/952B. Due to the flexible nature of the preferred ligaments 80, it may also be desired to provide an intermediary element between the cap 955A/955B and the ligament. Thus, in the depicted embodiment, a saddle 954A/954B is provided. Saddle 954A/954B is configured to distribute the force from the cap 955A/955B about a larger surface area of ligament 80 so as to reduce the possibility of unwanted damage to ligament 80. Notwithstanding the preferable for providing a larger, smoother surface area to reduce damage, it is contemplated that a set screw may be configured to directly contact and lock ligament 80 in place in alternative embodiments.

In some embodiments, the force on ligament 80 may be applied gradually to so that ligament 80 may be partially clamping using a first force sufficient to keep the ligament in place but allow the ligament 80 to be pulled through engagement members 950A/950B upon application of a threshold larger force. Thus, ligament 80 may be pulled through one of the tulip connectors 950 and partially tightened and then later may be further tightened to apply a second, larger locking force that locks the two anchors 900 in place with the desired restoration force. Engagement members 950A and 950B are additional examples of means for engaging a ligament to impart a force to a vertebral body or other tissue or anatomical feature.

Figure 10A:
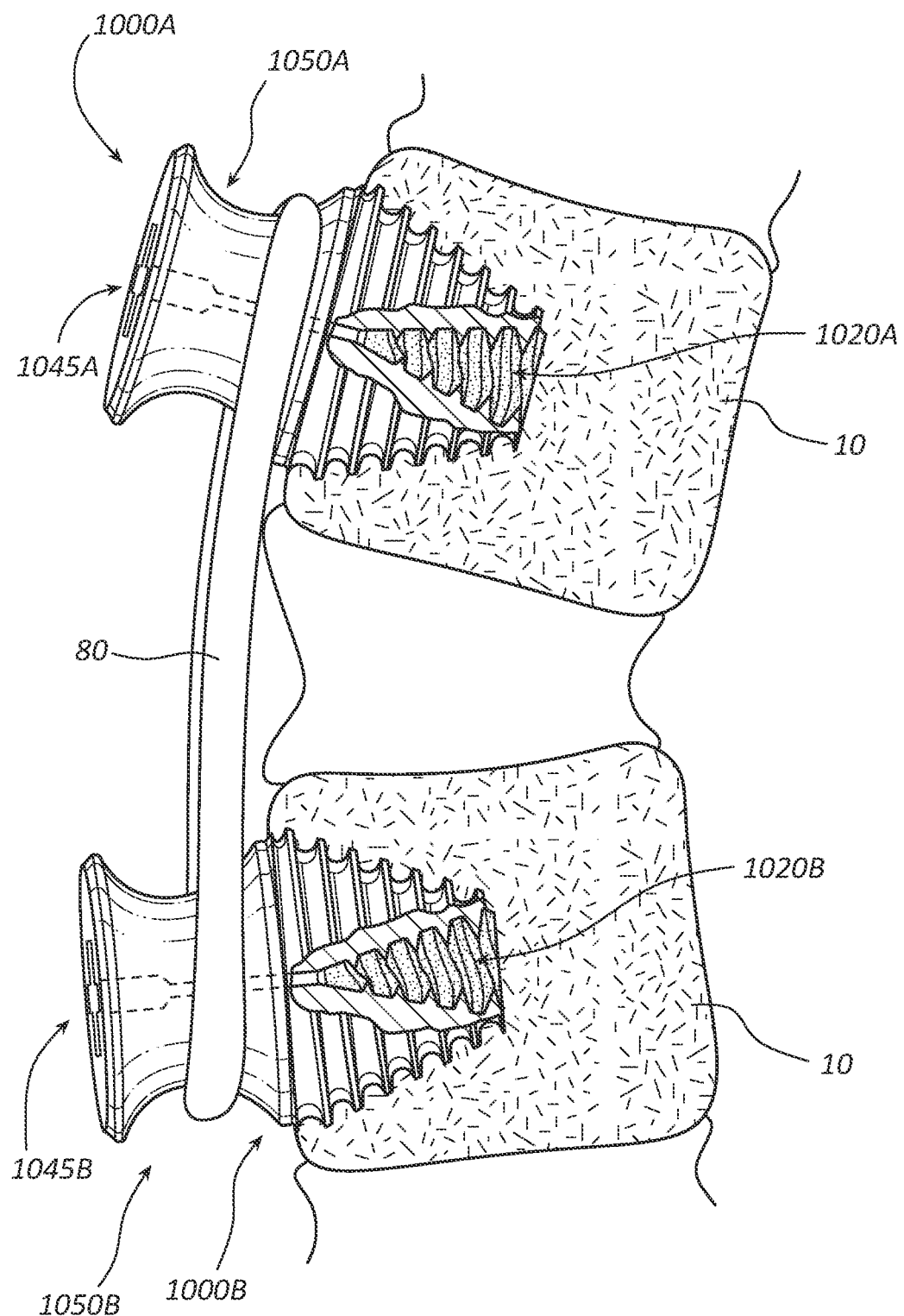
FIG. 10A is a perspective, cutaway view of a system for spinal deformity correction according to further embodiments.
Figure 10B:
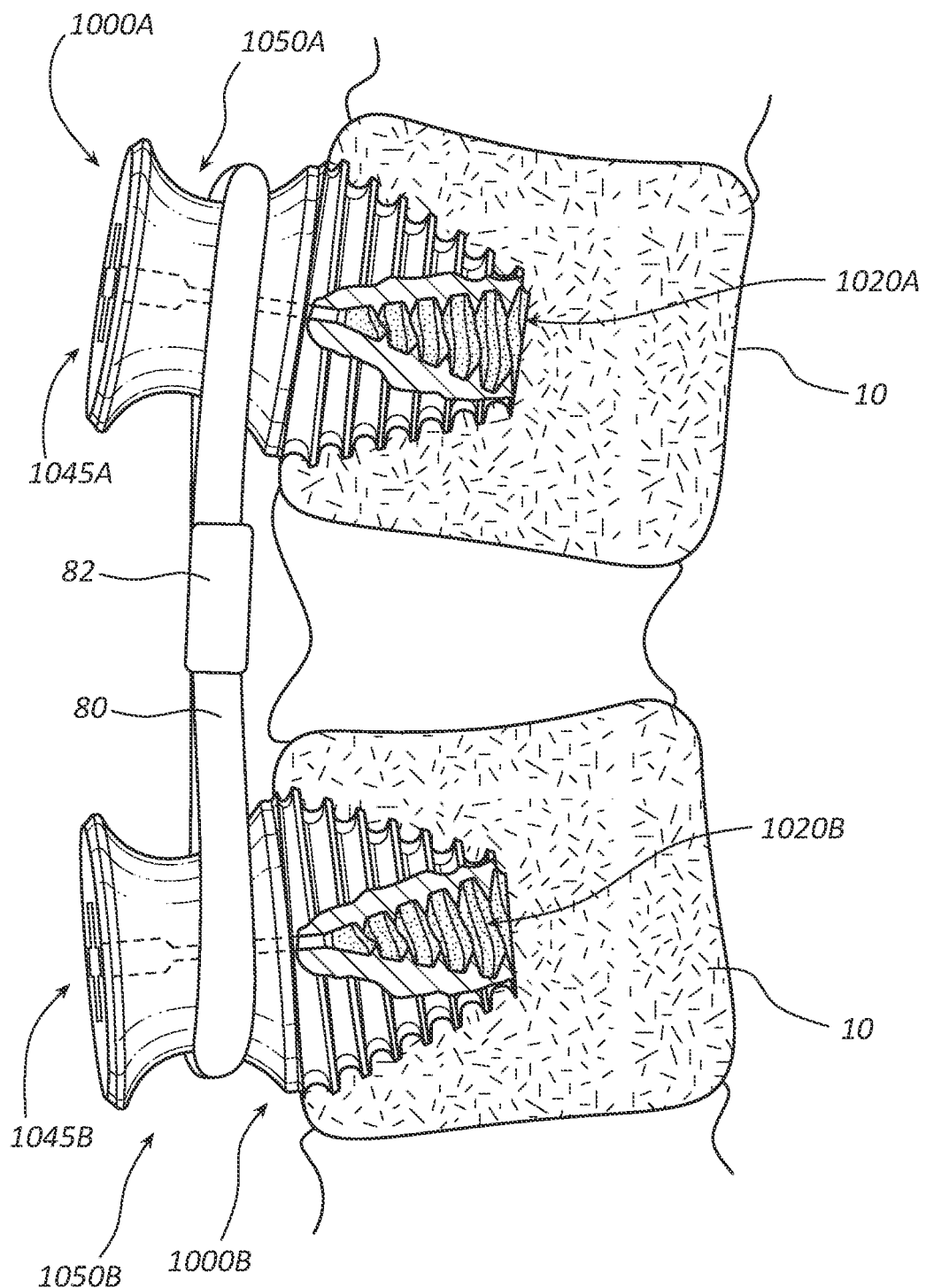
FIG. 10B is a perspective, cutaway view of the system for spinal deformity correction of FIG. 10A following tightening of a loop ligament coupled with two adjacent bone anchors.

FIGS. 10A and 10B depict another embodiment of a system for spinal deformity correction. This system again comprises two or more adjacent bone anchors 1000A/1000B that may comprise, or lack if desired, any of the aforementioned features and/or other features available to those of ordinary skill in the art. Thus, bone anchors 1000A/1000B preferably comprise inner chambers 1020A/1020B that comprise thread forms that may differ from the respective exterior thread forms, as previously discussed. Keyed recesses 1045A/1045B may be provided in a proximal surface of anchors 1000A/1000B to facilitate driving the anchors 1000A/1000B into vertebral bodies 10, as previously discussed.

A loop ligament 80 may be wrapped around respective engagement members 1050A/1050B, as depicted in FIG. 10A. One or more sutures, bands, or other tightening means 82 may then be used to increase the force between anchors 1000A/1000B to apply a restorative force to a spinal column, as depicted in FIG. 10B. As those of ordinary skill in the art will appreciate, any number of such tightening means 82 may be provided as desired to apply forces gradually until the full restorative force desired has been applied.

FIGS. 11A-11D depict various alternative system for spinal deformity correction. Each of the depicted embodiments may comprise similar anchors, including any of the aforementioned bone anchors. Each of the depicted embodiments may further comprise similar engagement members 1150A/1150B that are coupled to the anchors, such as to a proximal end of the anchors, to facilitate application of a restorative or other desired force. However, the systems depicted in these figures comprise a variety of distinct means for increasing the force between adjacent anchors.

For example, FIG. 11A depicts a loop ligament 80 that is wrapped around adjacent anchors in a figure-8 manner. Thus, the ligament may be coupled to one of the anchors and then rotated any number of times as desired according to the desired force to be applied before being coupled to the opposite anchor.

FIG. 11B depicts a system including a means for increasing the force between adjacent anchors that is similar to that depicted in FIG. 10B. Thus, a band 82 may be wrapped around loop ligament 80 at a desired location between adjacent anchors. Band 82 may vary in size according to the desired force to be applied or, as previously mentioned, a plurality of such bands 82 may be used to adjust the force to any desired level.

FIG. 11C depicts a straight ligament 80 that may be inserted at opposite ends within a means 85 for increasing the force between adjacent anchors that may comprise, for example, an internal ratchet mechanism that may allow for one end of ligament to be pulled through mechanism 85 to shorten the loop defined thereby without allowing this end to be retracted.

Similarly, FIG. 11D depicts a pair of straight ligaments 80A/80B that may be inserted at opposite ends within another example of a means for increasing the force between adjacent anchors 85. The means 85 for increasing the force depicted in FIG. 11D may allow for one of either of the two opposite ends of ligaments 80A/80B to be pulled through the internal ratcheting mechanism to decrease the length of the defined loop and thereby increase the force being applied to whatever degree of precision required.

Figure 12A:
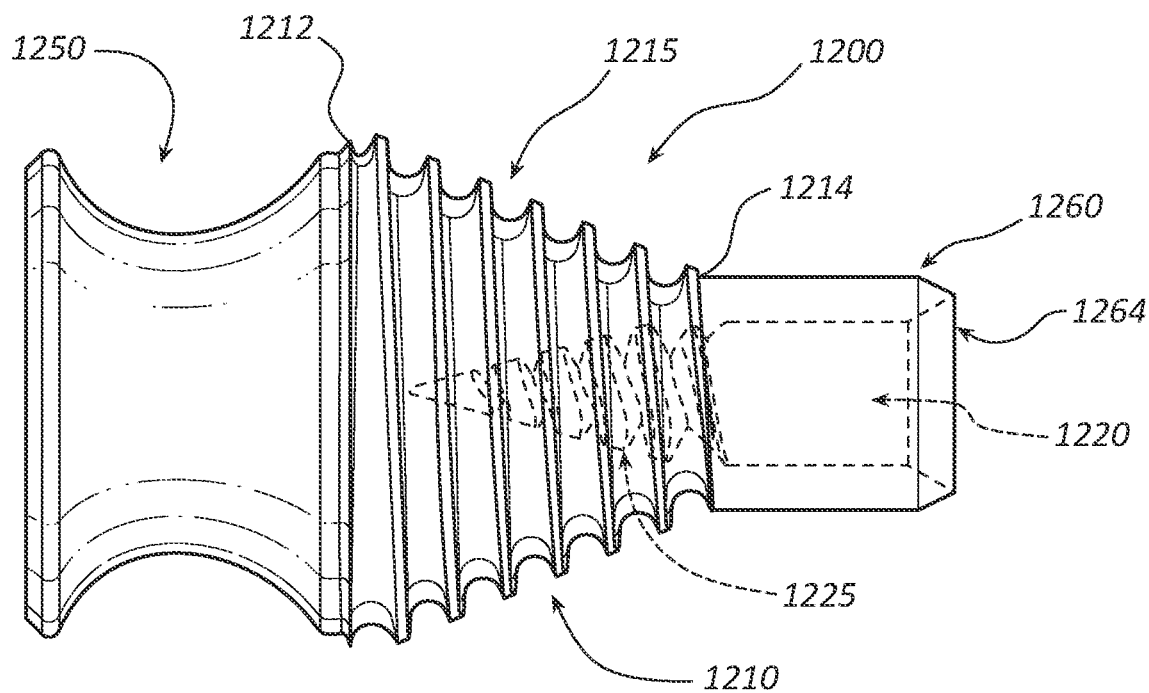
FIG. 12A is a perspective view of a vertebral bone anchor according to additional embodiments.
Figure 12B:
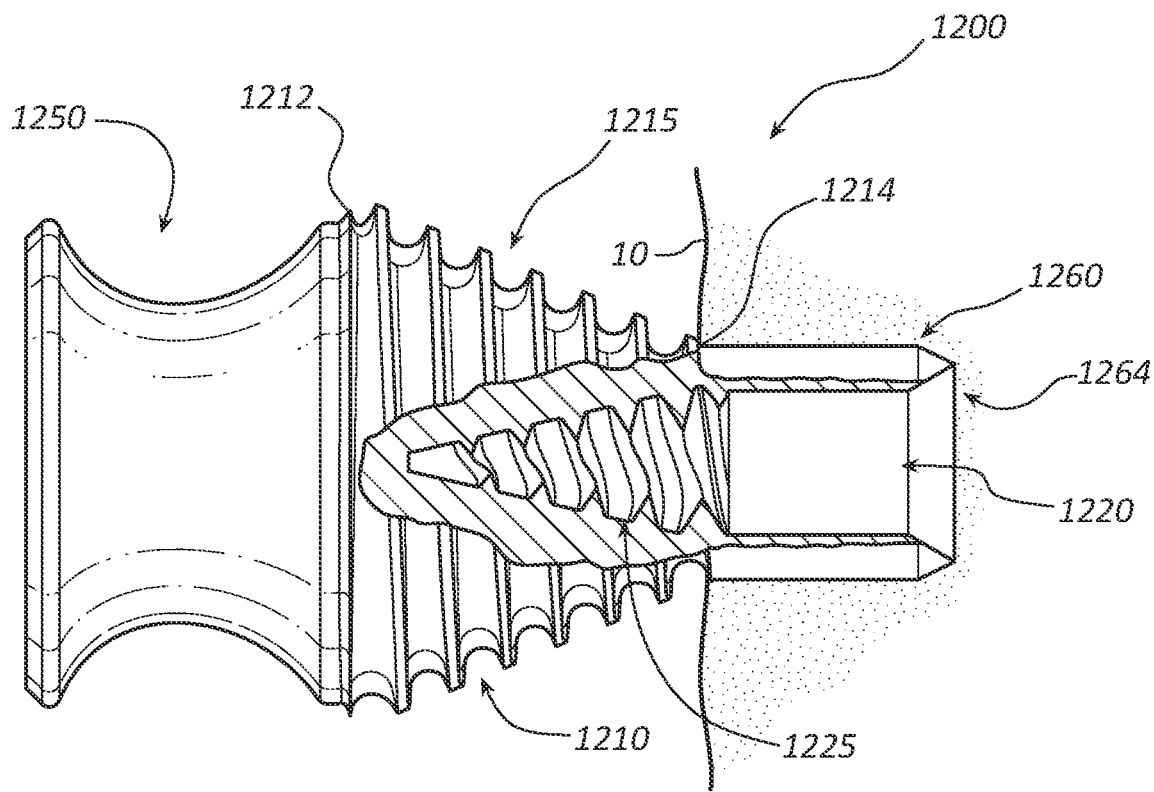
FIG. 12B is a perspective, partial cutaway view of the bone anchor of FIG. 12A being engaged with a vertebral body.

Another example of a bone anchor 1200 is shown in FIGS. 12A and 12B. Bone anchor 1200 is similar to the bone anchors depicted and discussed previously except for the presence of a non-tapering, cylindrical tip 1260. Tip 1260 extends from the distal end 1214 of a tapering portion 1210 (opposite proximal end 1212) and terminates at a preferably sharpened edge 1264 to facilitate penetration into a vertebral body 10 or other bone, as shown in FIG. 12B. In the depicted embodiment, tip 1260 lacks both internal and external threads. As such, bone anchor 1200 may be tamped into the bone before engaging any of the threads. However, in some embodiments, a portion of cylindrical tip 1260, such as preferably a proximal portion, may comprise internal and/or external threads.

It can also be seen that tip 1260 comprises an internal chamber 1220 that extends into the tapering portion. In addition, preferably, at least the proximal portion of chamber 1220 tapers or otherwise varies in size in a direction opposite to the taper of the exterior surface of bone anchor 1200. As previously described, this may allow for bone entering chamber 1220 to be compacted as the anchor 1200 is driven into the bone. In the depicted embodiment, chamber 1220 is cylindrical in shape, similar to the outer surface of tip 1260, along tip 1260 and the reverse tapering of chamber 1220 begins at, or at least substantially at, the distal end 1214 of the tapering section 1210. However, this need not be the case in all embodiments. Indeed, the reverse tapering or other decrease in size of the chamber 1220 from the distal to the proximal end may begin within the cylindrical/non-tapering tip 1260 or may begin proximally of the distal end 1214 of the tapering section.

Otherwise, bone anchor 1200 may be similar to the other anchors depicted in other drawings. For example, the tapering section 1210 may comprise an external thread form 1215 and at least a portion of the inner chamber 1220 may comprise an internal thread form 1225. In some embodiments, the external thread form 1215 may differ from the internal thread form 1225 in one or more ways so as to provide a differential in force between forces generated by the external thread form 1215 on bone adjacent thereto and forces generated by the inner thread form 1225 on bone adjacent thereto. For example, the inner and outer thread forms differ from one another in thread depth, thread direction, number of starts, angle, pitch diameter, major diameter, and/or minor diameter. The internal and/or external thread forms may also vary between their respective proximal and distal ends. In some such embodiments, the internal and/or external thread forms may vary in ways that are different from one another, such as varying along their respective lengths in opposite directions, for example.

Bone anchor 1200 may further comprise an engagement member 1250 for engaging ligaments or other engagement bands, as previously mentioned. One or more of the other features previously described, such as a central cannulation, a keyed feature to facilitate engagement with a driver or other suitable instrument for driving the anchor 1200 into a vertebral body 10 or other tissue, and/or one or more tunnels and/or openings that extend from the exterior surface of anchor 1200 to the inner chamber 1220 may also be provided if desired/useful.

As shown in FIG. 12B, once the non-tapering tip 1260 has been tamped or otherwise inserted into the vertebral body 10, external threads 1215 may be engaged and bone anchor 1200 may be advanced further into the vertebral body 10 by rotation of bone anchor 1200.

Figure 13A:
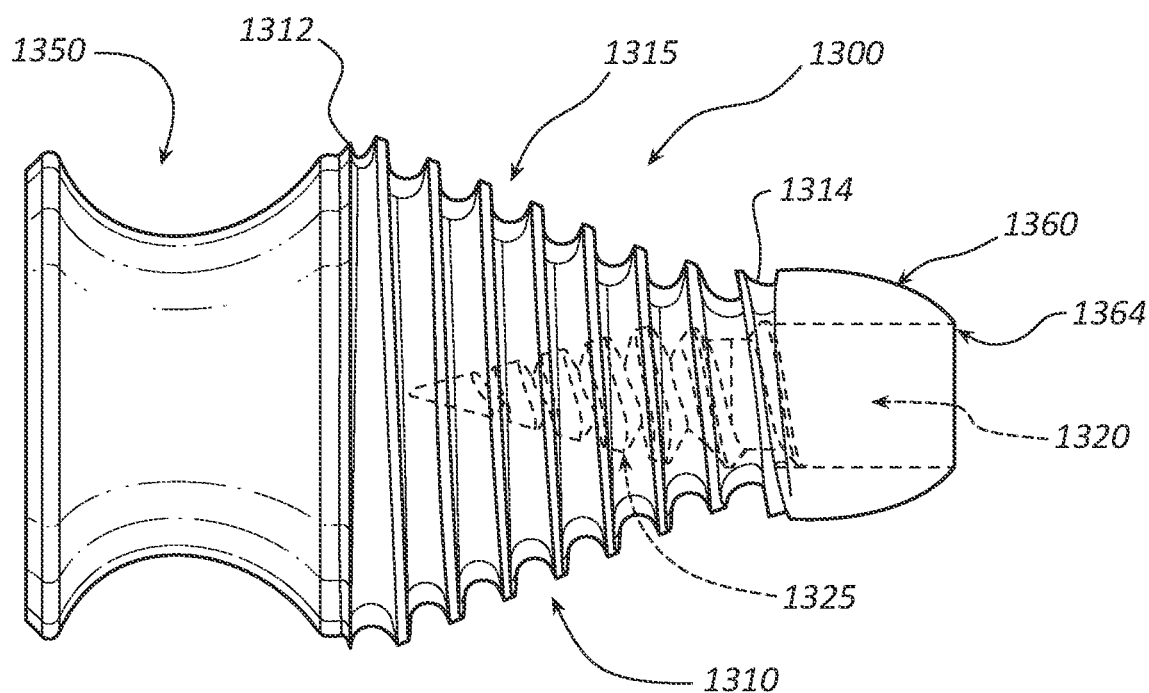
FIG. 13A is a perspective view of a vertebral bone anchor according to further embodiments.
Figure 13B:
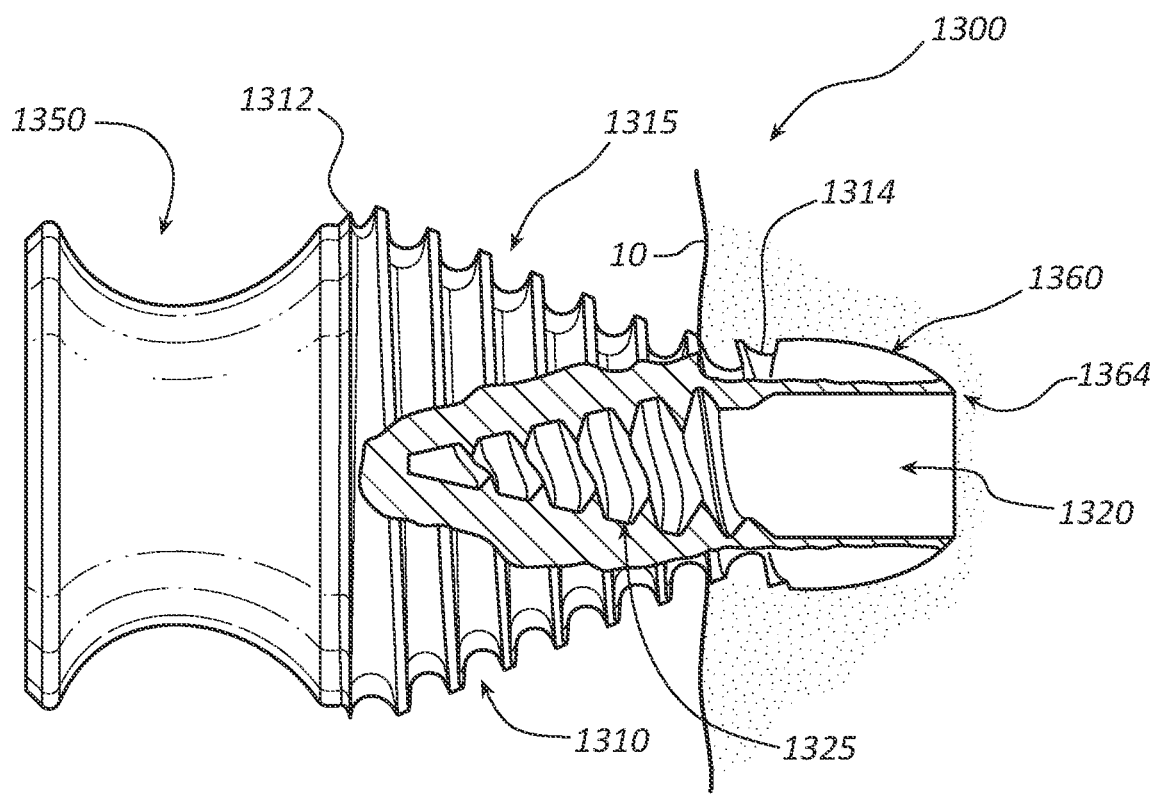
FIG. 13B is a perspective, partial cutaway view of the bone anchor of FIG. 13A being engaged with a vertebral body.

Still another example of a bone anchor 1300 is shown in FIGS. 13A and 13B. Bone anchor 1300 is similar to the bone anchors depicted and discussed previously except for the presence of a tip 1360 that is curved rather than cylindrical as with bone anchor 1200. Tip 1360 extends from the distal end 1314 of a tapering portion 1310 (opposite proximal end 1312) and terminates at a preferably sharpened edge 1364 to facilitate penetration into a vertebral body 10 or other bone, as shown in FIG. 13B. In the depicted embodiment, tip 1360 lacks both internal and external threads. As such, bone anchor 1300 may be tamped into the bone before engaging any of the threads. However, in some embodiments, a portion of cylindrical tip 1360, such as preferably a proximal portion, may comprise internal and/or external threads.

For example, as discussed below in connection with bone anchor 1400, it may be desired in alternative embodiments to begin external thread form 1315 along a proximal portion of tip 1360. As an even more specific example, it may be desired in some embodiments to form threads, which may extend into thread form 1315 continuously in some such embodiments, beginning at or at least substantially at a midpoint of tip 1360 and/or at or at least substantially at the apex of the curve of tip 1360 (the point of the curve furthest from the central axis of the bone anchor 1300).

Tip 1360 further comprises an internal chamber 1320 that extends into the tapering portion. In addition, preferably, at least the proximal portion of chamber 1320 tapers or otherwise varies in size in a direction opposite to the taper of the exterior surface of bone anchor 1300. As previously described, this may allow for bone entering chamber 1320 to be compacted as the anchor 1300 is driven into the bone. In the depicted embodiment, chamber 1320 is cylindrical in shape along tip 1360, similar to the outer surface of tip 1360, and the reverse tapering of chamber 1320 begins at, or at least substantially at, the distal end 1314 of the tapering section 1310. However, this need not be the case in all embodiments. Indeed, the reverse tapering or other decrease in size of the chamber 1320 from the distal to the proximal end may begin within the bowed tip 1360 or may begin proximally of the distal end 1314 of the tapering section. As another alternative, the reverse tapering or other beginning of a decrease in size of the chamber 1320 from distal to proximal may begin at the point at which the external threads begin, which may, as described above, coincide, or at least substantially coincide, with the apex of the curve and/or the midpoint of the tip 1360. In alternative embodiments, tip 1360 may taper to define a conical section rather than a bowed/curved section.

Otherwise, bone anchor 1300 may be similar to the other anchors depicted in other drawings. For example, the tapering section 1310 may comprise an external thread form 1315 and at least a portion of the inner chamber 1320 may comprise an internal thread form 1325. In some embodiments, the external thread form 1315 may differ from the internal thread form 1325 in one or more ways so as to provide a differential in force between forces generated by the external thread form 1315 on bone adjacent thereto and forces generated by the inner thread form 1325 on bone adjacent thereto in any of the ways previously described.

Bone anchor 1300 may further comprise an engagement member 1350 for engaging ligaments or other engagement bands, as previously mentioned. One or more of the other features previously described, such as a central cannulation, a keyed feature to facilitate engagement with a driver or other suitable instrument for driving the anchor 1300 into a vertebral body 10 or other tissue, and/or one or more tunnels and/or openings that extend from the exterior surface of anchor 1300 to the inner chamber 1320 may also be provided if desired/useful.

As shown in FIG. 13B, once the tip 1360 has been tamped or otherwise inserted into the vertebral body 10, external threads 1315 may be engaged and bone anchor 1300 may be advanced further into the vertebral body 10 by rotation of bone anchor 1300, as previously described.

Figure 14A:
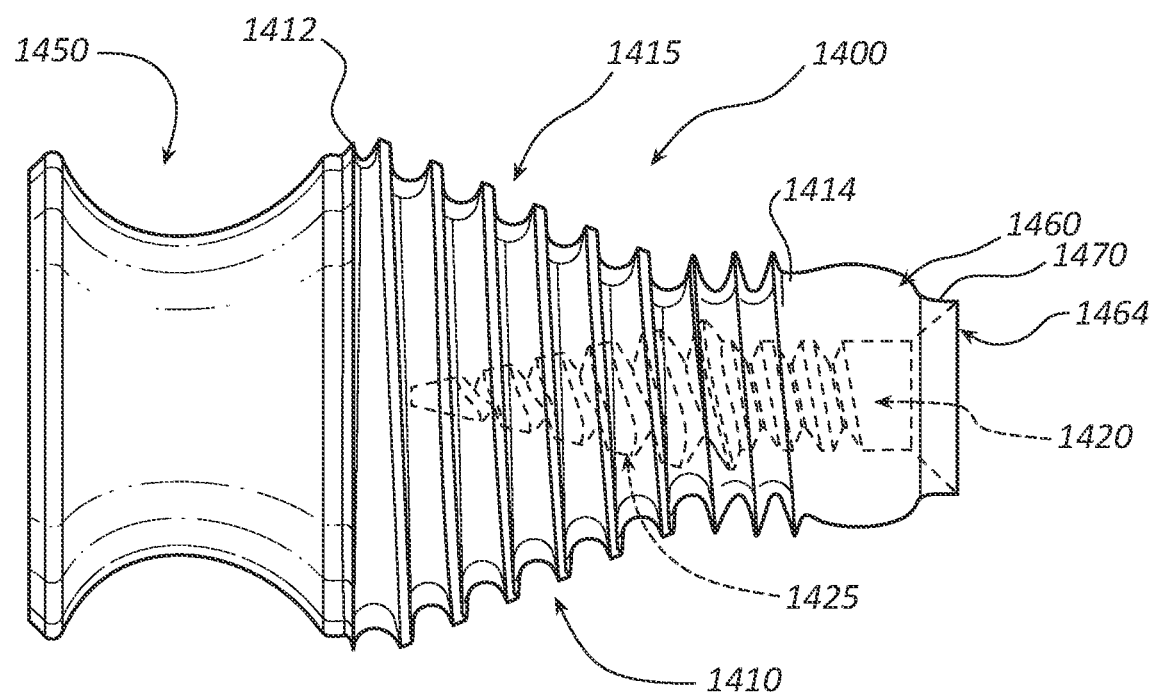
FIG. 14A is a perspective view of a vertebral bone anchor according to still other embodiments.
Figure 14B:
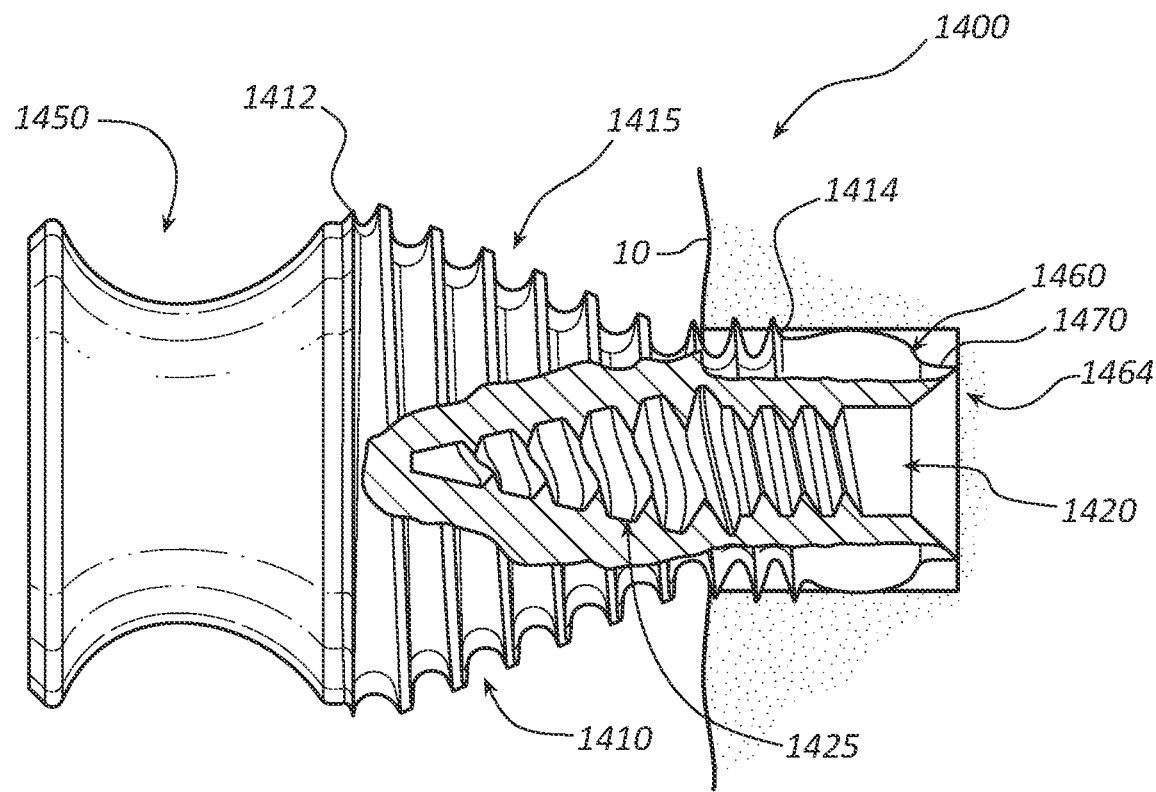
FIG. 14B is a perspective, partial cutaway view of the bone anchor of FIG. 14A being engaged with a vertebral body.
Figure 15A:
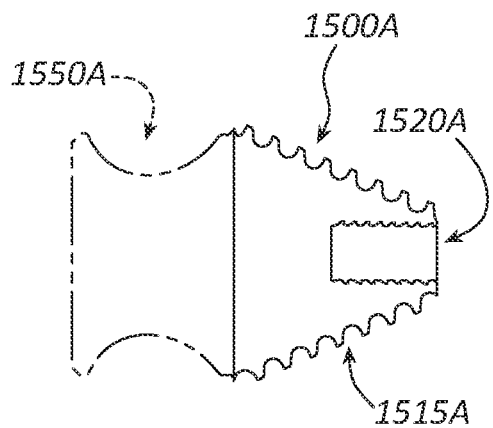
FIGS. 15A-15F are cross-sectional views of various bone anchors comprising distinct sizes, shapes, and/or types of inner chambers.
Figure 15D:
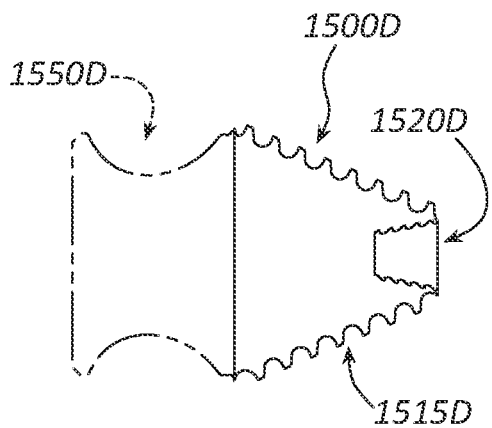
Figure 15B:
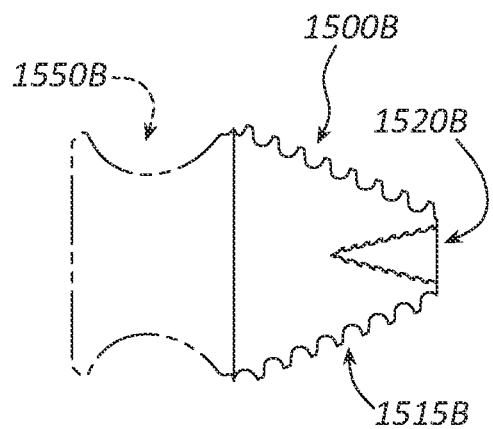
Figure 15E:
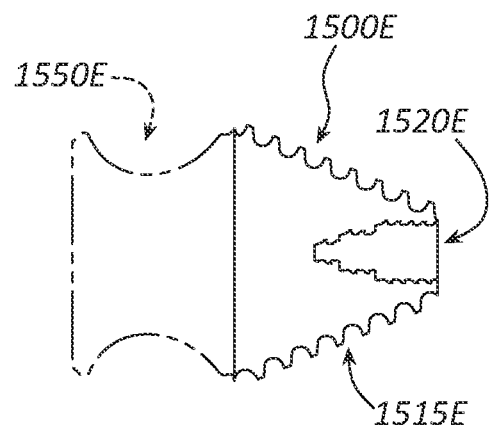
Figure 15C:
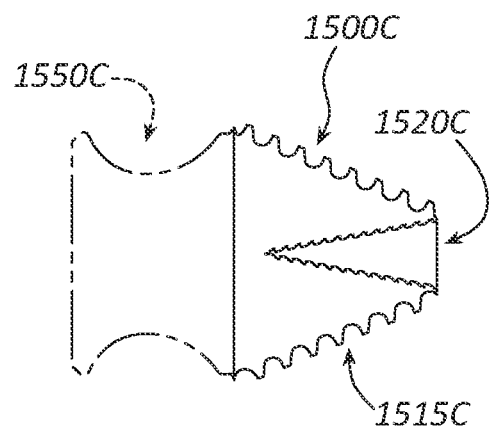
Figure 15F:
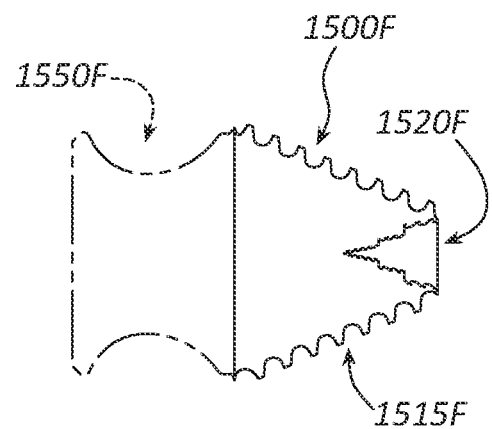

Another example of a bone anchor 1400 according to still other embodiments is shown in FIGS. 14A and 14B. Bone anchor 1400 is similar to the bone anchors depicted and discussed previously except for the configuration of the tip, which includes a distal end portion 1470 that is cylindrical and an adjacent curved/bowed portion 1460. Cylindrical tip 1470 may again comprise a sharp edge to facilitate penetration/tamping into a vertebral body or other bone. The adjacent bowed/curved portion 1460 may serve one or more useful functions such as providing inhibiting forces to slow down the tamping of bone anchor 1400 prior to engagement of threads, external and/or internal, with the adjacent bone. This may allow for creation of an initial circular channel with an expansion created by the bowed/curved portion 1460 (or similar cylindrical section) wide enough to allow the initial thread starting from external thread form 1415 to enter below the cortical wall and easily engage the cancellous bone underneath the cortical wall for simple initial screw purchase and advancement.

As mentioned above in connection with section 1360, section 1460 may, in alternative embodiments, comprise a tapering and/or conical section rather than a curved/bowed section, which may provide similar benefits by, for example, slowing the rate of tamping by providing an opposing force after tip 1470 has entered the bone.

Bowed/curved section 1460 extends from the distal end 1414 of tapering portion 1410 (opposite proximal end 1412). In the depicted embodiment, tip section 1460 comprises external threads that preferably begin at or near the apex of the curvature, as described above, and may extend cylindrically for a short distance, after which they may taper along the tapered section 1410 to form a part of external thread form 1415.

Tip 1460 further comprises an internal chamber 1420 that extends into the tapering portion. In addition, preferably, at least the proximal portion of chamber 1420 tapers or otherwise varies in size in a direction opposite to the taper of the exterior surface of bone anchor 1400. Again, this may allow for bone entering chamber 1420 to be compacted as the anchor 1400 is driven into the bone. In the depicted embodiment, chamber 1420 is cylindrical in shape along the tip portions and the reverse tapering of chamber 1420 begins at, or at least substantially at, the distal end 1414 of the tapering section 1410.

However, this need not be the case in all embodiments. Indeed, the reverse tapering or other decrease in size of the chamber 1420 from the distal to the proximal end may begin within the bowed portion 1460, within the cylindrical tip portion 1470, or may begin proximally of the distal end 1414 of the tapering section. As another alternative, the reverse tapering or other beginning of a decrease in size of the chamber 1420 from distal to proximal may begin at the point at which the external threads begin, which may, as described above, coincide, or at least substantially coincide, with the apex of the curve and/or the midpoint of the bowed portion 1460.

Internal threads may also be formed within chamber 1420. For example, in the depicted embodiment, the internal thread form 1425 begins at or near the beginning of the external thread form 1415. Of course, this need not be the case in all embodiments. Indeed, the internal thread form may begin proximally or distally of the external thread form in alternative embodiments.

In the depicted embodiment, the internal thread form 1425 comprises a non-tapering section that may overlap with the bowed section 1460. In some cases, the internal thread form 1425 may coincide identically or at least substantially identically with the bowed section 1460 and/or tip 1470. The internal thread form 1425 may then reverse taper along the tapering section of the inner chamber 1420.

In some embodiments, the external thread form 1415 may differ from the internal thread form 1425 in one or more ways so as to provide a differential in force between forces generated by the external thread form 1415 on bone adjacent thereto and forces generated by the inner thread form 1425 on bone adjacent thereto in one or more of the ways described elsewhere herein.

Bone anchor 1400 may further comprise an engagement member 1450 for engaging ligaments or other engagement bands, as previously mentioned. One or more of the other features previously described, such as a central cannulation, a keyed feature to facilitate engagement with a driver or other suitable instrument for driving the anchor 1400 into a vertebral body 10 or other tissue, and/or one or more tunnels and/or openings that extend from the exterior surface of anchor 1400 to the inner chamber 1420 may also be provided if desired/useful.

As shown in FIG. 14B, once the tip (made up of tip portions 1460 and 1470) has been tamped or otherwise inserted into the vertebral body 10, external threads 1415 may be engaged and bone anchor 1400 may be advanced further into the vertebral body 10 by rotation of bone anchor 1400, as previously described.

Additional bone anchors 1500A-1500F are depicted in FIGS. 15A-15F, respectively, each of which comprises a respective outer thread form 1515A-1515F, a respective engagement member 1550A-1550F having a seat for coupling with a tether, as described throughout this disclosure, along with distinct types of respective inner chambers 1520A-1520F.

More particularly, inner chamber 1520A comprises a non-tapering or cylindrical chamber, which is shown having bone engaging protrusions, such as inner threads, formed therein.

Inner chamber 1520B comprises a tapering or conical chamber that, as previously discussed, preferably tapers in a direction opposite that of the outer thread form 1515B such that the cross-sectional area of the chamber decreases in a distal to proximal direction. Inner chamber 1520B extends to about the midpoint of the anchor comprising outer thread form 1515B. Again, an inner thread form or other bone engaging protrusions may be formed within the inner chamber 1520B. However, it is contemplated that, in some embodiments, such bone engaging protrusions may be omitted if desired.

Inner chamber 1520C also comprises a tapering or conical chamber that tapers in a direction opposite that of outer thread form 1515C. However, unlike inner chamber 1520B, inner chamber 1520C extends along at least substantially the entire length of the portion of anchor 15000 having external threads 1515C for engagement with vertebral bone. Again, an inner thread form or other bone engaging protrusions may, but need not always be, formed within the inner chamber 1520C.

Inner chamber 1520D also comprises a tapering or conical chamber that tapers in a direction opposite that of outer thread form 1515D. However, unlike inner chambers 1520B and 1520D, the proximal end of inner chamber 1520D comprises a flattened surface rather than tapering to a pointed end. Again, an inner thread form or other bone engaging protrusions may, but need not always be, formed within the inner chamber 1520D.

Inner chamber 1520E of bone anchor 1500E comprises a chamber that, like the previously described tapering inner chambers, decreases in cross-sectional area from the distal to the proximal end of the chamber. However, unlike the chambers of bone anchors 1520A-1520D, inner chamber 1520E does so in a stepwise rather than a tapering manner. It is contemplated, however, that some embodiments may both taper and have one or more such steps if desired. Inner chamber 1520E comprises a flattened proximal end, similar to inner chamber 1520D. Again, an inner thread form or other bone engaging protrusions may, but need not always be, formed within the inner chamber 1520E.

Finally, inner chamber 1520F of bone anchor 1500F comprises both steps and tapering sections. In addition, the proximal end of inner chamber 1520F tapers to a pointed proximal end. However, it should be understood that the proximal end need not be pointed in other contemplated embodiments. Again, an inner thread form or other bone engaging protrusions may, but need not always be, formed within the inner chamber 1520F.

Figure 16:
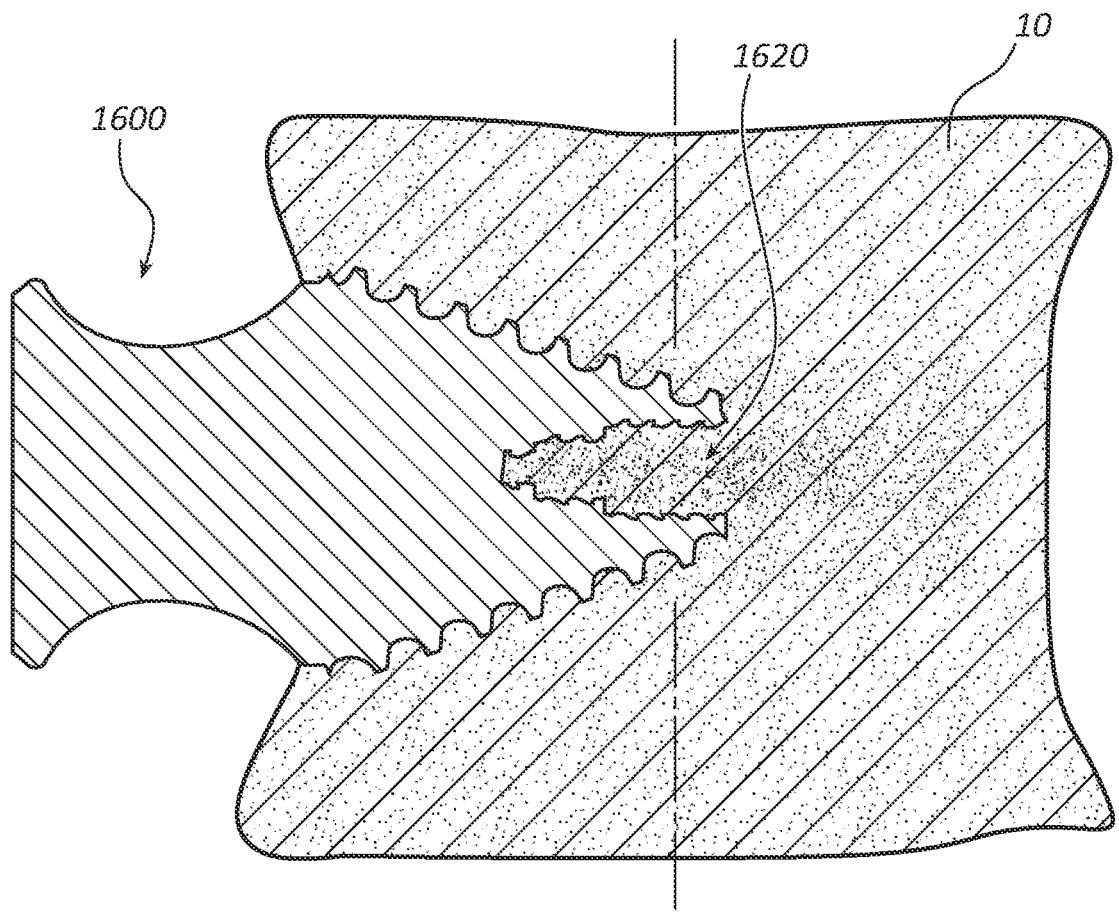
FIG. 16 is a cross-sectional view of another bone anchor within a vertebral body, the bone anchor having a stepped inner chamber with bone engaging features.

FIG. 16 illustrates a bone anchor 1600 inserted within a vertebral body 10. Bone anchor 1600 comprises an inner chamber 1620 that decreases in cross-sectional size/area from the distal to the proximal end of the chamber, as previously described. In addition, this figure illustrates how the inner chamber 1620 serves to engage and pack cancellous bone from the vertebral body 10 into the chamber 1620 as the bone anchor 1600 is advanced. This increases the density of the cancellous bone (possibly including some cortical bone from the initial penetration through the cortical wall of the implant) within the inner chamber 1620, which may provide a number of benefits, such as increased compression, increased surface area of bone contact, and increased healing and/or osseointegration of the implant.

As also shown in FIG. 16, some embodiments may also result in a gradient of increased bone density that may extend beyond the inner chamber 1620 of the implant 1600, which may effectively extend the length of fixation of the implant. Without being limited by theory, it is thought that the ability of the inner chamber to engage and pack bone within the implant, which may result from the aforementioned threads or other bone engaging members within the chamber and/or the narrowing of the chamber in a distal to proximal direction, may act as a plow or a prow of a ship to compress the region of the vertebral body in front of (distal of) the implant as it is advanced within the vertebral body. This may increase the strength of the coupling of the anchor with a vertebral body and may thereby increase the strength of the coupling between adjacent vertebrae and/or decrease the likelihood of the anchor becoming loosened and/or disengaged.

Figure 17:
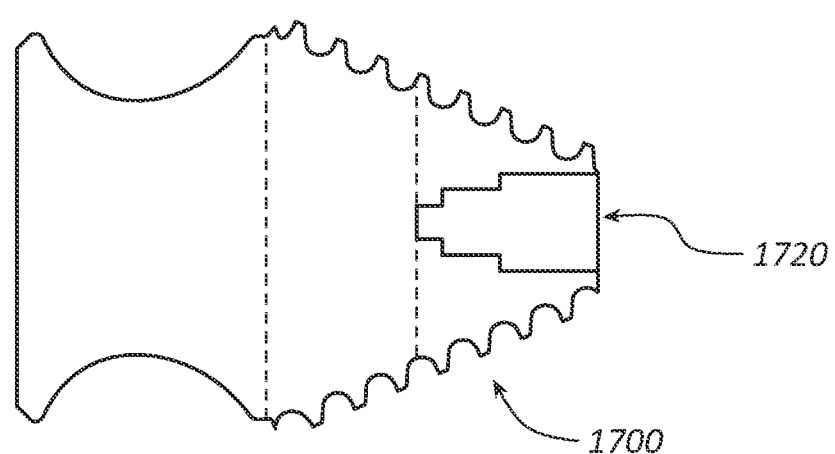
FIG. 17 is a cross-sectional view of another bone anchor having a stepped inner chamber.

FIG. 17 illustrates another embodiment of a bone anchor 1700 having an inner chamber 1720 that increases in cross-sectional area from the proximal to distal end in a stepwise fashion. Although no bone engaging members are depicted, it should be understood that any of the aforementioned threads or other bone engaging members may be present if desired. Inner chamber 1720 is shown extending to about the midpoint of the bone-engaging portion of the implant 1700. However, due one or more of the aforementioned advantageous features, such as providing bone engaging protrusions formed within the inner chamber and/or a profile that increases in cross-sectional area, at least in part, from a proximal end of the inner chamber to a distal end of the inner chamber, it is thought that some embodiments may be able to compress a very large portion of cancellous bone within inner chamber 1720.

For example, if the entire volume of the implant is considered to be "X", the volume of the inner chamber 1720 may be less than 0.5(X), or in some cases depending upon the size and shape of the inner chamber, even less than 0.25(X). However, due to the compacting of bone within the chamber, a relatively large portion of bone from the proximal portion of the vertebral body may be compacted as the anchor/implant 1700 is advanced such that, a volume of original, uncompacted bone much larger than the volume of chamber 1720 may, following full installation of chamber 1720, compacted therein. For example, in some embodiments and implementations, an uncompacted volume of (mostly cancellous) bone that is greater than about 0.75(X) may be compacted into a chamber having a size of less than 0.25(X). In some such embodiments and implementations, an uncompacted volume of (mostly cancellous) bone that is greater than about 0.90(X) may be compacted into a chamber having a size of less than 0.25(X).

Stated otherwise, using one or more of the inventive principles disclosed herein, a volume of uncompacted bone may be compacted into the inner chamber or chambers of the implant such that the compacted bone is at least twice as dense as the surrounding uncompacted bone. In some such embodiments and implementations, the volume of uncompacted bone may be compacted into the inner chamber or chambers of the implant such that the compacted bone is at least three times, or even four times, as dense as the surrounding uncompacted bone.

Figure 18A:
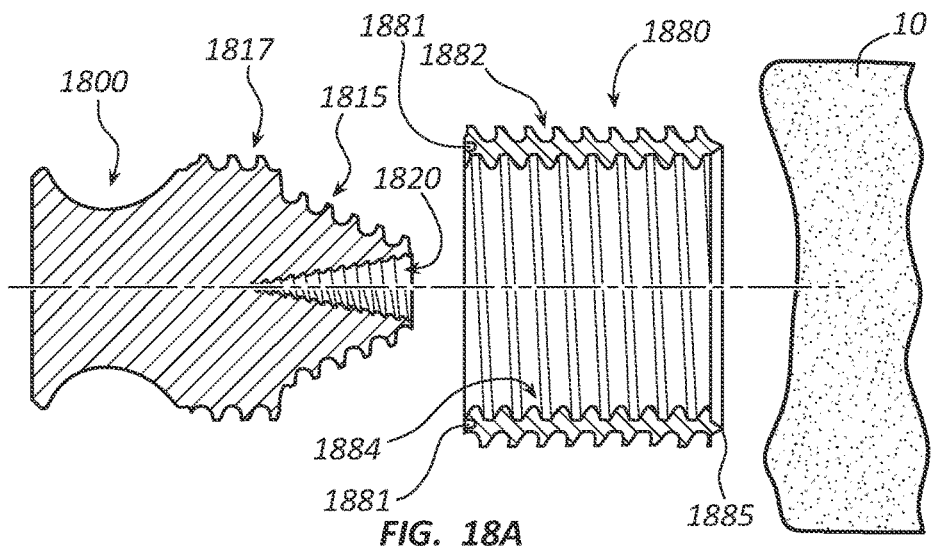
FIG. 18A depicts a two-piece bone anchor assembly according to some embodiments.
Figure 18B:
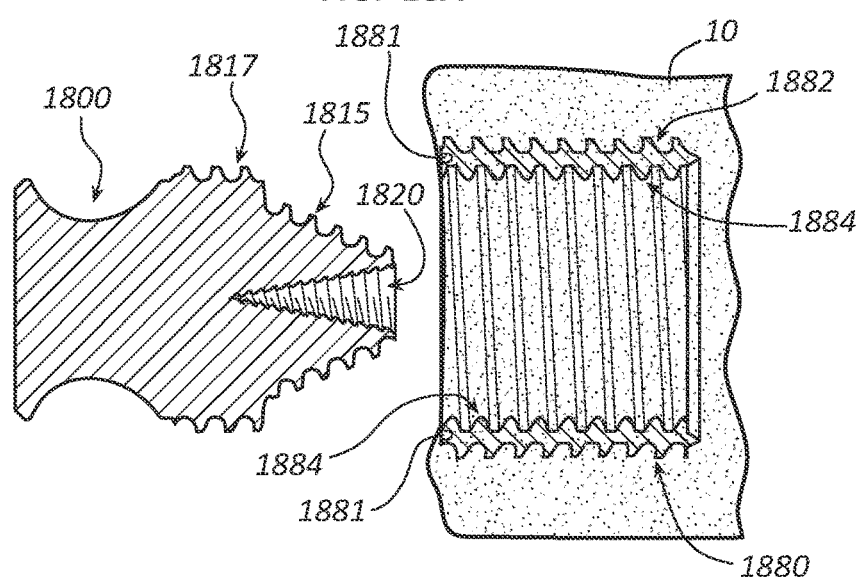
FIG. 18B depicts the two-piece bone anchor assembly of FIG. 18A after the first/outer piece of the assembly has been positioned within a vertebral body.
Figure 18C:
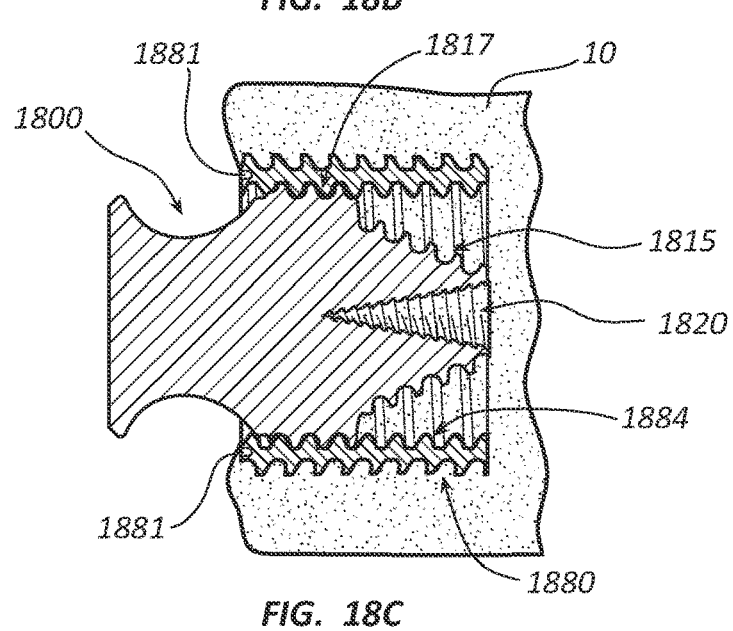
FIG. 18C depicts the two-piece bone anchor assembly of FIGS. 18A and 18B following coupling of the inner and outer pieces and fully extending the bone anchor assembly into the vertebral body.

FIGS. 18A-18C depict a bone anchor system comprising two interacting bone anchor elements, namely, a first, inner bone anchor 1800 and a second, outer bone anchor sleeve 1880. Bone anchor sleeve 1880 comprises a cylindrical shape having both inner and outer engagement features. More particularly, the outer surface of bone anchor sleeve 1880 comprises a first/outer thread form 1882 and the inner surface of bone anchor sleeve 1880 comprises a second/inner thread form 1884.

First thread form 1882 may be used to advance bone anchor sleeve 1880 into bone, such as vertebral body 10. A sharp leading edge 1885 may be provided to obtain initial purchase into the cortical wall of the vertebral body 10. Once this purchase has been obtained, sleeve 1880 may be threadably inserted into the vertebral body 10, as shown in FIG. 18B. One or more grooves 1881 or other instrument engaging features may be formed to facilitate use of a driver or other instrument in advancing the sleeve 1880.

After advancing, either fully or partially, the sleeve 1880 into the vertebral body 10, bone anchor 1800 may be advanced within the bone occupying the inner region of sleeve 1880. Initially, this advancement may be similar to that described previously in connection with one-piece bone anchor embodiments. However, eventually bone anchor 1800 will be physically coupled with sleeve 1880.

Indeed, as shown in each of FIGS. 18A-18C, bone anchor 1800 comprises two distinct outer threaded portions—a first threaded portion 1815 at the distal end and a second threaded portion 1817 adjacent and proximal to the first threaded portion 1815. First threaded portion 1815 is configured to threadably engage the bone, as previously mentioned. However, second threaded portion 1817 is configured to engage the inner thread form 1884 of sleeve 1880 after sufficient advancement of first threaded portion 1815 within vertebral body 10, as shown in FIG. 18C.

In the depicted embodiment, there is a ledge between thread form 1815 and thread form 1817. However, this need not be the case for all contemplated embodiments. Rather, in other embodiments there may be a smooth transition between these two thread forms. In addition, although thread form 1815 is shown with a taper similar to the tapering outer thread forms of previous embodiments and thread form 1817 is shown with a cylindrical or non-tapering structure, this may also vary in alternative embodiments. For example, in some embodiments, proximal thread form 1817 may taper. In some such embodiments, inner thread form 1884 of sleeve 1880 may have a similar taper, either alone or in conjunction with a corresponding taper to outer thread form 1882 or another series of bone engaging features.

As with previous embodiments, bone anchor 1800 may further comprise an inner chamber 1820, which may comprise any of the shapes, features, and/or elements previously mentioned. In the depicted embodiment, inner chamber 1820 comprises a taper opposite the taper of thread form 1815 and may also be threaded and/or have other protruding, bone engaging members. As previously mentioned, in some embodiments having an inner thread form, the inner thread form may be distinct from one or both of the outer thread forms, such as, for example, by differing in thread direction/handedness, number of starts, angle, pitch diameter, major diameter, and/or minor diameter.

In addition, unlike previous embodiments, the combined implant of bone anchor 1800 and sleeve 1880 is configured to compact bone in two distinct regions. More particularly, as with previous embodiments, bone may be compacted within chamber 1820. In addition, further bone compacting may take place within the region defined in between sleeve 1880 and thread form 1815, which may further contribute to the strength of the coupling with the vertebral body 10. Thus, although the depicted embodiment is shown with a single, continuous inner thread form 1884, it is contemplated that, in alternative embodiments, two thread forms or one thread form and an adjacent alternative bone engaging structure, such as a plurality of spikes or other protrusions, may be formed along the inner surface of sleeve 1880, with the proximal thread form being configured for engagement with bone anchor 1800 and the distal thread form or other bone engaging features being configured for engaging and/or drawing cancellous bone into the annular chamber formed between these two pieces of the assembly/system.

Bone anchor 1800 may otherwise be similar to and/or incorporate any of the features, elements, and/or structures previously presented in connection with any of the other embodiments disclosed herein. Thus, preferably an inner chamber 1820 is formed, which, as shown in FIGS. 18A-18C may, for example, comprise a reverse taper, either partial or full, and may comprise internal threads or other bone engaging features that are preferably configured to draw and compact bone into inner chamber 1820. In some embodiments, the profile of inner chamber 1820 may increase in cross-sectional area, at least in part, from a proximal end of the inner chamber 1820 to a distal end of the inner chamber 1820 without providing the taper shown in the figures, such as by providing steps, for example. In addition, as previously mentioned, some embodiments may be configured to provide a force differential between the internal and external threads or other bone engaging features.

Figure 19A:
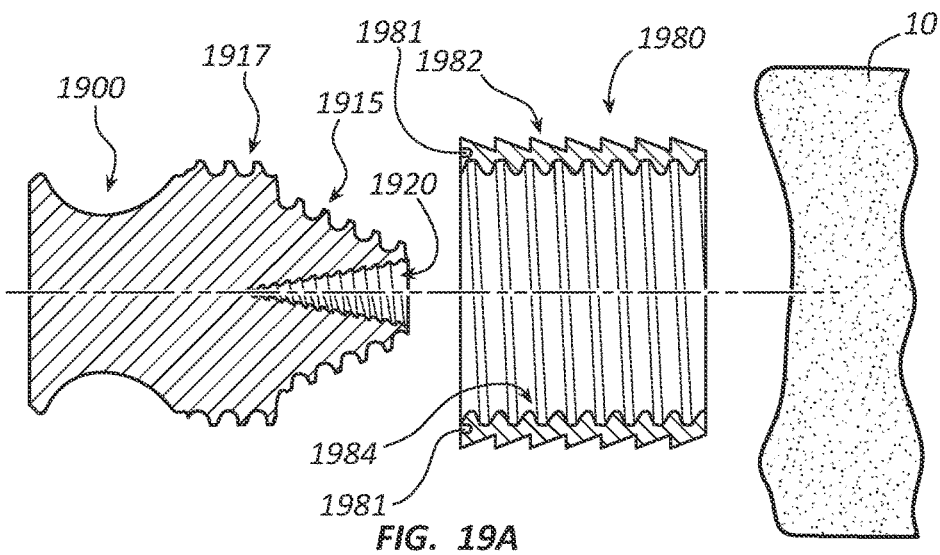
FIG. 19A depicts a two-piece bone anchor assembly according to other embodiments.
Figure 19B:
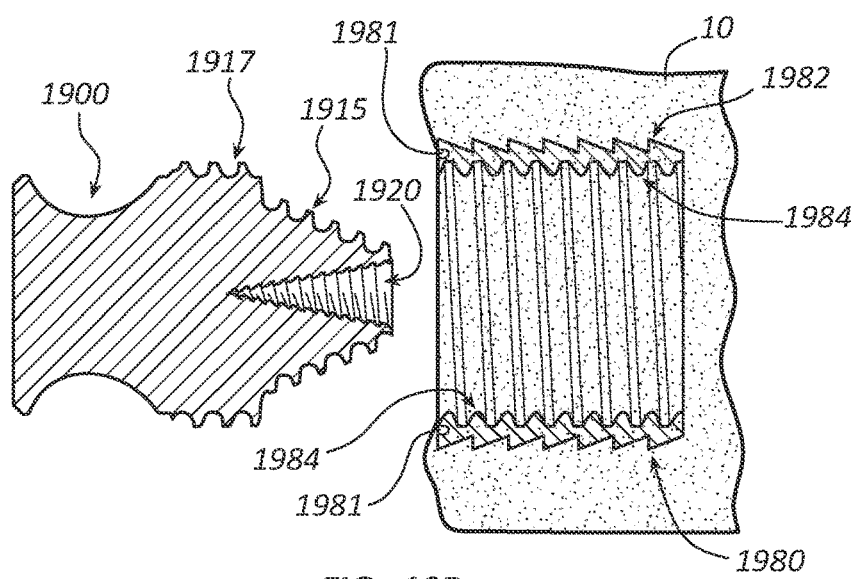
FIG. 19B depicts the two-piece bone anchor assembly of FIG. 19A after the first/outer piece of the assembly has been positioned within a vertebral body.
Figure 19C:
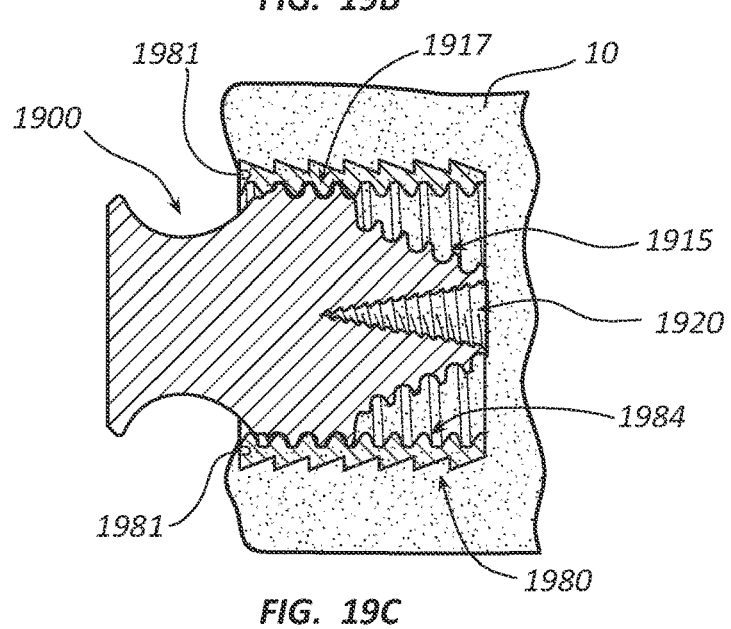
FIG. 19C depicts the two-piece bone anchor assembly of FIGS. 19A and 19B following coupling of the inner and outer pieces and fully extending the bone anchor assembly into the vertebral body.

FIGS. 19A-19C depict another bone anchor system comprising two interacting bone anchor elements, namely, a first, inner bone anchor 1900 and a second, outer bone anchor sleeve 1980. Bone anchor sleeve 1980 again comprises a cylindrical shape having both inner and outer engagement features. More particularly, the outer surface of bone anchor sleeve 1980 comprises outer bone engagement features in the form of a series of ratchet-like steps 1982 or the like and the inner surface of bone anchor sleeve 1980 comprises a thread form 1984.

Bone engaging features 1982 may be used to advance bone anchor sleeve 1980 into bone, such as vertebral body 10. A sharp leading edge (not shown) may be provided to obtain initial purchase into the cortical wall of the vertebral body 10 if desired. Once this purchase has been obtained, sleeve 1980 may be driven or otherwise advanced into the vertebral body 10, as shown in FIG. 19B. One or more grooves 1981 or other instrument engaging features may be formed to facilitate use of a driver or other instrument in advancing the sleeve 1980. Although not shown, a sharpened leading edge may be provided to facilitate the initial tamping of sleeve 1980 into the vertebral body 10 if desired.

After advancing, either fully or partially, the sleeve 1980 into the vertebral body 10, bone anchor 1900 may be advanced within the bone occupying the inner region of sleeve 1980, as discussed above in connection with bone anchor 1800.

As also discussed above in connection with bone anchor 1800, as shown in each of FIGS. 19A-19C, bone anchor 1900 comprises two distinct sets of engagement protrusions, both of which comprise threads in the depicted embodiment but need not in other contemplated embodiments. More particularly, a first threaded portion 1915 is formed at the distal end and a second threaded portion 1917 is formed adjacent and proximal to the first threaded portion 1915. First threaded portion 1915 is configured to threadably engage the bone, as previously mentioned, and second threaded portion 1917 is configured to engage the inner thread form 1984 of sleeve 1980 after sufficient advancement of first threaded portion 1915 within vertebral body 10, as shown in FIG. 19C.

Bone anchor 1900 may otherwise be similar to and/or incorporate any of the features, elements, and/or structures previously presented in connection with any of the other embodiments disclosed herein. Thus, again, preferably an inner chamber 1920 is formed, which may comprise a reverse taper, either partial or full, and/or internal threads or other bone engaging features that are preferably configured to draw and compact bone into inner chamber 1920. Rather than a strict taper, the profile of inner chamber 1920 may increase in cross-sectional area, at least in part, from a proximal end of the inner chamber 1920 to a distal end of the inner chamber 1920 in another manner, such as by a series of discrete steps or the like. In addition, as previously mentioned, some embodiments may be configured to provide a force differential between the internal and external threads or other bone engaging features.

Figure 20A:
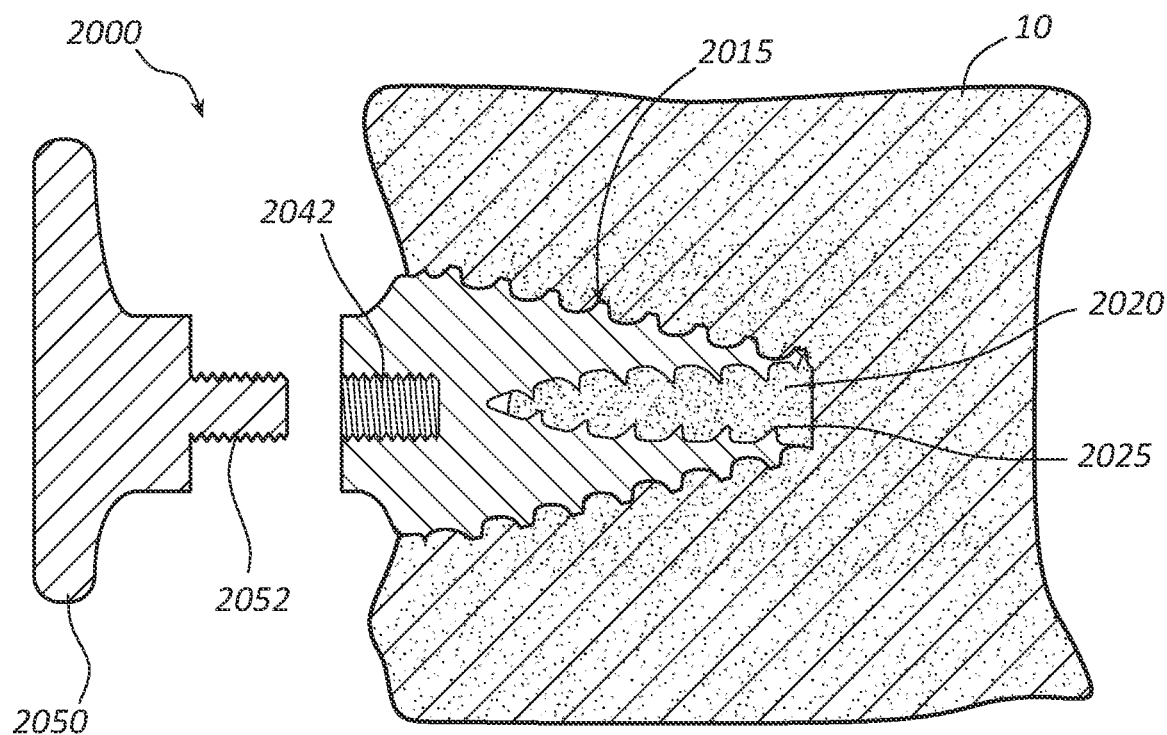
FIG. 20A is a cross-sectional view of a bone anchor having a removable cap/tether engagement member according to some embodiments shown with the cap removed.
Figure 20B:
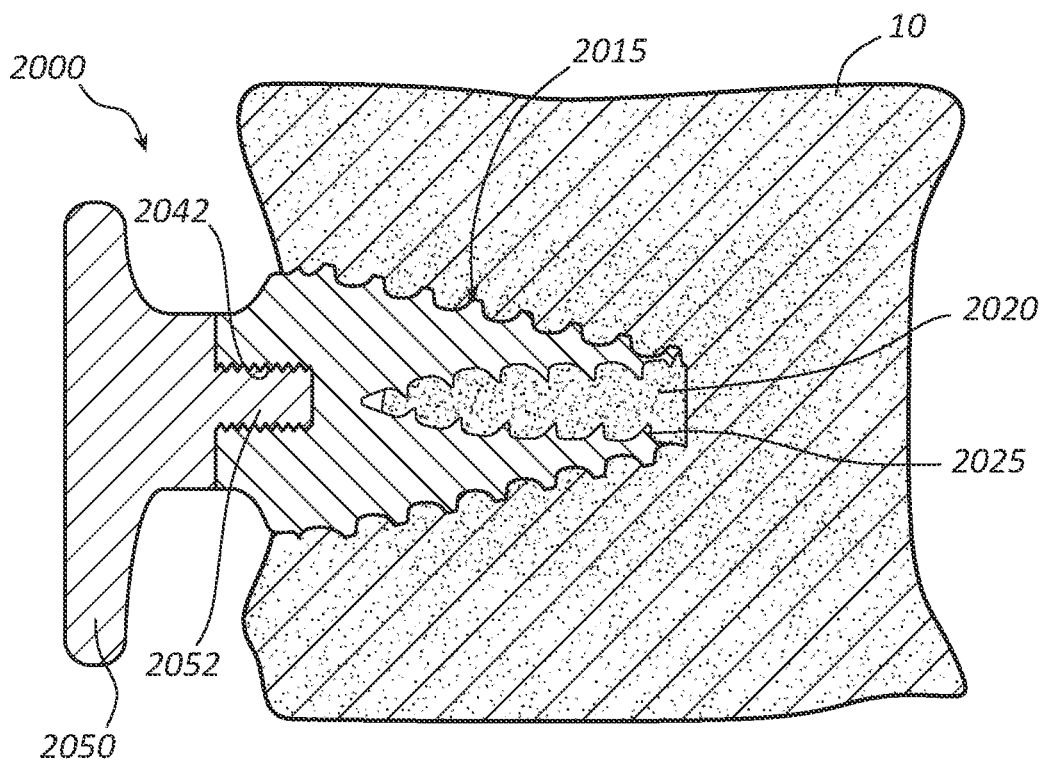
FIG. 20B depicts the bone anchor of FIG. 20A after the removable cap has been coupled with the bone-engaging portion of the anchor

A further embodiment of a bone anchor 2000 is depicted in FIGS. 20A and 20B. Bone anchor 2000 comprises a tether engagement member 2050, which in the depicted embodiment comprises a cap, that is removably coupleable with the body of the anchor 2000. In the depicted embodiment, tether engagement member 2050 further comprises a saddle having a threaded shaft 2052 configured to be threadably received within a threaded hole 2042 formed in a proximal portion of the bone engaging portion of anchor 2000 having external bone engaging threads 2015.

Tether engagement member/saddle 2050 may allow a surgeon/practitioner to, after advancing the bone engaging portion of anchor 2000 into a vertebral body 10, couple a loop tether around the portion of the anchor 2000 that protrudes from the vertebral body 10, as shown in FIG. 20A. After the tether (not shown) is wrapped around this portion of the anchor 2000, the tether engagement member/saddle 2050, which may be considered a "cap" of the assembly in this context, may be coupled to the bone engaging portion of the anchor 2000 in order to more permanently secure the tether to a pair of adjacent anchors and corresponding vertebral bodies. One perceived benefit with assemblies having removable saddle/caps is that anchors need not be over-loaded by requiring a surgeon/practitioner to stretch the tether around the proximal wall portion of the tether engagement member/saddle/cap 2050.

The remaining portions of bone anchor 2000 may be similar to any of those previously described. Thus, in the example of the depicted embodiment, an inner chamber 2020 may be provided, which may comprise a plurality of spikes (or, in other embodiments, threads or other bone engaging features) 2025 to facilitate packing cancellous bone into the chamber 2020.

Figure 21A:
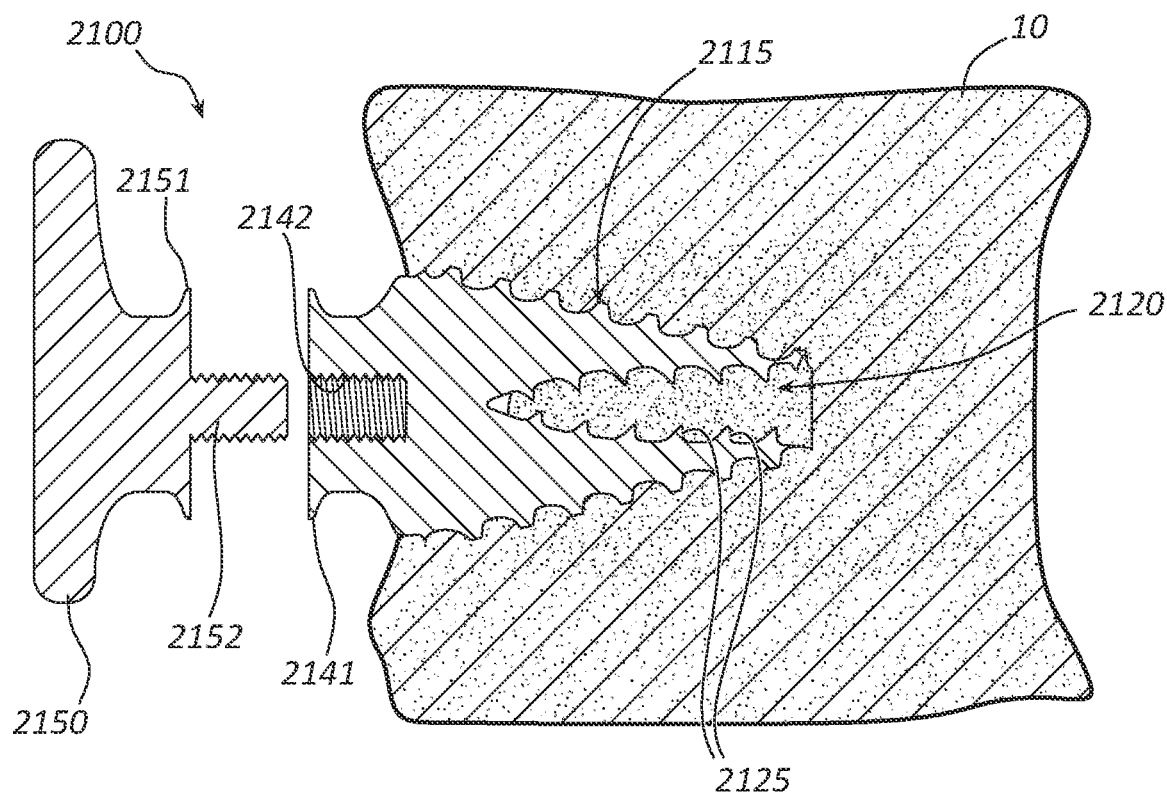
FIG. 21A is a cross-sectional view of a bone anchor having a removable cap/tether engagement member according to other embodiments shown with the cap removed.
Figure 21B:
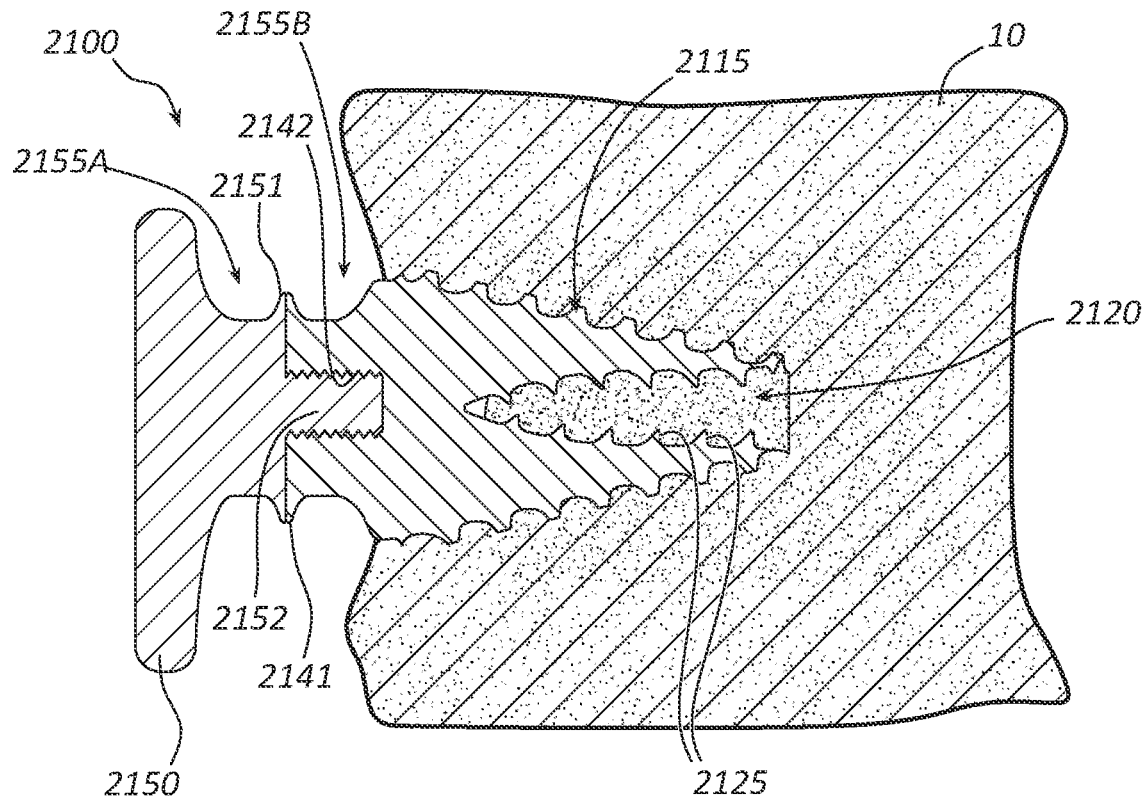
FIG. 21B depicts the bone anchor of FIG. 22A after the removable cap has been coupled with the bone-engaging portion of the anchor.

Another embodiment of a bone anchor 2100 is depicted in FIGS. 21A and 21B. Bone anchor 2100 is similar to bone anchor 2000 in that it comprises a tether engagement member 2150 or cap that is removably coupleable with the body of the anchor 2100. However, tether engagement member 2150 defines a portion of a W-shaped tether seating region having two seats 2155A and 2155B, as shown in FIG. 21B. These two seating regions are defined in part by respective circular protrusions 2141 and 2151 formed in the bone engaging and saddle/cap portions of the assembly, respectively.

Once the cap 2150 has been coupled with the bone engaging portion of the implant, which may take place by threadably engaging threaded shaft 2152 with threaded hole 2142, the two seating regions are formed, as shown in FIG. 21B. Seating region 2155B may be used as a temporary seat to allow a surgeon to extend a loop tether (not shown) about the saddle/seat region 2155B with cap 2150 removed, after which the tether may either be left in seating region 2155B or may be moved to seat 2155A to provide a more secure coupling to the remainder of the bone anchor 2100 and vertebral body 10. Because the center lip (defined by protrusions 2141 and 2151) is less pronounced than the proximal lip provided by the portion of the cap 2150 that is proximal of seating region 2155A, extending a loop tether about this center lip will require substantially less stretching/overloading of the loop tether during this temporary stage than would have been required to extend the loop tether about the proximal, larger lip defined by the proximal portion of cap 2150.

The remaining portions of bone anchor 2100 may be similar to any of those previously described. Thus, in the example of the depicted embodiment, an inner chamber 2120 similar to inner chamber 2020 may be provided, which may comprise a plurality of spikes (or, in other embodiments, threads or other bone engaging features) 2125 to facilitate packing cancellous bone into the chamber 2120.

Figure 22:
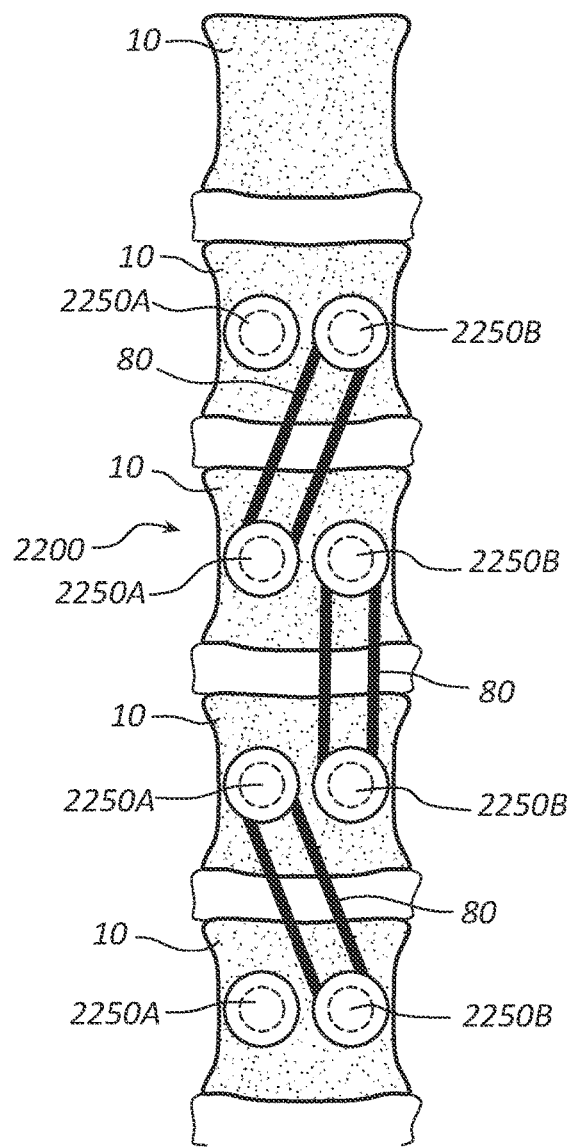
FIG. 22 depicts a system for spinal deformity correction according to some embodiments comprising multiple bone anchors per vertebral body and configured to allow for application of corrective forces in multiple directions simultaneously, such as derotational forces.

Another example of a system for spinal deformity correction 2200 is shown in FIG. 22. System 2200 comprises a plurality of bone anchors, each of which comprises a bone engaging portion (not visible in the figure) and a tether engaging portion 2250 coupled with the bone engaging portion. The bone engaging portion may, but need not, comprise any of the inner chambers, bone engaging features, thread forms or other elements disclosed herein. However, unlike any of the previous embodiments, system 2200 comprises two bone anchors and two corresponding tether engaging portions, such as saddles, for each vertebral body 10.

More specifically, each vertebral body 10 comprises a first bone anchor extending in a first column along a spinal column and a second bone anchor adjacent to the first bone anchor and extending in a second column adjacent to the first column along the spinal column. In FIG. 22, the portions of the first and second bone anchors that protrude from the vertebral bodies 10 are shown as tether engaging portions 2250A and 2250B, respectively.

Because of the presence of two anchors within each vertebral body 10 (or, in alternative embodiments and implementations, at least a subset of the vertebral bodies 10), a surgeon/practitioner may be able to apply lateral forces, such as derotational forces, if desired, to one or more portions of the spine, along with the forces directed along the axis of the spine. Thus, as shown in FIG. 22, a first tether 80 extends between the right anchor 2250B at the superior end of the system along the spine to the left anchor 2250A coupled with the adjacent vertebral body 10 below. The adjacent anchor 2250B in the same vertebral body 10 as the left anchor 2250A is then coupled with the right anchor 2250B in the adjacent vertebral body 10 below. The adjacent anchor 2250A to the left, however, is then coupled with the right anchor 2250B of the vertebral body 10 below. Thus, both axial forces, which are typical of the previous embodiments, and non-axial forces, may be provided using the same assembly/system.

Of course, this is just an example. As those of ordinary skill in the art will appreciate, by providing two (or more) adjacent anchors within one or more vertebral bodies 10, more precise and diverse forces may be applied to the spine to achieve other spinal deformity corrections, such as reversing torsional asymmetry induced by scoliosis, coronal correction, restoration of thoracic kyphosis, and/or realignment of thoracic torsion. Thus, it should be understood that tethers/ligaments 80 may be applied to the various anchors in a system comprising a plurality of anchors per vertebral body, such as system 2200, in any number of ways, which may include use of multiple tethers 80 coupled with a single anchor in some cases. For example, it may be desirable to couple a single anchor with both an anchor directly above/below and an anchor adjacent to the anchor directly above/below to apply both axial and derotational or other non-axial/lateral forces to the same anchor.

Figure 23:
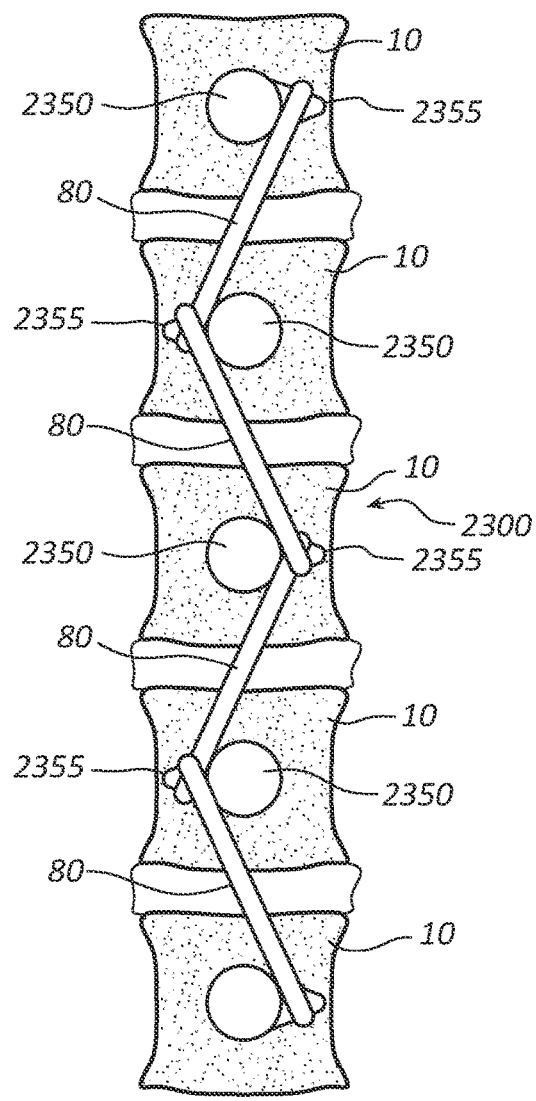
FIG. 23 depicts another example of a system for spinal deformity correction according to other embodiments comprising configured to allow for application of corrective forces to a spine in multiple directions simultaneously, such as derotational forces.

Another example of a derotational system 2300 is shown in FIG. 23. Unlike system 2200, however, system 2300 comprises a single anchor 2350 per vertebral body 10. To provide for the derotational function, or the ability to otherwise generate correctional forces that are not aligned with the vertical axis shown in FIG. 23, system 2300 therefore comprises bone anchors having protrusions 2355 that extend laterally relative to the axis of the corresponding anchors 2350 in opposing directions.

Thus, as shown in FIG. 23, some protrusions 2355 may extend laterally of their respective anchors towards one side of the spine and others may extend laterally their respective anchors towards the opposite side, which may allow for generation of derotational forces as needed/desired. This may be accomplished, for example, by coupling a tether/ligament 80—which may comprise a loop tether/ligament or another type of tether/ligament, such as a fixed length tether/ligament—with a protrusion 2355 extending to one side of the spinal column at one level and with a protrusion 2355 extending to the opposite side of the spinal column at an adjacent level.

In some embodiments, protrusions 2355 may be fixed with respect to their corresponding bone anchor 2350. In other words, the protrusions 2355 may be configured to fixedly extend in a given direction from a given bone anchor 2350, which may be accomplished, for example, by forming a hole through any of the saddles previously mentioned from which the protrusion 2355 may fixedly extend. In some such embodiments, the saddle may be rotationally decoupled from the bone engaging portion of the anchor such that the bone engaging portion may be rotatably and/or threadably inserted into the vertebral body 10 without rotating the position of the protrusion 2355.

Alternatively, the protrusions 2355 may be repositionable with respect to a given bone anchor 2350. For example, the protrusion 2355 may be rotatable with the bone anchor 2350 and therefore may be adjusted by rotation of the anchor 2350, or by rotation of just a portion of the anchor, such as a saddle, that protrudes from the vertebral body. In some such embodiments, a plurality of openings may be formed within the saddle/tether engaging portion of the bone anchor 2350 such that the position of the protrusion 2355 may be adjusted by placing it in a desired hole or other opening and then locking it in place. Alternatively, the protrusion 2355 may be fixedly coupled with the protruding/tether engaging portion of the anchor 2350, which itself may be rotatably coupled with the bone engaging portion, which may allow the protrusion 2355 to be rotated about the anchor and locked into place at a desired location.

FIGS. 24A-24C depict various bone anchors having different sized inner chambers that may be configured for use in connection with different types of bone and/or patients. For example, bone anchor 2400A comprises an inner chamber 2420A that extends only along about ⅓ of the distal end of the bone engaging portion of the implant 2400A. It is expected that this implant, or other similar implants in which the inner chamber extends along between about ¼ and about ½ of the distal end of the implant, may be particularly useful for patients having osteoporosis or otherwise having weakened bone. It is also thought that, for particularly sever osteoporotic patients and the like, a two-piece implant, such as the implant shown in FIGS. 18 and 19, may be useful. It should be understood that, although not shown in FIGS. 24A-24C, the inner chambers may comprise internal threads or other bone engaging features, as mentioned throughout this disclosure. In addition, it should be understood that these views are cross-sectional and that, typically, the inner chambers would be conical (if configured as shown in the figures) or otherwise decrease in cross-sectional area from the distal to the proximal end of the chamber, at least in part.

FIG. 24B depicts another bone anchor 2400B comprising an inner chamber 2420B that extends only along about ⅔ of the distal end of the bone engaging portion of the implant 2400B. It is expected that this implant, or other similar implants in which the inner chamber extends along between about ½ and about ¾ of the distal end of the implant, may be useful for most typical patients and bone types.

FIG. 24C depicts a bone anchor 24000 comprising an inner chamber 2420C that extends all of the way, or at least substantially all of the way, from the distal end of the bone engaging portion of the implant 24000 to the proximal end that may be coincident with the proximal cortical wall. It is expected that this implant, or other similar implants in which the inner chamber extends along between about ¾ and the full length of the implant, may be useful for stronger bone types.

FIG. 25 depicts another bone anchor/implant 2500 having an inner chamber 2520 and a removable cap 2550. Tether/ligament 80 may be coupled with a portion of the implant that protrudes from the bone engaging piece, after which the cap 2550 may be coupled to secure the tether/ligament 80. In some embodiments, the cap 2550 may be coupled by way of adhesives, snap-fit, fasteners, or the like. A gap 2552 between the cap 2550 and the adjacent portion of the anchor may, in some cases, be used to provide a smaller, more secure seat for the tether/ligament 80. Alternatively, this gap 2552 may be fully closed upon completion of coupling of cap 2550 to the anchor.

FIGS. 26A-26E depict various alternative structures for inner chambers (shown in cross-section) that may be useful to draw in and/or compact bone therein, as previously discussed throughout this disclosure. Inner chamber 2620A of bone anchor 2600A comprises a series of steps that result in the cross-sectional area of the chamber 2620A decreasing from the distal end of the anchor 2620A to its proximal end. A flattened proximal end of chamber 2620A, which may comprise, for example, a circular shape (or, alternatively, a rectangular or other desired shape) when viewed along a cross-section taken perpendicular to the primary axis of the anchor 2620A, is provided at the proximal-most region of the inner chamber 2620A. The steps and flattened proximal region may be used to compact bone in a series of distinct regions during use. Although not shown, any of the threads, spikes, or other desired bone engaging features/members may be positioned within chamber 2620A, if desired.

Another example of an inner chamber 2620B of a bone anchor 2600B is shown in FIG. 26B. Inner chamber 2620B is similar to inner chamber 2620A in that it comprises a plurality of discrete steps at which the cross-sectional area decreases from the distal to the proximal end (or increases in the opposite direction). However, unlike chamber 2620A, chamber 2620B comprises a tapering region terminating in a pointed base at the proximal end of the chamber 2620B. Thus, chamber 2620B comprises a cross-sectional area that decreases from the distal to the proximal end by way of both discrete steps and tapers, which may be positioned as desired throughout the chamber 2620B. This may allow for establishing both bone density gradients and discrete regions of bone density variations in within the vertebral body in which the anchor 2600B is positioned. Again, any of the threads, spikes, or other desired bone engaging features/members may be positioned within chamber 2620B, if desired.

FIGS. 26C-26E depict other examples of bone anchors 2600C-2600E having inner chambers 2620C-2620E, respectively. Each of these inner chambers 2620C-2620E is shown having a simple tapered shape for simplicity and ease of illustration. However, it should be understood that any of these chambers may comprise any combination of steps, tapers, or any of the other features or elements discussed herein or otherwise available to those of ordinary skill in the art. The purpose of these figures, however, is to show how the bone engaging elements may comprise spikes that protrude in a variety of directions. Thus, the spikes of chamber 2620C protrude distally, the spikes of chamber 2620D protrude proximally, and the spikes of chamber 2620E extend perpendicular, or at least substantially perpendicular, to the axis of its respective bone anchor 2600C/2600D/2600E.

FIGS. 27A and 27B depict two configurations of a loop ligament/tether that is configured to shrink in size between an initial configuration 80A shown in FIG. 27A to a subsequent configuration 80B in which the ligament/tether is shorter in length, which may allow for increasing the tension on an associated pair of bone anchors to apply a corrective force to a portion of a patient's spine. In some embodiments, this feature may be accomplished by using heat-shrink tubing or other heat-shrinking materials, which may include thermoplastic materials such as polyolefins, polyesters (such as polyethylene terephthalate), fluoropolymers (such as FEP, PTFE or Kynar), PVC, neoprene, and/or silicone elastomers, for example. In preferred embodiments, one or more heat-shrinkable materials may be incorporated into the ligament/tether, which may be a loop ligament/tether, as shown in FIGS. 27A and 27B, or may be a straight tether/ligament in other embodiments, which preferably shrink to a desired size by use of a patient's body temperature alone.

In this manner, the tether/ligament may be coupled with a pair of adjacent bone anchors in a first, un-shrunk configuration at a first temperature, which may be room temperature or, alternatively, may be a lower temperature, such as a temperature typically requiring refrigeration, and then may be configured to automatically shrink to a desired second, shrunk configuration using only the patient's internal body temperature. Thus, the tether may be configured to shrink to its final size at a temperature of between about 95 and about 100 degrees in some embodiments.

In some embodiments and implementations, a surgeon may select from a variety of different tethers, each of which may be configured to change sizes by a different amount that is predetermined. In this manner, a surgeon may be able to apply different forces simply by selecting between a plurality of tethers/ligaments each having a distinct, predetermined amount of resizing, which may depend upon the materials and configuration of the tether.

FIGS. 28A-28D are simple diagrams of various bone anchors 2800A-2800D illustrating possible configurations of the external surfaces and corresponding thread forms 2815A-2815D of the implants. Each of the inner chambers 2820A-2820D is shown with a simple tapering configuration, again for simplicity's sake, but may vary as desired using one or more of the features/principles disclosed herein.

Figure 28A:
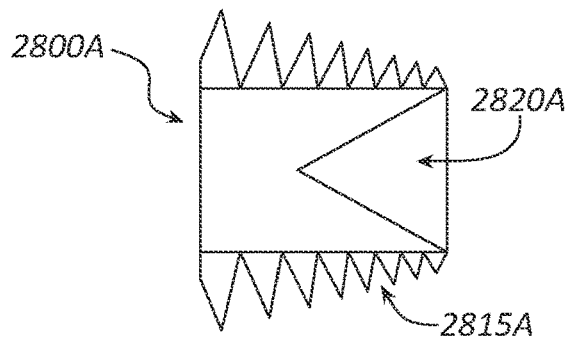
FIGS. 28A-28D depict various alternative configurations for an outer thread form for bone anchors.
Figure 28B:
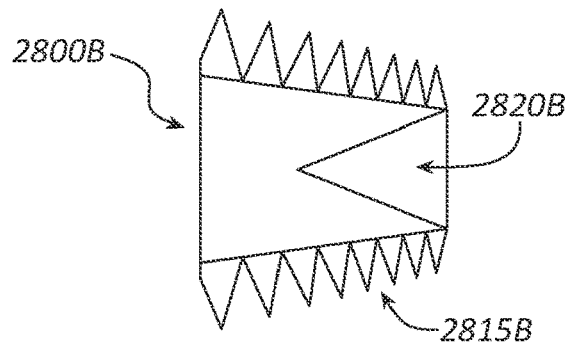
Figure 28C:
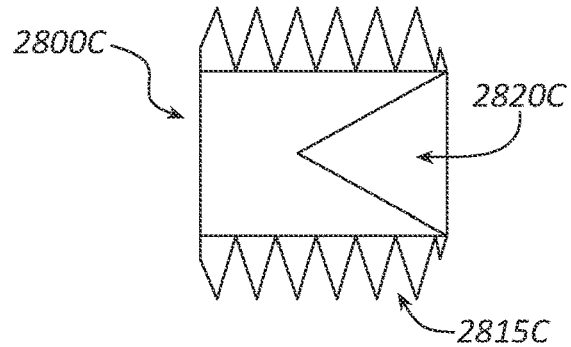
Figure 28D:
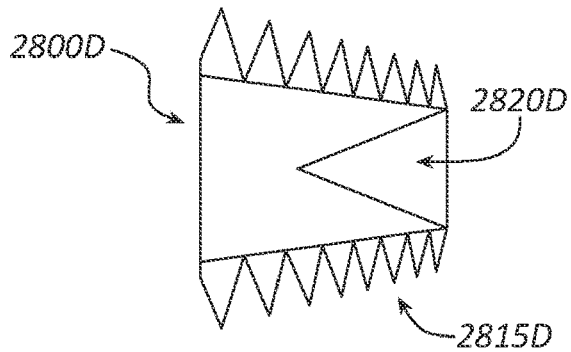

As shown in FIG. 28A, bone anchor 2800A comprises an external thread form 2815A that has a tapering major/outer diameter and a non-tapering minor/inner diameter. Bone anchor 2800B comprises an external thread form 2815B that has a tapering major/outer diameter and a tapering minor/inner diameter. Bone anchor 28000 comprises an external thread form 2815C that has a non-tapering major/outer diameter and a non-tapering minor/inner diameter. And finally, bone anchor 2800D comprises an external thread form 2815D that has a tapering major/outer diameter and a tapering minor/inner diameter.

Figure 29A:
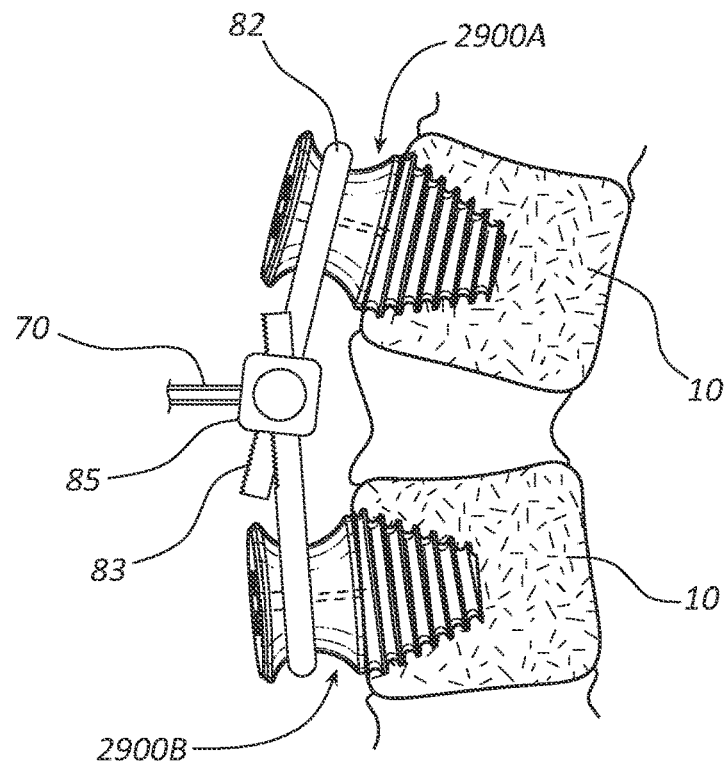
FIGS. 29A and 29B are perspective views of a system for spinal deformity correction comprising a selectively tensionable ligament according to some embodiments during a method for spinal correction using the system.
Figure 29B:
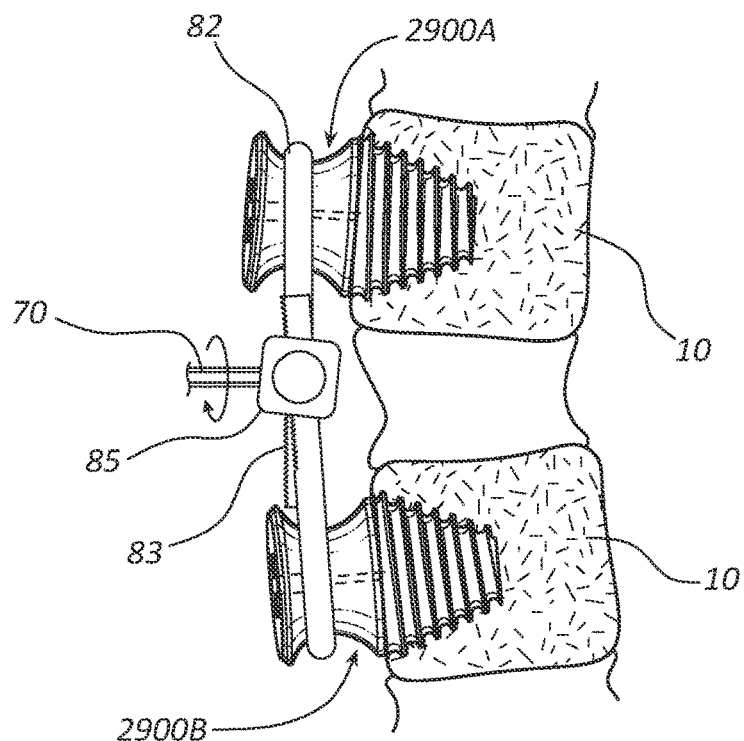

FIGS. 29A and 29B depict yet another example of a system for spinal deformity correction. This system is shown with two adjacent bone anchors, namely, bone anchor 2900A and bone anchor 2900B, positioned in two adjacent vertebral bodies 10. This system also comprises a straight ligament 82 that is configured to be formed into a loop and shortened manually between the first configuration shown in FIG. 29A and the second configuration shown in FIG. 29B. More particularly, a means for selectively shortening tether/ligament 82, such as ratchet mechanism 85, may be used, along with a suitable instrument 70, to shorten the length of tether 82 and thereby increase the force between the adjacent anchors 2900A and 2900B, as illustrated in FIG. 29B.

A series of teeth 83 may be formed along one or both ends of tether 82, which teeth 83 may cooperate with a corresponding set of ratcheting teeth within mechanism 85. Alternatively, teeth or other engaging features may only be present within mechanism 85. As another possible alternative embodiment, instrument 70 may be configured to simply decrease the size of an opening through which one or both ends of tether 82 extend, in which case a user may, for example, pull one end of tether 82 through mechanism 85 and then tighten/decrease the size of the aforementioned opening.

Figure 30A:
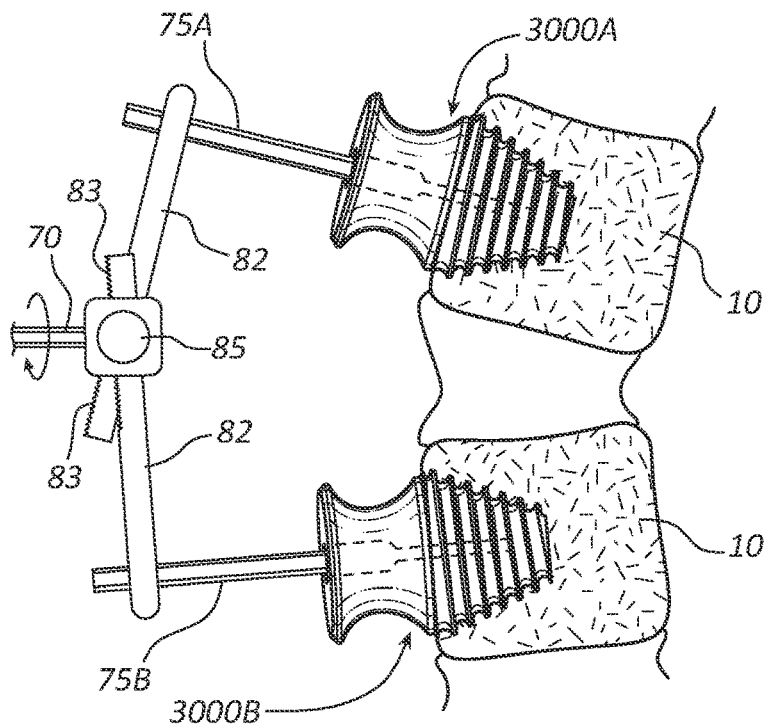
FIGS. 30A-30C are perspective views of a system for spinal deformity correction comprising a tensioning assembly according to some embodiments during a method for spinal correction using the system.
Figure 30C:
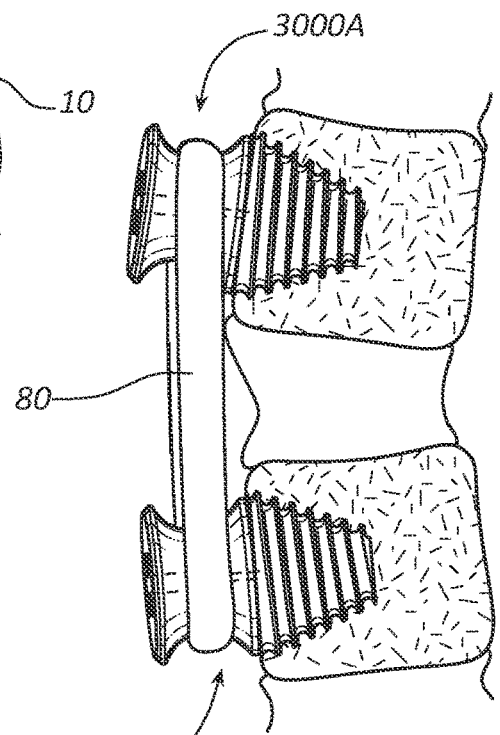
Figure 30B:
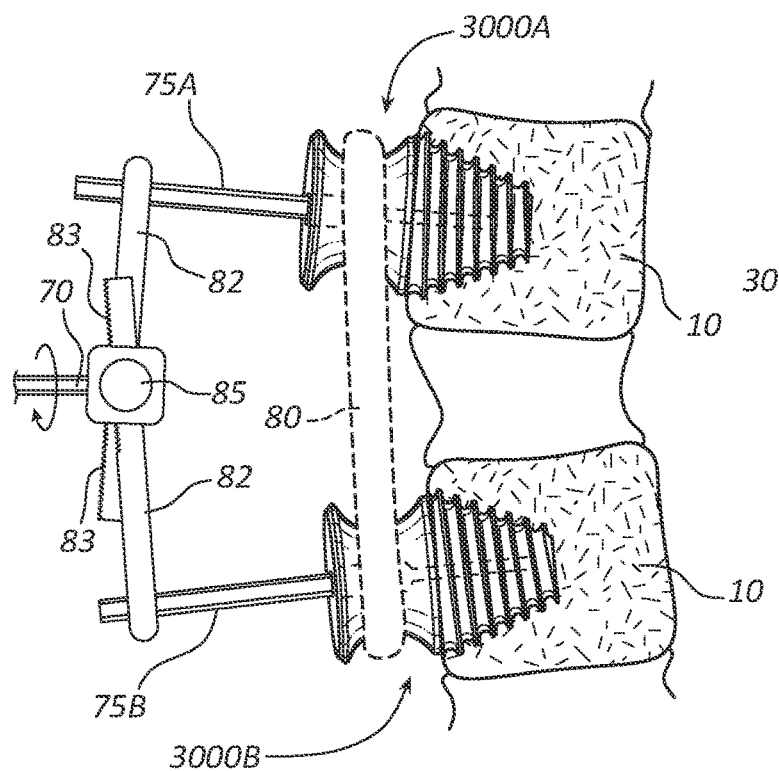

FIGS. 30A-30C depict still another example of a system for spinal deformity correction. This system is again shown with two adjacent bone anchors, namely, bone anchor 3000A and bone anchor 3000B, positioned in two adjacent vertebral bodies 10. This system also comprises a straight ligament 80 that is configured to be formed into a loop and shortened manually between the first configuration shown in FIG. 30A and the second configuration shown in FIG. 30B. However, this system may involve one or more additional steps not required in system 2900.

In particular, system 3000 comprises a temporary set of rods 75A and 75B, which may each be coupled with a respective bone anchor 3000A/3000B. Rods 75A and 75B may independent components, or may be part of an integrated assembly or instrument that is used to tension the anchors 3000A/3000B temporarily until, as shown in FIGS. 30B and 30C, tether 80 may be used to more permanently apply the corrective force initially and temporarily applied by the temporary assembly/components.

One or more components may extend between the temporary rods 75A/75B, such as telescoping or otherwise interconnecting arms. In the depicted embodiment, these elements may comprise a single, temporary tether 82, as shown in FIG. 30B, which may be tensioned to tension anchors 3000A and 3000B via rods 75A and 75B by way of, for example, ratchet mechanism 85. This mechanism may be actuated to shorten the length of tether 82, or another interconnecting piece or pieces, by way of a suitable instrument 70 or another means for selectively shortening a tether/ligament 82.

As was the case with the system depicted in FIGS. 29A and 29B, a series of teeth 83 may be formed along one or both ends of tether 82, which teeth 83 may cooperate with a corresponding set of ratcheting teeth within mechanism 85. Again, alternatively, teeth or other engaging features may only be present within mechanism 85 or any of the other features, elements, and/or instruments disclosed herein may be used instead.

As shown in FIG. 30B, once rods 75A/75B have been tensioned, a permanent ligament 80 may be extended past tether/arms 82 and onto the respective saddles or other ligament engaging members of anchors 3000A and 3000B. Once this has taken place, each of the temporarily elements may be removed. In other words, using the exemplary embodiment of FIGS. 30A-30C, rods 75A and 75B, along with tether/arms 82 and the instrument used to provide the temporary tensioning, may be removed to allow ligament 80 to provide the permanent corrective force to anchors 3000A and 3000B.

It should be understood that a wide variety of alternative features, embodiments, and implementations will be apparent to those of ordinary skill in the art after having received the benefit of this disclosure. For example, in embodiments and implementations in which the means for coupling rods 75A and 75B comprises a removable ligament rather than fixed arms, the removable ligament (element 82 in FIGS. 30A and 30B) may simply be slid onto the adjacent bone anchors rather than using a separate ligament/tether 80.

Figure 31A:
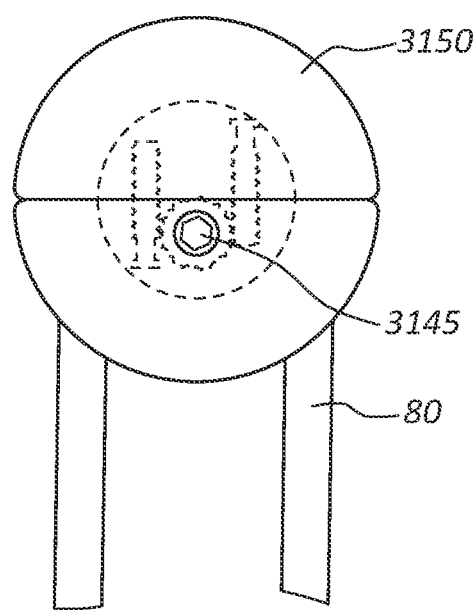
FIG. 31A depicts a selectively expandable ligament saddle according to some embodiments in a first configuration.
Figure 31B:
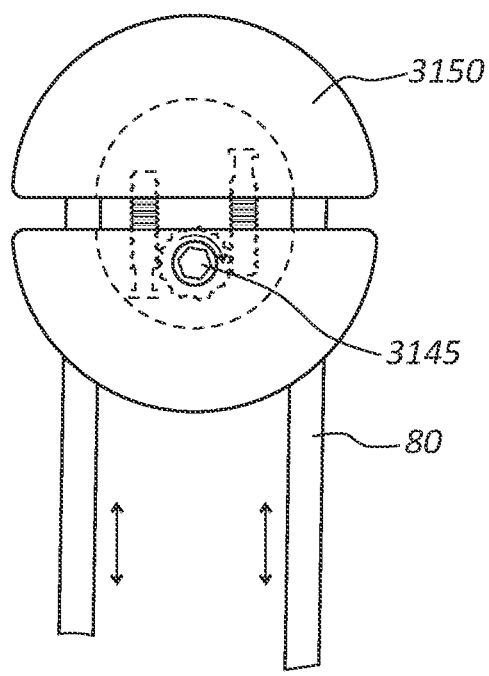
FIG. 31B depicts the selectively expandable ligament saddle of FIG. 31A in a second, expanded configuration.

FIGS. 31A and 31B depict an example of an expandable saddle 3150 or other means for increasing a size of a saddle or other tether engagement member. As shown in FIG. 31A, saddle 3150 may comprise two pieces, one being movable relative to the other, which may allow a surgeon/practitioner to adjust the height of the surface of the saddle 3150 on which the tether 80 is positioned, which may increase the distance to an adjacent bone anchor and/or saddle and thereby increase the force on the ligament/tether 80. This may be accomplished in a number of ways. In the depicted embodiment, a gear having a keyed engagement structure 3145 may be used. The keyed engagement structure 3145 may allow for coupling with a suitable driver or other instrument used to, via the gear, drive a threaded shaft to separate the two pieces of the saddle 3150, as shown in FIG. 31B.

Figure 32A:
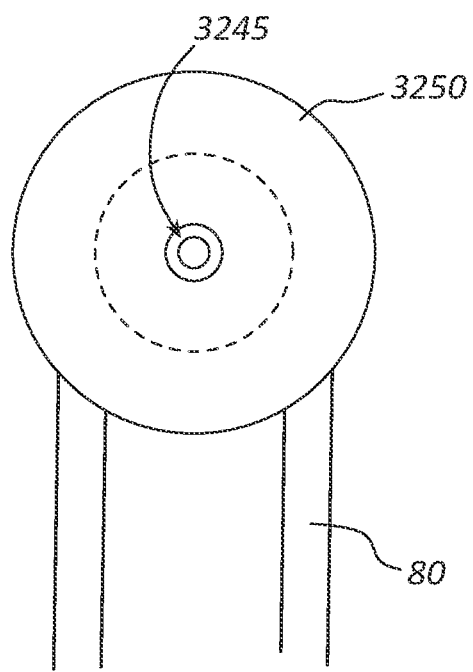
FIG. 32A depicts a selectively expandable ligament saddle having an expandable chamber according to some embodiments in a first configuration.
Figure 32B:
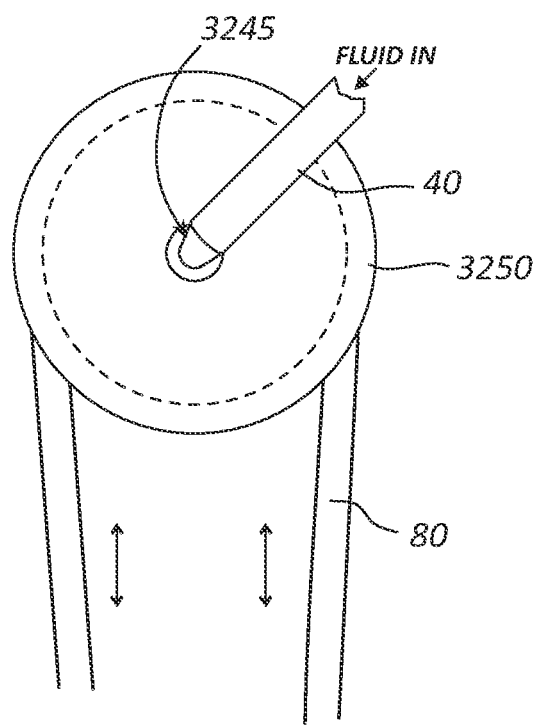
FIG. 32B depicts the selectively expandable ligament saddle of FIG. 32A in a second, expanded configuration.

FIGS. 32A and 32B depict another example of an expandable saddle 3250 or other means for increasing a size of a saddle or other tether engagement member. As shown in FIG. 32A, saddle 3250 may be defined, at least in part, by an expandable chamber, which may be fluidly coupled with a port 3245, which is preferably automatically resealable. Port 3245 may be selectively opened to introduce a gas or another fluid, as shown in FIG. 32B, to expand the size of the expandable chamber and thereby increase the tension on tether/ligament 80. Any suitable instrument comprising a tube 40 or the like may be used to introduce the fluid, which may comprise a syringe in some embodiments. In some embodiments, the syringe may be inserted through, for example, a self-healing/sealing port, which may be made up of, for example, silicone and/or rubber, such as ethylene propylene diene terpolymer (EPDM) foam rubber.

It will be understood by those having skill in the art that changes may be made to the details of the above-described embodiments without departing from the underlying principles presented herein. Any suitable combination of various embodiments, or the features thereof, is contemplated.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

Throughout this specification, any reference to "one embodiment," "an embodiment," or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, figure, or description thereof for the purpose of streamlining the disclosure. This method of disclosure, however, is not to be interpreted as reflecting an intention that any claim require more features than those expressly recited in that claim. Rather, inventive aspects lie in a combination of fewer than all features of any single foregoing disclosed embodiment. It will be apparent to those having skill in the art that changes may be made to the details of the above-described embodiments without departing from the underlying principles set forth herein.

Likewise, benefits, other advantages, and solutions to problems have been described above with regard to various embodiments. However, benefits, advantages, solutions to problems, and any element(s) that may cause any benefit, advantage, or solution to occur or become more pronounced are not to be construed as a critical, a required, or an essential feature or element. The scope of the present invention should, therefore, be determined only by the following claims. The scope of the present invention should, therefore, be determined only by the following claims.

The invention claimed is:

1. A system for spinal deformity correction, comprising:
   a first bone anchor configured to be engaged with a first vertebral body, wherein the first bone anchor comprises:
      an outer thread form formed on an outer surface of the first bone anchor;

an inner chamber; and
at least one of a plurality of bone engaging protrusions formed on an inner surface of the first bone anchor within the inner chamber and a profile that increases in cross-sectional area, at least in part, from a proximal end of the inner chamber to a distal end of the inner chamber;
a second bone anchor configured to be engaged with a second vertebral body, wherein the second bone anchor comprises:
an outer thread form formed on an outer surface of the second bone anchor;
an inner chamber; and
at least one of a plurality of bone engaging protrusions formed on an inner surface of the second bone anchor within the inner chamber and a profile that increases in cross-sectional area, at least in part, from a proximal end of the inner chamber to a distal end of the inner chamber; and
a tether extending between the first bone anchor and the second bone anchor, wherein the tether is configured to apply a corrective force to the first and second vertebral bodies.

2. The system of claim 1, wherein the inner chambers of the first and second bone anchors each comprises a plurality of bone engaging protrusions, and wherein the plurality of bone engaging protrusions comprises an inner thread form formed on an inner surface of each of the inner chambers.

3. The system of claim 1, wherein the inner chambers of the first and second bone anchors each comprises a plurality of bone engaging protrusions, and wherein the plurality of bone engaging protrusions comprises a plurality of bone engaging spikes formed on an inner surface of each the inner chambers.

4. The system of claim 1, wherein the first bone anchor further comprises a removable engagement member configured to be coupled with the first bone anchor so as to protrude away from the first vertebral body, wherein the removable engagement member comprises a seat for receiving the tether.

5. The system of claim 1, wherein the inner chambers of the first and second bone anchors each comprises at least one stepped region in which a cross-sectional area of the inner chamber of each of the first and second bone anchors decreases in a distal to proximal direction.

6. The system of claim 1, wherein the outer thread forms of the first and second bone anchors each comprises at least two distinct sections.

7. The system of claim 6, further comprising a bone anchor sleeve configured to receive the first bone anchor, wherein the at least two distinct sections comprises a first section configured to threadably engage the bone anchor sleeve and a second section configured to threadably engage the first vertebral body.

8. The system of claim 7, wherein the bone anchor sleeve is configured to engage the first bone anchor so as to provide a region outside of the inner chamber of the first bone anchor within which vertebral bone may be compressed during installation.

9. A method for applying a corrective force to a spinal column, the method comprising the steps of:
advancing a first bone anchor into a first vertebral body of a spinal column;
compacting cancellous bone within an inner chamber of the first bone anchor, wherein the inner chamber comprises at least one of a plurality of bone engaging protrusions and a profile that increases in cross-sectional area, at least in part, from a proximal end of the inner chamber to a distal end of the inner chamber;
advancing a second bone anchor into a second vertebral body of the spinal column;
compacting cancellous bone within an inner chamber of the second bone anchor, wherein the inner chamber comprises at least one of a plurality of bone engaging protrusions and a profile that increases in cross-sectional area, at least in part, from a proximal end of the inner chamber to a distal end of the inner chamber; and
coupling a tether between the first and second bone anchors to apply a force between the first and second bone anchors and thereby apply a corrective force to at least a portion of the spinal column.

10. The method of claim 9, wherein the inner chambers of the first and second bone anchors each comprises a plurality of bone engaging protrusions, and wherein the step of compacting cancellous bone within the inner chamber comprises drawing cancellous bone into the inner chamber with the plurality of bone engaging protrusions while the first bone anchor is advanced into the first vertebral body.

11. The method of claim 9, wherein the first bone anchor is offset from the second bone anchor relative to the spinal column such that the corrective force includes a derotational corrective component.

12. The method of claim 11, further comprising advancing a third bone anchor into the first vertebral body adjacent to the first bone anchor.

13. The method of claim 9, wherein the first bone anchor comprises a first protrusion extending transverse to a primary axis of the first bone anchor, wherein the second bone anchor comprises a second protrusion extending transverse to a primary axis of the second bone anchor, and wherein the step of coupling a tether between the first and second bone anchors comprises coupling the tether to the first protrusion and the second protrusion.

14. The method of claim 13, wherein the first protrusion extends in a direction at least substantially opposite from the second protrusion relative to the spinal column such that that the corrective force includes a derotational corrective component.

15. A method for applying a corrective force to a spinal column, the method comprising the steps of:
advancing a first bone anchor into a first vertebral body of a spinal column while simultaneously redistributing and compacting vertebral bone into an inner chamber of the first bone anchor;
advancing a second bone anchor into a second vertebral body of the spinal column while simultaneously redistributing and compacting vertebral bone into an inner chamber of the second bone anchor; and
coupling a tether between the first and second bone anchors to apply a force between the first and second bone anchors and thereby apply a corrective force to at least a portion of the spinal column.

16. The method of claim 15, further comprising increasing tension on the tether to increase the force between the first and second bone anchors.

17. The method of claim 16, wherein the step of increasing tension on the tether comprises increasing a size of at least a portion of an engagement member coupled to at least one of the first and second bone anchors and within which at least a portion of the tether is positioned.

18. The method of claim 16, wherein the step of increasing tension on the tether comprises decreasing a length of the tether.

19. The method of claim 18, wherein the tether comprises a loop tether, and wherein the step of increasing tension on the tether comprises heat shrinking the loop tether.

20. The method of claim 15, further comprising:
- tensioning the first and second bone anchors with a temporary tether having a non-fixed length;
- after the step of tensioning the first and second bone anchors with the temporary tether, coupling the tether between the first and second bone anchors; and
- removing the temporary tether from being coupled with the first and second bone anchors.

\* \* \* \* \*